United States Patent
Argenta et al.

(10) Patent No.: US 9,289,193 B2
(45) Date of Patent: Mar. 22, 2016

(54) APPARATUS AND METHOD FOR CARDIAC TISSUE MODULATION BY TOPICAL APPLICATION OF VACUUM TO MINIMIZE CELL DEATH AND DAMAGE

(75) Inventors: Louis C. Argenta, Winston-Salem, NC (US); David L. Carroll, Winston-Salem, NC (US); James E. Jordan, Clemmons, NC (US); Nicole H. Levi, Winston-Salem, NC (US); Jie Liu, Winston-Salem, NC (US); Michael J. Morykwas, Winston-Salem, NC (US); William D. Wagner, Clemmons, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 554 days.

(21) Appl. No.: 12/504,076

(22) Filed: Jul. 16, 2009

(65) Prior Publication Data
US 2010/0121229 A1   May 13, 2010

Related U.S. Application Data

(60) Provisional application No. 61/088,558, filed on Aug. 13, 2008, provisional application No. 61/081,997, filed on Jul. 18, 2008.

(51) Int. Cl.
*A61B 17/08* (2006.01)
*A61B 17/00* (2006.01)
(Continued)

(52) U.S. Cl.
CPC ..... *A61B 17/00234* (2013.01); *A61F 13/00068* (2013.01); *A61M 1/0088* (2013.01); *A61B 19/46* (2013.01); *A61B 2017/00243* (2013.01); *A61B 2017/306* (2013.01); *A61B 2019/464* (2013.01); *A61F 2013/0028* (2013.01); *A61M 1/0031* (2013.01); *A61M 1/0037* (2013.01); *A61M 2210/1082* (2013.01); *A61M 2210/125* (2013.01)

(58) Field of Classification Search
CPC ............... A61B 17/02234; A61B 2017/00243; A61B 2017/306; A61B 2019/464
USPC .............. 606/213, 215; 604/11, 500; 424/423
See application file for complete search history.

(56) References Cited

U.S. PATENT DOCUMENTS

| 765,746 A | 7/1904 | Miner |
| 774,529 A | 11/1904 | Nieschang |

(Continued)

FOREIGN PATENT DOCUMENTS

| AU | 2003231870 | 4/2009 |
| DE | 372727 | 3/1923 |

(Continued)

OTHER PUBLICATIONS

Lindstedt, et al. "Myocardial topical negative pressure increases blood flow in hypothermic, ischemic myocardium". Scand Cardiovasc J. Mar. 4, 2008; 1-9.*

(Continued)

*Primary Examiner* — Nathan R Price
*Assistant Examiner* — Weng Lee
(74) *Attorney, Agent, or Firm* — Niels Haun; Dann, Dorfman, Herrell & Skillman, P.C.

(57) ABSTRACT

A method and apparatus are provided for treating cardiac tissue to modulate ischemic heart tissue with topical subatmospheric pressure to minimize cell death and damage.

49 Claims, 12 Drawing Sheets

(51) Int. Cl.
  *A61M 1/00* (2006.01)
  *A61B 17/30* (2006.01)
  *A61B 19/00* (2006.01)
  *A61F 13/00* (2006.01)

(56) References Cited

U.S. PATENT DOCUMENTS

| | | | |
|---|---|---|---|
| 843,674 A | 2/1907 | Funk |
| 1,000,001 A | 8/1911 | Holz |
| 1,355,679 A | 10/1920 | McConnell |
| 1,355,846 A | 10/1920 | Rannells |
| 1,385,346 A | 7/1921 | Taylor |
| 1,936,129 A | 11/1933 | Fisk |
| 2,025,492 A | 12/1935 | Aird |
| 2,122,121 A | 6/1938 | Tillotson |
| 2,195,771 A | 4/1940 | Estler |
| 2,221,758 A | 11/1940 | Elmquist |
| 2,232,254 A | 2/1941 | Morgan |
| 2,280,915 A | 4/1942 | Johnson |
| 2,338,339 A | 1/1944 | LaMere |
| 2,443,481 A | 6/1948 | Sene |
| 2,547,758 A | 4/1951 | Keeling |
| 2,573,791 A | 11/1951 | Howells |
| 2,577,945 A | 12/1951 | Atherton |
| 2,632,443 A | 3/1953 | Lesher |
| 2,682,873 A | 7/1954 | Evans |
| 2,910,763 A | 11/1959 | Lauterbach |
| 2,969,057 A | 1/1961 | Simmons |
| 3,026,874 A | 3/1962 | Stevens |
| 3,042,041 A | 7/1962 | Jascalevich |
| 3,115,138 A | 12/1963 | McElvenny |
| 3,315,665 A | 4/1967 | MacLeod |
| 3,324,855 A | 6/1967 | Heimlich |
| 3,367,332 A | 2/1968 | Groves |
| 3,382,867 A | 5/1968 | Reaves |
| 3,429,313 A | 2/1969 | Romanelli |
| 3,486,504 A | 12/1969 | Austin, Jr. |
| 3,520,300 A | 7/1970 | Flower et al. |
| 3,528,416 A | 9/1970 | Chamberlain |
| 3,568,675 A | 3/1971 | Harvey |
| 3,572,340 A | 3/1971 | Lloyd et al. |
| 3,610,238 A | 10/1971 | Rich, Jr. |
| 3,648,692 A | 3/1972 | Wheeler |
| 3,682,180 A | 8/1972 | McFarlane |
| 3,713,622 A | 1/1973 | Dinger |
| 3,753,439 A | 8/1973 | Brugarolas et al. |
| 3,782,377 A | 1/1974 | Rychlik |
| 3,782,387 A | 1/1974 | Falabella |
| 3,812,972 A | 5/1974 | Rosenblum |
| 3,814,095 A | 6/1974 | Lubens |
| 3,826,254 A | 7/1974 | Mellor |
| 3,874,387 A | 4/1975 | Barbieri |
| 3,896,810 A | 7/1975 | Akiyama |
| 3,903,882 A | 9/1975 | Augurt |
| 3,908,664 A | 9/1975 | Loseff |
| 3,935,863 A | 2/1976 | Kliger |
| 3,938,540 A | 2/1976 | Holbrook et al. |
| 3,954,105 A | 5/1976 | Nordby et al. |
| 3,975,567 A | 8/1976 | Lock |
| 3,978,855 A | 9/1976 | McRae et al. |
| 3,992,725 A | 11/1976 | Homsy |
| 3,993,080 A | 11/1976 | Loseff |
| 3,998,227 A | 12/1976 | Holbrook et al. |
| RE29,319 E | 7/1977 | Nordby et al. |
| 4,080,970 A | 3/1978 | Miller |
| 4,112,947 A | 9/1978 | Nehring |
| 4,139,004 A | 2/1979 | Gonzalez, Jr. |
| 4,149,541 A | 4/1979 | Gammons et al. |
| 4,156,066 A | 5/1979 | Gould |
| 4,169,563 A | 10/1979 | Leu |
| 4,184,510 A | 1/1980 | Murry et al. |
| 4,187,852 A | 2/1980 | Urry et al. |
| 4,191,204 A | 3/1980 | Nehring |
| 4,221,215 A | 9/1980 | Mandelbaum |
| 4,224,941 A | 9/1980 | Stivala |
| 4,224,945 A | 9/1980 | Cohen |
| 4,250,882 A | 2/1981 | Adair |
| 4,256,109 A | 3/1981 | Nichols |
| 4,261,363 A | 4/1981 | Russo |
| 4,275,721 A | 6/1981 | Olson |
| 4,297,995 A | 11/1981 | Golub |
| 4,341,209 A | 7/1982 | Schaar |
| 4,373,519 A | 2/1983 | Errede et al. |
| 4,382,441 A | 5/1983 | Svedman |
| 4,392,853 A | 7/1983 | Muto |
| 4,399,816 A | 8/1983 | Spangler |
| 4,419,097 A | 12/1983 | Rowland |
| 4,452,845 A | 6/1984 | Lloyd et al. |
| 4,457,755 A | 7/1984 | Wilson |
| 4,459,139 A | 7/1984 | vonReis et al. |
| 4,465,062 A | 8/1984 | Versaggi et al. |
| 4,465,485 A | 8/1984 | Kashmer et al. |
| 4,475,909 A | 10/1984 | Eisenberg |
| 4,480,638 A | 11/1984 | Schmid |
| 4,499,896 A | 2/1985 | Heinecke |
| RE31,887 E | 5/1985 | Hodgson |
| 4,525,166 A | 6/1985 | Leclerc |
| 4,533,352 A | 8/1985 | Van Beek |
| 4,540,412 A | 9/1985 | Van Overloop |
| 4,543,100 A | 9/1985 | Brodsky |
| 4,553,967 A | 11/1985 | Ferguson |
| 4,569,674 A | 2/1986 | Phillips et al. |
| 4,573,965 A | 3/1986 | Russo |
| 4,579,555 A | 4/1986 | Russo |
| 4,605,399 A | 8/1986 | Weston et al. |
| 4,608,041 A | 8/1986 | Nielsen |
| 4,624,656 A | 11/1986 | Clark et al. |
| 4,627,427 A | 12/1986 | Arco |
| 4,633,863 A | 1/1987 | Filips |
| 4,637,819 A | 1/1987 | Ouellette |
| 4,640,688 A | 2/1987 | Hauser |
| 4,641,643 A | 2/1987 | Greer |
| 4,655,754 A | 4/1987 | Richmond et al. |
| 4,661,093 A | 4/1987 | Beck et al. |
| 4,661,530 A | 4/1987 | Gogolewski et al. |
| 4,664,652 A | 5/1987 | Weilbacher |
| 4,664,662 A | 5/1987 | Webster |
| 4,667,666 A | 5/1987 | Fryslie |
| 4,679,590 A | 7/1987 | Hergenroeder |
| 4,710,165 A | 12/1987 | McNeil et al. |
| 4,713,052 A | 12/1987 | Beck |
| 4,717,382 A | 1/1988 | Clemens et al. |
| 4,733,659 A | 3/1988 | Edenbaum |
| 4,743,232 A | 5/1988 | Kruger |
| 4,747,166 A | 5/1988 | Kuntz |
| 4,753,231 A | 6/1988 | Lang et al. |
| 4,753,232 A | 6/1988 | Ward |
| 4,759,354 A | 7/1988 | Quarfoot |
| 4,764,167 A | 8/1988 | Tu |
| 4,773,409 A | 9/1988 | Cilento |
| 4,778,446 A | 10/1988 | Jensen |
| 4,778,456 A | 10/1988 | Lokken |
| 4,820,265 A | 4/1989 | Desatnick et al. |
| 4,820,284 A | 4/1989 | Hauri |
| 4,822,278 A | 4/1989 | Oliva |
| 4,834,110 A | 5/1989 | Richard |
| 4,836,192 A | 6/1989 | Abbate |
| 4,838,883 A | 6/1989 | Matsuura |
| 4,840,187 A | 6/1989 | Brazier |
| 4,841,962 A | 6/1989 | Berg et al. |
| 4,851,545 A | 7/1989 | Song et al. |
| 4,860,737 A | 8/1989 | Lang et al. |
| 4,863,449 A | 9/1989 | Therriault |
| 4,872,450 A | 10/1989 | Austad |
| 4,875,473 A | 10/1989 | Alvarez |
| 4,878,901 A | 11/1989 | Sachse |
| 4,890,608 A | 1/1990 | Steer |
| 4,897,081 A | 1/1990 | Poirier |
| 4,906,233 A | 3/1990 | Moriuchi et al. |
| 4,906,240 A | 3/1990 | Reed |
| 4,917,112 A | 4/1990 | Kalt |
| 4,921,492 A | 5/1990 | Schultz et al. |
| 4,925,447 A | 5/1990 | Rosenblatt |
| 4,931,519 A | 6/1990 | Song et al. |

(56) References Cited

U.S. PATENT DOCUMENTS

| | | |
|---|---|---|
| 4,941,882 A | 7/1990 | Ward et al. |
| 4,953,565 A | 9/1990 | Tachibana et al. |
| 4,969,880 A | 11/1990 | Zamierowski |
| 4,969,881 A | 11/1990 | Viesturs |
| 4,988,336 A | 1/1991 | Kohn |
| 4,990,144 A | 2/1991 | Blott |
| 4,991,574 A | 2/1991 | Pocknell |
| 4,997,425 A | 3/1991 | Shioya |
| 5,002,528 A | 3/1991 | Palestrant |
| 5,002,529 A | 3/1991 | Cunningham |
| 5,003,971 A | 4/1991 | Buckley |
| 5,014,389 A | 5/1991 | Ogilvie |
| 5,019,086 A | 5/1991 | Neward |
| 5,024,841 A | 6/1991 | Chu et al. |
| 5,034,006 A | 7/1991 | Hosoda |
| 5,035,884 A | 7/1991 | Song et al. |
| 5,042,978 A | 8/1991 | Quenin |
| 5,060,662 A | 10/1991 | Farnsworth, III |
| 5,071,403 A | 12/1991 | Larason |
| 5,073,172 A | 12/1991 | Fell |
| 5,086,763 A | 2/1992 | Hathman |
| 5,086,764 A | 2/1992 | Gilman |
| 5,100,396 A | 3/1992 | Zamierowski |
| 5,101,808 A | 4/1992 | Kobayashi |
| 5,106,362 A | 4/1992 | Gilman |
| 5,106,629 A | 4/1992 | Cartmell |
| 5,113,871 A | 5/1992 | Viljanto |
| 5,135,518 A | 8/1992 | Vera |
| 5,147,338 A | 9/1992 | Lang |
| 5,149,331 A | 9/1992 | Ferdman et al. |
| 5,152,757 A | 10/1992 | Eriksson |
| 5,160,322 A | 11/1992 | Scheremet |
| 5,167,613 A | 12/1992 | Karami |
| 5,170,781 A | 12/1992 | Loomis |
| 5,176,663 A | 1/1993 | Svedman |
| 5,176,667 A | 1/1993 | DeBring |
| 5,192,282 A | 3/1993 | Draenert |
| 5,215,539 A | 6/1993 | Schoolman |
| 5,224,947 A | 7/1993 | Cooper |
| 5,230,350 A | 7/1993 | Fentress |
| 5,261,893 A | 11/1993 | Zamierowski |
| 5,263,922 A | 11/1993 | Sova |
| 5,298,015 A | 3/1994 | Komatsuzaki |
| 5,330,452 A | 7/1994 | Zook |
| 5,344,415 A | 9/1994 | DeBusk |
| 5,349,965 A | 9/1994 | McCarver |
| 5,358,494 A | 10/1994 | Svedman |
| 5,376,252 A | 12/1994 | Ekstrom |
| 5,395,315 A | 3/1995 | Griep |
| 5,419,768 A | 5/1995 | Kayser |
| 5,431,662 A | 7/1995 | Nicholas |
| 5,437,651 A | 8/1995 | Todd |
| 5,445,604 A | 8/1995 | Lang |
| 5,447,492 A | 9/1995 | Cartmell et al. |
| 5,451,215 A | 9/1995 | Wolter |
| 5,456,267 A | 10/1995 | Stark |
| 5,478,333 A | 12/1995 | Asherman, Jr. |
| 5,484,399 A | 1/1996 | DiResta et al. |
| 5,484,427 A | 1/1996 | Gibbons |
| 5,487,889 A | 1/1996 | Eckert |
| 5,490,962 A | 2/1996 | Cima et al. |
| 5,496,262 A | 3/1996 | Johnson, Jr. |
| 5,520,652 A | 5/1996 | Peterson |
| 5,522,901 A | 6/1996 | Thomas et al. |
| 5,527,293 A | 6/1996 | Zamierowski |
| 5,531,670 A | 7/1996 | Westby |
| 5,542,918 A | 8/1996 | Atkinson |
| 5,549,584 A | 8/1996 | Gross |
| 5,556,375 A | 9/1996 | Ewall |
| 5,578,022 A | 11/1996 | Scherson |
| 5,580,353 A | 12/1996 | Mendes et al. |
| 5,588,955 A | 12/1996 | Johnson, Jr. |
| 5,599,330 A | 2/1997 | Rainin |
| 5,607,388 A | 3/1997 | Ewall |
| 5,607,590 A | 3/1997 | Shimizu |
| 5,628,735 A | 5/1997 | Skow |
| 5,636,643 A | 6/1997 | Argenta et al. |
| 5,645,081 A | 7/1997 | Argenta et al. |
| 5,655,258 A | 8/1997 | Heintz |
| 5,656,027 A | 8/1997 | Ellingboe |
| 5,662,598 A | 9/1997 | Tobin |
| 5,662,624 A | 9/1997 | Sundstrom |
| 5,662,625 A | 9/1997 | Westwood |
| 5,678,564 A | 10/1997 | Lawrence |
| 5,697,920 A | 12/1997 | Gibbons |
| 5,716,360 A | 2/1998 | Baldwin et al. |
| 5,717,005 A | 2/1998 | Richardson |
| 5,717,030 A | 2/1998 | Dunn |
| 5,720,720 A | 2/1998 | Laske |
| 5,733,884 A | 3/1998 | Barbul |
| 5,735,833 A | 4/1998 | Olson |
| 5,736,372 A | 4/1998 | Vacanti et al. |
| 5,738,686 A | 4/1998 | Kubein-Meesenburg et al. |
| 5,743,912 A | 4/1998 | Lahille et al. |
| 5,762,640 A | 6/1998 | Kajiwara |
| 5,766,618 A | 6/1998 | Laurencin et al. |
| 5,782,871 A | 7/1998 | Fujiwara |
| 5,810,840 A | 9/1998 | Lindsay |
| 5,817,145 A | 10/1998 | Augustine |
| 5,827,246 A | 10/1998 | Bowen |
| 5,869,080 A | 2/1999 | McGregor et al. |
| 5,876,359 A | 3/1999 | Bock et al. |
| 5,911,222 A | 6/1999 | Lawrence |
| 5,919,476 A | 7/1999 | Fischer |
| 5,921,972 A | 7/1999 | Skow |
| 5,928,174 A | 7/1999 | Gibbons |
| 5,935,136 A | 8/1999 | Hulse et al. |
| 5,941,859 A | 8/1999 | Lerman |
| 5,947,914 A | 9/1999 | Augustine |
| 5,951,295 A | 9/1999 | Lyles et al. |
| 5,954,680 A | 9/1999 | Augustine |
| 5,958,314 A | 9/1999 | Draenert |
| 5,961,480 A | 10/1999 | Augustine |
| 5,964,721 A | 10/1999 | Augustine |
| 5,964,723 A | 10/1999 | Augustine |
| 5,964,733 A | 10/1999 | Laabs et al. |
| 5,968,047 A | 10/1999 | Reed |
| 5,986,163 A | 11/1999 | Augustine |
| 6,010,527 A | 1/2000 | Augustine |
| 6,045,518 A | 4/2000 | Augustine |
| 6,045,541 A | 4/2000 | Matsumoto |
| 6,051,016 A | 4/2000 | Mesaros et al. |
| 6,053,416 A | 4/2000 | Specht |
| 6,071,254 A | 6/2000 | Augustine |
| 6,071,267 A | 6/2000 | Zamierowski |
| 6,071,304 A | 6/2000 | Augustine |
| 6,080,189 A | 6/2000 | Augustine |
| 6,080,243 A | 6/2000 | Insley |
| 6,086,587 A | 7/2000 | Hawk |
| 6,087,553 A | 7/2000 | Cohen et al. |
| 6,093,160 A | 7/2000 | Augustine |
| 6,095,148 A | 8/2000 | Shastri |
| 6,095,992 A | 8/2000 | Augustine |
| 6,106,913 A | 8/2000 | Scardino et al. |
| 6,110,197 A | 8/2000 | Augustine |
| 6,113,561 A | 9/2000 | Augustine |
| 6,117,111 A | 9/2000 | Fleischmann |
| 6,135,116 A | 10/2000 | Vogel |
| 6,142,982 A | 11/2000 | Hunt |
| 6,143,945 A | 11/2000 | Augustine |
| 6,146,423 A | 11/2000 | Cohen et al. |
| 6,159,246 A | 12/2000 | Mendes et al. |
| 6,174,306 B1 | 1/2001 | Fleischmann |
| 6,187,047 B1 | 2/2001 | Kwan et al. |
| 6,190,391 B1 | 2/2001 | Stubbs |
| 6,203,563 B1 | 3/2001 | Fernandez |
| 6,207,875 B1 | 3/2001 | Lindqvist |
| 6,213,965 B1 | 4/2001 | Augustine |
| 6,213,966 B1 | 4/2001 | Augustine |
| 6,217,535 B1 | 4/2001 | Augustine |
| 6,235,009 B1 | 5/2001 | Skow |
| 6,235,047 B1 | 5/2001 | Augustine |
| 6,241,697 B1 | 6/2001 | Augustine |
| 6,241,698 B1 | 6/2001 | Augustine |

(56) References Cited

U.S. PATENT DOCUMENTS

| | | |
|---|---|---|
| 6,248,084 B1 | 6/2001 | Augustine |
| 6,254,557 B1 | 7/2001 | Augustine |
| 6,254,580 B1 | 7/2001 | Svedman |
| 6,264,622 B1 | 7/2001 | Augustine |
| 6,264,979 B1 | 7/2001 | Svedman |
| 6,267,740 B1 | 7/2001 | Augustine |
| 6,283,931 B1 | 9/2001 | Augustine |
| 6,284,941 B1 | 9/2001 | Cox |
| 6,290,685 B1 | 9/2001 | Insley |
| 6,293,917 B1 | 9/2001 | Augustine |
| 6,323,146 B1 | 11/2001 | Pugh |
| 6,325,788 B1 | 12/2001 | McKay |
| 6,344,061 B1 | 2/2002 | Leitao et al. |
| 6,345,623 B1 | 2/2002 | Heaton et al. |
| 6,355,215 B1 | 3/2002 | Poggie et al. |
| 6,359,189 B1 | 3/2002 | Fleischmann |
| 6,377,653 B1 | 4/2002 | Lee et al. |
| 6,394,948 B1 | 5/2002 | Borst et al. |
| 6,398,767 B1 | 6/2002 | Fleischmann |
| 6,430,427 B1 | 8/2002 | Lee et al. |
| 6,458,109 B1 | 10/2002 | Henley |
| 6,484,716 B1 | 11/2002 | Leininger |
| 6,485,503 B2 | 11/2002 | Jacobs et al. |
| 6,488,643 B1 | 12/2002 | Tumey |
| 6,491,693 B1 | 12/2002 | Lytinas |
| 6,520,982 B1 | 2/2003 | Boynton |
| 6,551,317 B2 | 4/2003 | Berish et al. |
| 6,553,998 B2 | 4/2003 | Heaton et al. |
| 6,555,729 B1 | 4/2003 | Fleischmann |
| 6,641,604 B1 | 11/2003 | Adelman |
| 6,648,862 B2 | 11/2003 | Watson |
| 6,663,349 B1 | 12/2003 | Discenzo |
| 6,673,028 B1 | 1/2004 | Argenta et al. |
| 6,682,491 B2 | 1/2004 | Johnson |
| 6,685,681 B2 | 2/2004 | Lockwood |
| 6,695,823 B1 | 2/2004 | Lina |
| 6,712,851 B1 | 3/2004 | Lemperle et al. |
| 6,749,592 B2 | 6/2004 | Lord |
| 6,752,794 B2 | 6/2004 | Lockwood |
| 6,755,807 B2 | 6/2004 | Risk, Jr. |
| 6,764,462 B2 | 7/2004 | Risk, Jr. |
| 6,767,334 B1 | 7/2004 | Randolph |
| 6,770,794 B2 | 8/2004 | Fleischmann |
| 6,790,455 B2 | 9/2004 | Chu et al. |
| 6,793,633 B2 | 9/2004 | Douglas et al. |
| 6,800,074 B2 | 10/2004 | Henley |
| 6,814,079 B2 | 11/2004 | Heaton et al. |
| 6,824,533 B2 | 11/2004 | Risk, Jr. |
| 6,840,960 B2 | 1/2005 | Bubb |
| 6,855,135 B2 | 2/2005 | Lockwood |
| 6,856,821 B2 | 2/2005 | Johnson |
| 6,878,119 B2 | 4/2005 | Johnson |
| 6,887,246 B2 | 5/2005 | Bhatnagar et al. |
| 6,936,037 B2 | 8/2005 | Bubb |
| 6,951,553 B2 | 10/2005 | Bubb |
| 6,988,423 B2 | 1/2006 | Bolam |
| 6,994,702 B1 | 2/2006 | Johnson |
| 7,004,915 B2 | 2/2006 | Boynton |
| 7,022,113 B2 | 4/2006 | Lockwood |
| 7,066,960 B1 | 6/2006 | Dickman |
| 7,070,584 B2 | 7/2006 | Johnson |
| 7,077,832 B2 | 7/2006 | Fleischmann |
| 7,108,683 B2 | 9/2006 | Zamierowski |
| 7,117,869 B2 | 10/2006 | Heaton |
| 7,128,735 B2 | 10/2006 | Weston |
| 7,144,390 B1 | 12/2006 | Hannigan |
| 7,169,151 B1 | 1/2007 | Lytinas |
| 7,175,625 B2 | 2/2007 | Culbert |
| 7,198,046 B1 | 4/2007 | Argenta |
| 7,216,651 B2 | 5/2007 | Argenta |
| 7,229,425 B2 | 6/2007 | Dunagan |
| 7,276,051 B1 | 10/2007 | Henley et al. |
| 7,279,612 B1 | 10/2007 | Heaton et al. |
| 7,344,512 B2 | 3/2008 | Yamazaki et al. |
| 7,520,872 B2 | 4/2009 | Biggie et al. |
| 7,722,894 B2 | 5/2010 | Wang et al. |
| 7,763,077 B2 | 7/2010 | Friedman et al. |
| 7,931,651 B2 | 4/2011 | Webb et al. |
| 8,235,955 B2 | 8/2012 | Blott et al. |
| 2001/0023349 A1 | 9/2001 | VanTassel et al. |
| 2001/0029956 A1 | 10/2001 | Argenta et al. |
| 2001/0043943 A1 | 11/2001 | Coffey |
| 2002/0065494 A1 | 5/2002 | Lockwood et al. |
| 2002/0082567 A1 | 6/2002 | Lockwood et al. |
| 2002/0115952 A1 | 8/2002 | Johnson et al. |
| 2002/0120185 A1 | 8/2002 | Johnson |
| 2002/0143286 A1 | 10/2002 | Tumey |
| 2002/0143403 A1 | 10/2002 | Vaidyanathan et al. |
| 2002/0161317 A1 | 10/2002 | Risk et al. |
| 2002/0161346 A1 | 10/2002 | Lockwood et al. |
| 2002/0198503 A1 | 12/2002 | Risk, Jr. et al. |
| 2002/0198504 A1 | 12/2002 | Risk, Jr. et al. |
| 2003/0040687 A1 | 2/2003 | Boynton |
| 2003/0050594 A1 | 3/2003 | Zamierowski |
| 2003/0093075 A1 | 5/2003 | Levinson |
| 2003/0108587 A1 | 6/2003 | Orgill et al. |
| 2003/0109855 A1 | 6/2003 | Solem et al. |
| 2003/0118692 A1 | 6/2003 | Wang et al. |
| 2003/0130599 A1 | 7/2003 | Restle et al. |
| 2003/0187367 A1 | 10/2003 | Odland |
| 2003/0208149 A1 | 11/2003 | Coffey |
| 2003/0219469 A1 | 11/2003 | Johnson |
| 2003/0225347 A1 | 12/2003 | Argenta |
| 2003/0225441 A1 | 12/2003 | Boynton |
| 2004/0006319 A1 | 1/2004 | Lina |
| 2004/0024351 A1 | 2/2004 | Greter |
| 2004/0030304 A1 | 2/2004 | Hunt |
| 2004/0039391 A1 | 2/2004 | Argenta |
| 2004/0039415 A1 | 2/2004 | Zamierowski |
| 2004/0064111 A1 | 4/2004 | Lockwood et al. |
| 2004/0064132 A1 | 4/2004 | Boehringer |
| 2004/0073151 A1 | 4/2004 | Weston |
| 2004/0122434 A1 | 6/2004 | Argenta |
| 2004/0127845 A1 | 7/2004 | Renz et al. |
| 2004/0138522 A1 | 7/2004 | Haarstad et al. |
| 2004/0167482 A1 | 8/2004 | Watson |
| 2004/0197375 A1 | 10/2004 | Rezania et al. |
| 2004/0225178 A1 | 11/2004 | Kriewall |
| 2004/0225208 A1 | 11/2004 | Johnson |
| 2004/0249353 A1 | 12/2004 | Risks, Jr. et al. |
| 2004/0260230 A1 | 12/2004 | Randolph |
| 2005/0020955 A1 | 1/2005 | Sanders |
| 2005/0028828 A1 | 2/2005 | Heaton et al. |
| 2005/0043659 A1 | 2/2005 | Challis et al. |
| 2005/0063939 A1 | 3/2005 | Ameer et al. |
| 2005/0065484 A1 | 3/2005 | Watson, Jr. |
| 2005/0079200 A1 | 4/2005 | Rathenow et al. |
| 2005/0090787 A1 | 4/2005 | Risk, Jr. et al. |
| 2005/0101940 A1 | 5/2005 | Radl |
| 2005/0124966 A1 | 6/2005 | Karpowicz |
| 2005/0131327 A1 | 6/2005 | Lockwood et al. |
| 2005/0148913 A1 | 7/2005 | Weston |
| 2005/0165350 A1 | 7/2005 | Greter |
| 2005/0177190 A1 | 8/2005 | Zamierowski |
| 2005/0182445 A1 | 8/2005 | Zamierowski |
| 2005/0197645 A1 | 9/2005 | Karpowicz |
| 2005/0203452 A1 | 9/2005 | Weston |
| 2005/0209574 A1 | 9/2005 | Boehringer |
| 2005/0222527 A1 | 10/2005 | Miller |
| 2005/0222528 A1 | 10/2005 | Weston |
| 2005/0222544 A1 | 10/2005 | Weston |
| 2005/0228329 A1 | 10/2005 | Boehringer |
| 2005/0234510 A1 | 10/2005 | Zamierowski |
| 2005/0240220 A1 | 10/2005 | Zamierowski |
| 2005/0261615 A1 | 11/2005 | Weston |
| 2005/0261642 A1 | 11/2005 | Weston |
| 2005/0283105 A1 | 12/2005 | Heaton et al. |
| 2006/0025727 A1 | 2/2006 | Boehringer |
| 2006/0029650 A1 | 2/2006 | Coffey |
| 2006/0029675 A1 | 2/2006 | Ginther |
| 2006/0079852 A1 | 4/2006 | Bubb |
| 2006/0100586 A1 | 5/2006 | Karpowicz |
| 2006/0149170 A1 | 7/2006 | Boynton |
| 2006/0149171 A1 | 7/2006 | Vogel |

(56) References Cited

U.S. PATENT DOCUMENTS

| | | |
|---|---|---|
| 2006/0149176 A1 | 7/2006 | Bolam |
| 2006/0173253 A1 | 8/2006 | Ganapathy |
| 2006/0189910 A1 | 8/2006 | Johnson |
| 2006/0193888 A1 | 8/2006 | Lye et al. |
| 2006/0213527 A1 | 9/2006 | Argenta et al. |
| 2006/0263417 A1 | 11/2006 | Lelkes et al. |
| 2006/0286076 A1 | 12/2006 | Fleischmann |
| 2006/0293169 A1 | 12/2006 | Srinivasan et al. |
| 2007/0005028 A1 | 1/2007 | Risk, Jr. et al. |
| 2007/0014837 A1 | 1/2007 | Johnson |
| 2007/0021697 A1 | 1/2007 | Ginter |
| 2007/0021698 A1 | 1/2007 | Fleischmann |
| 2007/0032754 A1 | 2/2007 | Walsh |
| 2007/0071790 A1 | 3/2007 | Ameer et al. |
| 2007/0135795 A1 | 6/2007 | De Paulis |
| 2007/0185426 A1 | 8/2007 | Ambrosio et al. |
| 2007/0207179 A1 | 9/2007 | Andersen et al. |
| 2007/0208420 A1 | 9/2007 | Ameer et al. |
| 2007/0219585 A1 | 9/2007 | Cornet et al. |
| 2007/0233022 A1 | 10/2007 | Henley et al. |
| 2007/0260226 A1 | 11/2007 | Jaeb et al. |
| 2008/0009830 A1 | 1/2008 | Fujimoto et al. |
| 2008/0112998 A1 | 5/2008 | Wang |
| 2008/0208147 A1 | 8/2008 | Argenta et al. |
| 2008/0208171 A1 | 8/2008 | Argenta |
| 2009/0011486 A1 | 1/2009 | Bettinger et al. |
| 2009/0093565 A1 | 4/2009 | Yang et al. |
| 2009/0148945 A1 | 6/2009 | Ameer et al. |
| 2009/0187259 A1* | 7/2009 | Argenta et al. ............ 623/23.74 |
| 2009/0254120 A1 | 10/2009 | Argenta et al. |
| 2009/0325859 A1 | 12/2009 | Ameer et al. |
| 2011/0129436 A1 | 6/2011 | Pryor et al. |
| 2012/0215235 A1 | 8/2012 | Fogel |

FOREIGN PATENT DOCUMENTS

| | | |
|---|---|---|
| DE | 561757 | 10/1932 |
| DE | 847475 | 7/1949 |
| DE | 847475 | 6/1952 |
| DE | 1963258 | 6/1971 |
| DE | 2809828 | 9/1978 |
| DE | 3102674 | 9/1982 |
| DE | 3539533 | 5/1987 |
| DE | 4037931 | 5/1992 |
| DE | 4111122 | 4/1993 |
| DE | 29504378 | 9/1995 |
| DE | 19722075 | 10/1998 |
| DK | 64055 | 10/1945 |
| EP | 0117632 | 9/1984 |
| EP | 0274898 | 7/1988 |
| EP | 0424165 | 4/1991 |
| EP | 0485657 | 5/1992 |
| EP | 0547496 | 6/1993 |
| EP | 0620720 | 10/1994 |
| EP | 0620720 B1 | 10/1994 |
| EP | 0620720 B2 | 10/1994 |
| EP | 0688189 | 12/1995 |
| EP | 0777504 | 6/1997 |
| EP | 0853950 | 7/1998 |
| EP | 0880953 | 12/1998 |
| EP | 0688189 | 9/2000 |
| EP | 1064958 | 1/2001 |
| EP | 1088569 | 4/2001 |
| EP | 1452191 | 9/2004 |
| FR | 500253 | 3/1920 |
| FR | 1303238 | 9/1962 |
| GB | 190203090 | 6/1902 |
| GB | 114754 | 4/1918 |
| GB | 641061 | 8/1950 |
| GB | 1273342 | 5/1972 |
| GB | 1457164 | 12/1976 |
| GB | 1549756 | 8/1979 |
| GB | 2195255 | 4/1988 |
| GB | 2329127 | 3/1999 |
| GB | 2333965 | 8/1999 |
| GB | 2336546 | 10/1999 |
| GB | 2342584 | 4/2000 |
| GB | 2344531 | 6/2000 |
| GB | 2351025 | 12/2000 |
| JP | 1004629 | 1/1989 |
| JP | 06-048860 | 2/1994 |
| JP | H07116242 | 5/1995 |
| JP | 2003521962 | 7/2003 |
| JP | 2004305748 | 11/2004 |
| JP | 200534483 | 2/2005 |
| JP | 2008099565 | 5/2008 |
| RU | 2006114483 | 11/2007 |
| RU | 70627 | 2/2008 |
| SE | 84485 | 10/1935 |
| SU | 587941 | 1/1978 |
| SU | 1416108 | 7/1985 |
| SU | 1251912 | 8/1986 |
| SU | 1268175 | 11/1986 |
| WO | 80/01139 | 6/1980 |
| WO | 87/00439 | 1/1987 |
| WO | 87/04626 | 8/1987 |
| WO | WO 89/04158 | 5/1989 |
| WO | 90/00060 | 1/1990 |
| WO | 90/10424 | 9/1990 |
| WO | 9011795 | 10/1990 |
| WO | 9100718 | 1/1991 |
| WO | 9116030 | 10/1991 |
| WO | 9219313 | 11/1992 |
| WO | 9220299 | 11/1992 |
| WO | 93/09727 | 5/1993 |
| WO | 94/00090 | 1/1994 |
| WO | 94/20041 | 9/1994 |
| WO | 96/05873 | 2/1996 |
| WO | 96/15745 | 5/1996 |
| WO | 99/13793 | 3/1999 |
| WO | 99151164 | 10/1999 |
| WO | 00/07653 | 2/2000 |
| WO | 00/15277 | 3/2000 |
| WO | 00/21586 | 4/2000 |
| WO | 00/26100 | 5/2000 |
| WO | 00/30567 | 6/2000 |
| WO | 00/32247 | 6/2000 |
| WO | 00/38552 | 7/2000 |
| WO | 00/38755 | 7/2000 |
| WO | 00/42958 | 7/2000 |
| WO | 00/59418 | 10/2000 |
| WO | 00/59424 | 10/2000 |
| WO | 00/61206 | 10/2000 |
| WO | 00/64394 | 11/2000 |
| WO | 01/34223 | 5/2001 |
| WO | 01/37922 | 5/2001 |
| WO | 01/49233 | 7/2001 |
| WO | 01/85248 | 11/2001 |
| WO | WO 01/89431 | 11/2001 |
| WO | WO 02/043634 | 6/2002 |
| WO | 02092783 | 11/2002 |
| WO | 03/005943 | 1/2003 |
| WO | 03028786 | 4/2003 |
| WO | 03/101385 | 12/2003 |
| WO | WO 03/101508 | 12/2003 |
| WO | 2005/028017 | 3/2005 |
| WO | 2005/046762 | 5/2005 |
| WO | 2005/102234 | 11/2005 |
| WO | 2006/046060 | 5/2006 |
| WO | 2007106591 | 9/2007 |
| WO | 2008063281 | 5/2008 |
| WO | 2009/049058 | 4/2009 |
| WO | 2009/089435 | 7/2009 |
| WO | 2010009294 | 1/2010 |

OTHER PUBLICATIONS

Borquist, et al. "Measurements of wound edge microvascular blood flow during negative pressure wound therapy using thermodiffusion and transcutaneous and invasive laser Doppler velocimetry". Wound Repair Regen. Nov. 2011; 190: 727-33.*

(56) References Cited

OTHER PUBLICATIONS

Ulaschik, V.S., "Barotherapy", in Physical Therapy, Universal Medical Encyclopedia; pp. 85-86 and cover sheet (3 sheets in English, 3 sheets in Russian), (2008, allegedly gone to print Oct. 1, 2007).
Opposition to EP 2 392 302—Communication of Opponent Hartmann dated Nov. 12, 2013 and European Patent Office's Communication of a notice of opposition (and translation) dated Nov. 19, 2013.
Opposition to EP 2 392 302—Communication of Opponent KSNH dated Nov. 12, 2013 and European Patent Office's Communication of a notice of opposition dated Nov. 18, 2013.
Lindstedt, S., et al., "A compare between myocardial topical negative pressure levels of -25 mmHg and -50 mmHg in a porcine model", BMC Cardiovascular Disorders 2008 8:14, BioMed Central, pp. 1-7.
Lindstedt, S., et al., "Blood Flow Changes in Normal and Ischemic Myocardium During Topically Applied Negative Pressure", Ann Thorac Surgery 2007;84:568-73.
Labler, L., et al., "Wound conditioning by vacuum assisted closure (V.A.C.) in postoperative infections after dorsal spine surgery," Eur. Spine J., 15 (9): 1388-1396 (Sep. 2006).
Tauro, L.F., et al., "A comparative study of the efficacy of topical negative pressure moist dressings and conventional moist dressings in chronic wounds," Indian J. Plast. Surg. 40(2):133-140 (Jul.-Dec. 2007).
Durandy, Y., et al., "Mediastinal infection after cardiac operation", J. Thorac. Cardiovasc. Surg., 97:282-5, (1989).
Sartipy, U., et al., "Cardiac rupture during vacuum-assisted closure therapy," Ann. Thorac. Surg., 82:1110-1 (2006).
U.S. Appl. No. 13/094,233—Official action and Form 892 (Apr. 19, 2012).
Milner, R.H., et al., "Plasticized polyvinyl chloride film as a primary burns dressing: a microbiological study," Burns, 14(1):62-65 (1988).
Wilson, G., et al., "Plasticised polyvinylchloride as a temporary dressing for burns," Br. Med. J., 294:556-557 (Feb. 1987).
Hunsaker, R.H., Correspondence and Brief Communications—"Polyvinylchloride for increasing take of skin grafts," Plast. Reconstr. Surg. 82:193 (Jul. 1988).
Argenta, L.C., et al., "Vacuum-assisted closure: state of clinic art", Plast. Reconstr. Surg., 117 (7 Suppl.): 127S-142S (Jun. 2006).
Chung, C.J., et al., "Case review: management of life-threatening sepsis and wound healing in a Klippel-Trenaunay patient using serial surgical debridements and vacuum-assisted closure", Eur. J. Plast. Surg., 26:214-216 (2003).
Dedmond, B.T., et al., "Subatmospheric pressure dressings in the temporary treatment of soft tissue injuries associated with type III open tibial shaft fractures in children", J. Pediatr. Orthop., 26(6):728-732, (Nov.-Dec. 2006).
Dedmond, B.T., et al., "The use of negative-pressure wound therapy (NPWT) in the temporary treatment of soft tissue injuries associated with high-energy open tibial shaft fractures", J. Orthop. Trauma, 21(1):11-17, (Jan. 2007).
Gemeinhardt, K.D., et al., "Vacuum-assisted closure for management of a traumatic neck wound in a horse", Equine Veterinary Education, 17(1):27-32, (2005).
Laverty, D., et al., "Negative pressure wound therapy in the management of orthopedic wounds", Ostomy Wound Manage., 50(11A suppl):18S-9S (Nov. 2004).
Molnar, J.A., "Applications of negative pressure wound therapy to thermal injury", Ostomy Wound Manage., 50(4A suppl):17-9 (Apr. 2004).
Molnar, J.A., "The science behind negative pressure wound therapy", Ostomy Wound Manage., 50 (4A suppl):2-5 (Apr. 2004).
Molnar, J.A., et al., "Management of an acute thermal injury with subatmospheric pressure", J. Burns Wounds, 4:83-92, 4:e5 (published online Mar. 24, 2005).
Morykwas, M.J., et al., "Effects of varying levels of subatmospheric pressure on the rate of granulation tissue formation in experimental wounds in swine", Ann. Plast. Surg., 47(5):547-551 (Nov. 2001).

Plikaitis, C.M., et al., "Subatmospheric pressure wound therapy and the vacuum-assisted closure device: basic science and current clinical successes", Expert Rev. Med. Devices, 3(2):175-184, (Mar. 2006).
Schlatterer, D., et al., "Orthopedic indications for negative pressure wound therapy", Ostomy Wound Manage., 51 (2A suppl):27S-8S (Feb. 2005).
Schneider, A.M., et al., "Re: use of specialized bone screws for intermaxillary fixation: reply", Ann. Plast. Surg., 47 (1): 93, (Jul. 2001).
Webb, L.X., et al., "The contaminated high-energy open-fracture: a protocol to prevent and treat inflammatory mediator storm-induced soft-tissue compartment syndrome (IMSICS)", J. Am. Acad. Orthop. Surg., 14(10):SA82-S86 (Oct. 2006).
Yang, C.C., et al., "Vacuum-assisted closure for fasciotomy wounds following compartment syndrome of the leg", J. Surg. Orthop. Adv., 15(1):19-23 (Spring 2006).
Defranzo, A.J., et al., "Vacuum assisted closure of the abdominal wall", 73rd annual Meeting, American Association of Plastic Surgeons, Philadelphia, PA (2004), 1 sheet of abstract.
Argenta, L.C., et al., "The V.A.C. as an adjunct for treatment for abdominal wounds", 66th Annual Meeting of the American Society of Plastic and Reconstructive Surgeons, San Francisco, CA, pp. 330-331; 1 sheet of abstract (Sep. 21-24, 1997). WFU-39.
Argenta, L.C., et al., "Vacuum assisted closure of chronic wounds", 65th Annual Scientific Meeting, American Society of Plastic and Reconstructive Surgeons, Dallas, TX, pp. 226-227; 1 sheet of abstract (Nov. 9-13, 1996).
Defranzo, A.J., et al., "The use of V.A.C. therapy for treatment of lower extremity wounds with exposed bone", 68th Annual Meeting of the American Society of Plastic and Reconstructive Surgeons, New Orleans, LA, pp. 37-38; 2 sheets of abstract (Oct. 24-27, 1999). WFU-42.
Kortesis, B., et al., "Vacuum-assisted closure for the treatment of open tibia fractures", 72nd Annual Meeting of the American Society of Plastic Surgeons, San Diego, CA, pp. 172-173; 1 sheet of abstract (Oct. 25-29, 2003). WFU-41.
Kremers, L., et al., "Effect of topical sub-atmospheric pressure treatment on angiotensin I and II levels post burn", 35th Annual Meeting, Abstract printed in J. Burn Care Rehabilitation, p. S44, Abstract No. 3 American Burn Association, Miami, Florida (Apr. 1-4, 2003).
Kremers, L., et al., "Serum interleukin levels post burn with and without application of sub-atmospheric pressure", 35th Annual Meeting, Abstract printed in Burn Care Rehabilitation, p. S43, Abstract No. 2, American Burn Association, Miami, Florida, (Apr. 1-4, 2003). WFU-53.
Molnar, J.A., et al., "Improved skin graft adherence and vascularization of integra(R) using subatmospheric pressure—a laboratory study", Abstract printed in Burn Care & Rehabilitation, p. S111, Abstract No. 141; American Burn Meeting, 34th Annual Meeting, Chicago, IL, (Apr. 24-27, 2002). WFU-51.
Morykwas, M.J., et al., "Negative pressure treatment of burned extremities", 65th Annual Scientific Meeting, American Society of Plastic and Reconstructive Surgeons, Dallas, TX, pp. 86-87; 1 sheet of abstract (Nov. 9-13, 1996). WFU-36.
Morykwas, M.J., et al., "The effect of V.A.C.(TM) therapy on the length of stay, total charges and average daily charge for patients assigned to DRG 263: analysis of 13 consecutive quarters", presented in part at the 28th Annual Conference of the Wound, Ostomy, and Continence Nurses Society, Seattle, WA, (15 sheets) (Jun. 15-19, 1996).
Park, C.A., et al., "Outpatient use of Integra® and subatmospheric pressure in the management of wound and burn reconstruction", J. Burn Care Rehabil., 26(2 suppl.):S113, Chicago, IL, (May 10-13, 2005).
Schneider, A.M., et al., "Muscle flap survival after complete venous occlusion by application of a negative pressure device", 66th Annual Meeting of the American Society of Plastic and Reconstructive Surgeons, San Francisco, CA, pp. 300-302; 2 sheets of abstract (Sep. 21-24, 1997). WFU-38.
Schneider, A.M., et al., "Treatment of brown recluse spider bite wounds by external application of sub-atmospheric pressure", 68th

(56) References Cited

OTHER PUBLICATIONS

Annual Meeting of the American Society of Plastic and Reconstructive Surgeons, New Orleans, LA, p. 35; 1 sheet of abstract (Oct. 24-27, 1999).
Webb, L.X., "Use of negative pressure devices in highly contaminated, high energy wounds", Extremity War Injuries: State of the Art and Future Directions, AAOS/OTA Extremity War Injures Symposium, Jan. 24-27, 2006, [Abstract]. WFU-65.
Morykwas, M.J., "Basic Research and Animal Studies," Presentation at the European Topical Negative Pressure Meeting in Salsbury, England, (Jun. 2005). WFU-71.
3M™, Tegaderm Family of Transparent Dressings for Chronic Wounds, pp. 1-8 (2002). NPL-002.
Alper, Joseph C., et al., "The In Vitro Response of Fibroblasts to the Fluid that Accumulates Under a Vapor-Permeable Membrane". Journal of Investigative Dermatology, 84:513-515, 1985. NPL-013.
Alper, Joseph C., et al., "Use of the Vapor Permeable Membrane for Cutaneous Ulcers: Details of application and side effects", Journal of the American Academy of Dermatology, vol. 11, No. 5, Part I, Nov. 1984, pp. 858-866. (NPL-014).
Angermeier, Marla C., et al., "Vapor-Permeable Membrane Therapy for Ulcers of Osteomyelitis", J. Dermatol. Surg. Oncol,, 10:5, May 1984, pp. 384-388. NPL-016.
Bourke, et al., "Comparison Between Suction and Corrugated Drainage After Simple Mastectomy: A Report on Controlled Trial", Br. J. Surg., vol. 63, 1976, pp. 67-69. NPL-056.
ConstaVac™ Closed Wound Drainage System, Stryker Instruments, 2 pages. NPL-092.
Eaglstein, William H., "Experiences with Biosynthetic Dressings", Journal of the American Academy of Dermatology, vol. 12, No. 2, Part 2, Feb. 1985, pp. 434-440. NPL-129.
Falanga, Vincent, et al., "A Therapeutic Approach to Venous Ulcers", Journal of the American Academy of Dermatology, vol. 14, No. 5, Part 1, May 1986, pp. 777-784. NPL-147.
Friedman, S., et al., "Treatment of Dermabrasion Wounds with a Hydrocolloid Occlusive Dressing", Arch Dermatol, vol. 121, Dec. 1985, pp. 1486-1487. NPL-166.
Friedman, Stephen J., et al., "Management of Leg Ulcers with Hydrocolloid Occlusive Dressing", Arch. Dermatol., vol. 120, Oct. 1984, pp. 1329-1336.
Holland, K.T., et al., "A Comparison of the In Vivo Antibacterial Effects of OpSite, Tegaderm and Ensure dressings", Journal of Hospital Infection, 1985, 6, pp. 299-303. NPL-209
Jeter, Katherine F., et al., "Wound Dressings of the Nineties: Indications and Contraindications", Clinics in Podiatric Medicine and Surgery, vol. 8, No. 4, Oct. 1991, pp. 799-816. NPL-224.
Katz, Stuart, et al., "Semipermeable Occlusive Dressings", Arch Dermatol., vol. 122, Jan. 1986, pp. 58-62. NPL-231.
Lewis, R.T., "Knitted Polypropylene (Marlex) Mesh in the Repair of Incisional Hernias", The Canadian Journal of Surgery, vol. 27, No. 2, Mar. 1984, pp. 155-157. NPL-256.
Lower Extremity Ulcers, Chapter 9, pp. 47-57. NPL-259.
Microtek Medica, Inc. "The Microtek Complete Closed Wound Drainage System", 6 pages. NPL-285.
Rovee, David T., et al., "Effect of Local Wound Environment on Epidermal Healing", Dept. of Skin Biology, Johnson & Johnson Research, New Brunswick, NJ, pp. 159-181 (1972). NPL-348.
Satas, Donatas, "Handbook of Pressure-Sensitive Adhesive Technology", Silicone Release Coatings, Van Nostand Reinhold Company, 1982, pp. 384-403. NPL-355
Turner, T.D., "A Look at Wound Dressings", Health and Social Service Journal, May 4, 1979, pp. 529-531. NPL-405.
Turner, T.D., "Recent Advances in Wound Management Products", pp. 3-6. NPL-406.
Turner, T.D., "Semipermeable Films as Wound Dressings", Welsh School of Pharmacy, University of Wales, Great Britain (Jul. 31, 1984). NPL-407.
Turner, T.D., "The Development of Wound Management Products", Chronic Wound Care, pp. 31-46. NPL-408.
Turner, T.D., et al., "Wound Management Product Selection", Journal of Sterile Services Management, Apr. 1985, pp. 3-6. NPL-409.
Varghese, Mathew C., et al., "Local Environment of Chronic Wounds Under Synthetic Dressings", Arch. Dermatol, vol. 122, Jan. 1986, pp. 52-57.
Viljanto, J., "Cellstic: A Device for Wound Healing Studies in Man. Description of the Method", Journal of Surgical Research, 20, 1976, pp. 115-119. NPL-420.
Wagner, S.A., et al., "An individualized Plastic Intraoral Device for the Collection of Human Parotid Saliva", International Journal of Clinical Pharmacology, Therapy and Toxilogy, vol. 22, No. 5, 1984, pp. 236-239. NPL-425.
Wilson, John L., et al., "Loss of Blood Volume in Spinal Surgery with Use of Closed Wound Suction: An Experimental Study", Southern Medical Journal, Jul. 1968, pp. 761-763, read before the Section on Orthopaedic and Traumatic Surgery, Southern Medical Association, 61st Annual Meeting, Miami Beach, FL, (Nov. 13-16, 1967). NPL-437.
Winter, G.D., "Healing of Skin Wounds and the Influence of Dressings on the Repair Process", pp. 46-60 of "Surgical dressings and wound healing: proceedings of a symposium held on Jul. 7-8, 1970 at the University of Bradford," Crosby Lockwood for Bradford University Press, (1971). NPL-439.
Kohlman, P., et al., "Pouching Procedure to Collect Drainage From Around a Biliary Drainage Catheter", Ostomy/Wound Management, Nov./Dec. 1991, pp. 47-50, V. 37. NPL-240.
Alper, J., "Recent Advances in Moist Wound Healing", Southern Medical Journal, Nov. 1986, pp. 1398-1404, vol. 79, No. 11. NPL-011.
Reid, D., "Information on Cupping or Using Suction Cups on Wounds and for Healing Purposes", from Chines Herbal Medicine (2 pages). NPL-345.
Sheppard, M.D., "Sealed drainage of wounds," The Lancet, Jun. 14, 1952, pp. 1174-1176. NPL-410.
Putney, F., "The Use of Continuous Negative Pressure After Laryngectomy and Radical Neck Dissection", Surgery, Gynecology & Obstetrics, Aug. 1956, pp. 244-246. NPL-336.
Pleupump MK II, printouts from websites, www.xenamedical.se and www.landstinget.sormland.se, Aug. 14, 2001 (12 pages). NPL-332.
"Wound Suction; Better Drainage With Fewer Problems", Nursing75, October, pp. 52-55 (1975). NPL-447.
Grams Aspirator, et al., Grams Medical, catalog pages (3 pages) (prices as of Aug. 1991 and Sep. 1992). NPL-175.
Medela Dominant promotional literature (2 pages of photos) (labeled circa 1984-1985). NPL-274.
Engdahl, O., et al., "Quantification of Aspirated Air Volume Reduces Treatment Time in Pneumothorax", Eur Respir J., 1990, 3, pp. 649-652. NPL-140.
Usage Manual Pleurasug TDR (2 pages of diagrams with descriptions). NPL-412.
Spengler, M., et al., "Performance of Filtered Sump Wound Drainage Tubes", Surgery, Gynecology & Obstetricsq, Mar. 1982, pp. 333-336, vol. 154. NPL-384.
Hallstrom, B., et al., "Postoperative Course After Total Hip Arthroplasty: Wound Drainage Versus No Drainage", Orthopaedic Review, Jul. 1992, pp. 847-851. NPL-185.
Miles, W., et al., "A Method of Performing Abdominoperineal Excision for Carcinoma of the Rectum and of the Terminal Portion of the Pelvic Colon", The Lancet, Dec. 19, 1908, pp. 1812-1813. NPL-287.
Benjamin, P., "Faeculent Peritonitis: A Complication of Vacuum Drainage", Br. J. Surg., 1980, pp. 453-454, vol. 67. NPL-042.
Sagi, A., et al., "Burn Hazard From Cupping—An Ancient Universal Medication Still in Practice", Burns, 1988, pp. 323-325, vol. 14, No. 4. NPL-351.
Agrama, H., et al., "Functional Longevity of Intraperitoneal Drains", The American Journal of Surgery, Sep. 1976, pp. 418-421, vol. 132. NPL-009.
Magee, C., et al., "Potentiation of Wound Infection by Surgical Drains", The American Journal of Surgery, May 1976, pp. 547-549, vol. 131. NPL-264.
Birdsell, D., et al., "The Theoretically Ideal Donor Site Dressing",Annals of Plastic Surgery, Jun. 1979, pp. 535-537, vol. 2, No. 6. NPL-048.

(56) References Cited

OTHER PUBLICATIONS

Cruse, P., et al., "A Five-Year Prospective Study of 23,649 Surgical Wounds", Surgical Wounds/Cruse and Foord, Aug. 1973, pp. 206-210, vol. 107. NPL-105.
Aubrey, D., et al., "Treatment of the Perineal Wound After Proctectomy by Intermittent Irrigation", Arch. Surg., Oct. 1984, pp. 1141-1144, vol. 119. NPL-021.
Mayo, C., "The One-Stage Combined Abdominoperineal Resection for Carcinoma of the Rectum, Rectosigmoid and Sigmoid", Surgical Clinics of North America, Aug. 1939, pp. 1011-1019. NPL-268.
Draper, J., "Make the dressing fit the wound", Nursing Times, Oct. 9, 1985, pp. 32-35. NPL-122.
Schumann, D., et al., "Preoperative Measures to Promote Wound Healing", Nursing Clinics of North America, Dec. 1979, pp. 683-699, vol. 14, No. 4. NPL-361.
Besst, J., et al., "Wound Healing—Intraoperative Factors", Nursing Clinics of North America, Dec. 1979, pp. 701-712, vol. 14, No. 4. NPL-044.
Cooper, D., et al., "Postsurgical Nursing Intervention as an Adjunct to Wound Healing", Nursing Clinics of North America, Dec. 1979, pp. 713-726, Nursing Clinics of North America, vol. 14, No. 4. NPL-097.
O'Byrne, C., "Clinical Detection and Management of Postoperative Wound Sepsis", Nursing Clinics of North America, Dec. 1979, pp. 727-741, vol. 14, No. 4. NPL-316.
Keith, C., "Would Management Following Head and Neck Surgery", Nursing Clinics of North America, Dec. 1979, pp. 761-778, vol. 14, No. 4. NPL-233.
Tenta, L., et al., "Suction Drainage of Wounds of the Head and Neck", Surgery, Gynecology. & Obstetrics, Dec. 1989, p. 558, vol. 169. NPL-401.
Firlit, C., et al., "Surgical Wound Drainage: A Simple Device for Collection", journal of Urology, Aug. 1972, pp. 327, vol. 108. NPL-153.
Moloney, G., "Apposition and Drainage of Large Skin Flaps", Oxford, England, pp. 173-179 (Feb. 1957). NPL-296.
Worth, M., et al., "The Effectiveness of Bacterial Filtration in Vented Wound Drains", Journal of Surgical Research, 1979, pp. 405-407, 27. NPL-446.
Flynn, M., et al., "Promoting Wound Healing: Wound Healing Mechanisms", American Journal of Nursing, Oct. 1982, pp. 1544-1558. NPL-162.
Miles, W., "Technique of the Radical Operation for Cancer of the Rectum", The British Journal of Surgery, 1914-1915, pp. 292-305. NPL-286.
Hilton, P., "Surgical Wound Drainage: A Survey of Practices Among Gynaecologists in the British Isles", British Journal of Obstetrics and Gynaecology, Oct. 1988, pp. 1063-1069, vol. 95. NPL-207.
Milsom, I., et al., "An Evaluation of a Post-Operative Vacuum Drainage System", Current Medical Research and Opinion, 1979, pp. 160-164, vol. 6, No. 2. NPL-289.
Fox, J., et al., "The Use of Drains in Subcutaneous Surgical Procedures", The American Journal of Surgery, Nov. 1976, pp. 673-674, vol. 132.
Hilsabeck, J., "The Presacral Space as a Collector of Fluid Accumulations Following Rectal Anastomosis", American Society of Colon and Rectal Surgeons, (Oct. 1982), pp. 680-684, vol. 25, No. 7.
Hulten, L., et al., "Primary Closure of Perineal Wound After Protocolectomy or Rectal Excision", Acta Chir Scand 137, 1971, pp. 467-469.
Landes, R., "An Improved Suction Device for Draining Wounds", Arch. Surg., May 1972, pp. 707, vol. 104.
Hugh, T., "Abdominal Wound Drainage", The Medical Journal of Australia, May 4, 1987, pp. 505.
Eisenbud, D., "Modern Wound Management", Adadem Publishing, pp. 109-116 (Jan. 1999).
Eaglstein, W., et al., "Wound Dressings: Current and Future", Clinical and Experimental Approaches to Dermal and Epidermal Repair; Normal and Chronic Wounds, Progress in Clinical and Biological Research, vol. 365, © 1991 Wiley-Liss, Inc., pp. 257-265.

Bruno, P., "The Nature of Wound Healing", Nursing Clinics of North America, Dec. 1979, pp. 667-682, vol. 14, No. 4.
Bar-El, Y., et al., "Potentially Dangerous Negative Intrapleural Pressures Generated by Ordinary Pleural Drainage Systems", Chest, Feb. 2001, pp. 511-514, vol. 119, No. 2.
Agarwala, S., et al., "Use of Mini-Vacuum Drains in Small Surgical Wounds", Plastic and Reconstructive Surgery, Apr. 1998, pp. 1421-1422, vol. 101, n. 5.
Nasser, A., "The Use of the Mini-Flap Wound Suction Drain in Maxillofacial Surgery", Annals of the Royal College of Surgeons of England, 1986, pp. 151-153, vol. 68.
Hunt, T.K., et al. eds., "Dead Space" and "Drainage", Fundamentals of Wound Management, pp. 416-447 (1979).
Lumley, J., et al., "The Physical and bacteriological Properties of Disposable and Non-Disposable Suction Drainage Units in the Laboratory", Br. J. Surg, 1974, pp. 832-837, vol. 61.
Britton, B., et al., "A Comparison Between Disposable and Non-disposable Suction Drainage Units: A Report of a Controlled Trial", Br. J. Surg., 1979, pp. 279-280, vol. 66.
McFarlane, R., "The use of Continuous Suction Under Skin Flaps", British Journal of Plastic Surgery, pp. 77-86 (1958-1959).
Fay, M., "Drainage Systems: Their Role in Wound Healing", AORN Journal, Sep. 1987, pp. 442-455, vol. 46, No. 3.
Taylor, V., "Meeting the Challenge of Fistulas & Draining Wounds", Nursing80, June, pp. 45-51.
Orgill, D., "Curent Concepts and Approaches to Would Healing", Critical Care Medicine, Sep. 1988, pp. 899-908, vol. 16, No. 9.
Part III. Resolving Selected Clinical Dilemmas, pp. 17-20.
"Making Sense of Wound Drainage", Nursing Times, Jul. 5, 1989, pp. 40-42, vol. 85, No. 27.
Manualectric Breastpump, Catalog pages (4 pages), diagrams and descriptions.
Harkiss, K., "Leg Ulcers Cheaper in the Long Run", Community Outlook, Aug. 1985, pp. 19, 21, 22, 24 & 26.
Westaby, S. (Editor), "Wound Care No. 43; Which Dressing and Why", Nursing Times Jul. 21, 1982, pp. 41-44.
OpSite Wound Dressings, "Do Your Pressure Sore Dressings Shape Up to the OpSite Standard", 2 pages of advertisements.
Dow Corning Silastic® Foam Dressing: A New Concept in the Management of Open Granulating Wounds, 2 pages of advertisements.
Cobb, J., "Why Use Drains", The Journal of Bone and Joint Surgery, Nov. 1990, pp. 993-995, vol. 72-B, No. 6.
Pleur$_x$ Pleural Catheter, Denver Biomedical, 4 pages of brochure.
Silvis, R., et al., "The Use of Continuous Suction Negative Pressure Instead of Pressure Dressing", Annals of Surgery, Aug. 1955, pp. 252-256, vol. 142, No. 2.
Van Way, C., "Prevention of Suction-Induced Gastric Mucosal Damage in Dogs", Gastric Suction, 1987, pp. 774-777, vol. 15, No. 8.
Moserova, J., "The Healing and Treatment of Skin Defects", pp. 103-151 (1989).
Rabkin, J., et al., "Infection and Oxygen", Problem Wounds: The Role of Oxygen, pp. 1-15 (1987).
Paradise Valley Hospital, The Center for Wound Healing and Hyperbaric Medicine, 3 pages of brochure.
DuoDERM Hydroactive™ Dressing, "In wound management—Now, a proven environment for fast healing", 1 page advertisement.
Howmedica porto-vac®, "Gentle, Steady Wound Drainage", 1 page advertisement.
Silicone from CUI (Cox-Uphoff International), "Flexability", 1 page advertisement.
Curtin, L., "Wound Management: Care and Cost—An Overview", Nursing Management, Feb. 1984, pp. 22-25, vol. 15.
Grabowski, S., "Leczenie ran z zastosowaniem podcisnienia", article, pp. 19-21, English abstract on p. 21 and 1 sheet printout from PubMed, (Jan. 1, 1964).
Royle, G., et al., "Disposable Drains", Annals of the Royal College of Surgery of England, 1984, 1 page, vol. 66.
Meehan, P., "Open Abdominal Wounds: A Creative Approach to a Challenging Problem", Pregressions, 1992, pp. 3-8, 11, vol. 4, No. 2.
Stansby, G., et al., "Vacuum Drainage of Groin Wounds After Vascular Surgery", Br. J. Surg., Oct. 1990, pp. 1194-1195, vol. 77, No. 10.

(56) References Cited

OTHER PUBLICATIONS

Edlich, R., et al., "Evaluation of a New, Improved Surgical Drainage System", The American Journal of Surgery, Feb. 1985, pp. 295-298, vol. 149.
Broader, J., et al., "Management of the Pelvic Space After Proctectomy", Br. J. Surg., 1974, pp. 94-97, vol. 61.
Ayoub, M., et al., "A study of cutaneous and intracompartmental limb pressures associated with the combined use of tourniquets and plaster casts", May 1986, pp. 497, vol. 68-B, No. 3.
Cooper, D., "Optimizing Wound Healing: A Practice Within Nursing's Domain", Nursing Clinics of North America, Mar. 1990, pp. 165-180, vol. 25, No. 1.
Cooper, D., "Wound Healing", Nursing Clinics of North America, pp. 163-164 (Mar. 1990).
Hollis, H., et al., "A Practical Approach to Wound Care in Patients With Complex Enterocutaneous Fistulas", Surgery, Gynecology & Obstetrics, Aug. 1985, pp. 178-180, vol. 161.
Fingerhut, A., "Passive vs. Closed Suction Drainage After Perineal Would Closure Following Abdominoperineal Rectal Excision for Carcinoma", Dis Colon Rectum, Sep. 1995, pp. 926-932, vol. 38, No. 9.
Cook Pneumothorax Catheter Set, Wayne Pneumothorax Catheter Set, Emergency Medicine, Videotape advertisement.
Schaffer, D., "Closed Suction", Nursing97, Nov., http://www.springnet.com, pp. 62-64.
Carroll, P., "The Principles of Vacuum and Its Use in the Hospital Environment", Ohmeda, pp. 1-30 and cover sheet.
Ramnarine, I.R., et al., "Vacuum-assisted closure in the paediatric patient with post-cardiotomy mediastinitis", Eur. J. Cardiothorac. Surg., 22:1029-31 (Dec. 2002).
Rollins, H., "Hypergranulation tissue at gastrostomy sites", J. Wound Care, 9(3):127-129 (Mar. 2000).
Schaum, K.D., "Medicare Part B negative pressure wound therapy pump policy. A partner for Medicare Part A PPS," Home Healthc. Nurse, 20(1):57-8 (Jan. 2002).
Shaer, W.D., "Inexpensive vacuum-assisted closure employing a conventional disposable closed-suction drainage system", Plast. Reconstr. Surg., 107(1):292-3 (Jan. 2001).
Saklani, A.P., et al., "Vacuum assisted closure system in the management of enterocutaneous fistula", Poslgrad. Med. J., 78(925):699 (Nov. 2002).
Takei, T., et al., "Molecular basis for tissue expansion: clinical implications for the surgeon", Plast. Reconstr. Surg., 102(1):247-258 (Jul. 1998).
Tang, A.T.M., et al., "Vacuum-assisted closure to treat deep sternal wound infection following cardiac surgery", J. Wound Care, 9(5):229-30 (May 2000).
Nikkhah, C., et al., "Re: use of specialized bone screws for intermaxillary fixation", Ann. Plast. Surg., 47(1): 93, (Jul. 2001).
Voinchet, V., et al., "Vacuum assisted closure. Wound healing by negative pressure", Ann. Chir. Plast. Esthet., (English abstract on first page, and 1 sheet printout from PubMed); 41(5):583-9, (Oct. 1996).
Von Gossler, C.M., et al., "Rapid aggressive soft-tissue necrosis after beetle bite can be treated by radical necrectomy and vacuum suction-assisted closure", J. Cutan. Med. Surg., 4(4):219-222 (Oct. 2000).
Wilhelmi, B.J., et al., "Creep vs. stretch: a review of the viscoelastic properties of skin", Ann. Plast. Surg., 41 (2):215-219, (Aug. 1998).
Wiseman, J., et al., "Aesthetic aspects of neurofibromatosis reconstruction with the vacuum-assisted closure system", Aesth. Plast. Surg., 25:326-31 (Sep.-Oct. 2001).
Young, T., "Common problems in wound care: overgranulation", Br. J. Nursing, 4(3):169-170, (Feb. 9-22, 1995).
Ziegler, U.E., et al., "Skin substitutes in chronic wounds", Zentralbl. Chir., (English abstract on first page; 1 sheet printout from PubMed); 126 Suppl 1:71-4 (2001).
Stannard, J., "Complex orthopaedic wounds: prevention and treatment with negative pressure wound therapy", Orthop. Nurs., 23 Suppl 1:3-10 (10 sheets) (Mar.-Apr. 2004), presented at the 17th Annual Clinical Symposium on Advances in Skin & Wound Care, Dallas, TX (Sep. 23, 2002).
Patel, C.T.C., et al., "Vacuum-assisted wound closure: changing atmospheric pressure assists wound healing," AJN, 100:45-47 (2000).
Masters, J., "Reliable, inexpensive and simple suction dressings", Letters to the Editor, p. 267, labeled 1998.
Hazelbag, S., et al., "Cytokine profile of cervical cancer cells", Gynecol. Oncol., 83(2):235-243, (Nov. 2001).
Beitz, J.M., et al., "Abdominal wound with enterocutaneous fistula: a case study", J. Wound Ostomy Continence Nurs., 25(2):102-6, (Mar. 1998).
Baxandall, T., "Healing cavity wounds with negative pressure", Elderly Care, 9(1):20, 22 (Feb.-Mar. 1997).
McKinney, P.E., "Out-of-hospital and interhospital management of crotaline snakebite", Ann. Emerg. Med., 37 (2):168-174, (Feb. 2001).
Leroy, S.C., et al., "Severe penile erosion after use of a vacuum suction device for management of erectile dysfunction in a spinal cord injured patient. Case report", Paraplegia, 32(2):120-123 (Feb. 1994).
Morykwas, M.J., et al., "Use of Negative Pressure to Increase the Rate of Granulation Tissue Formation in Chronic Open Wounds", The FASEB Journal, (799-800), Feb. 19, 1993.
Orringer, J.S., et al., "Management of Wounds in Patients with Complex Enterocutaneous Fistulas", Surgery, Gynecology & Obstetrics, Jul. 1987, vol. 165.
Swearingen, P.L., "The Addison-Wesley Photo-Atlas of Nursing Procedures", 9 pages, © 1984.
Mulder, G.D, et al., Clinicians' Pocket Guide to Chronic Wound Repair, Wound Healing Publications Second Edition, 1992, pp. 1-107.
Peacock, E.E., Jr., Wound Repair:, Repair of Skin Wounds, 1984, pp. 172-175.
Murray, J., et al., "On the Local and General Influence on the Body if Increased and Diminished Atmospheric Pressure", The Lancet, V. 1, 1834-1835, pp. 909-917.
Herrmann, L., et al., "The Conservative Treatment of Arteriosclerotic Peripheral Vascular Diseases", pp. 750-760 (Oct. 1934).
Versatile 1 Wound Vacuum System™ for The Promotion of Wound Healing, Wound Application instructions, 1 page advertisement.
Bluesky Medical "The Versatile One!™", Wound Drainage and More, 1 page advertisement. (Labeled Spring 2003).
CHARIKER-JETER® Wound Sealing Kit, Would Application Instructions, 1 page advertisement.
Davies, J.W.L, "Synthetic materials for covering burn wounds: Progress towards perfection. Part I. Short term dressing materials", Burns, Nov. 1983;10(2), 94-103.
Lamke, L.O., et al., "The evaporative water loss from burns and the water-vapour permeability of grafts and artificial membranes used in the treatment of burns", Burns, 3, 159-165, 1977.
Barnett, A., et al., "Comparison of Synthetic Adhesive Moisture Vapor Permeable and Fine Mesh Gauze Dressings for Split-Thickness Skin Graft Donor Sites", The American Journal of Surgery, vol. 145, Mar. 1983, pp. 379-381.
Alper, J., et. al., "Moist wound healing under a vapor permeable membrane", Journal of the American Academy of Dermatology, vol. 8, No. 3, Mar. 1983, pp. 347-353.
James, J.H., et. al., "The use of Opsite, A Vapour Permeable Dressing, on Skin Donor Sites", British Journal of Plastic Surgery (1975), 28, 107-110.
Nahas, L.F., et al., "Use of Semipermeable Polyurethane Membrane for Skin Graft Dressings", Plastic and Reconstructive Surgery, Jun. 1981, pp. 791-792.
Edlich, R.F., et al., "Surgical Devices in Wound Healing Management", Wound Healing Biochemical & Clinical Aspects, W.B. Saunders Company, © 1992, pp. 581-599.
Orr, RK, et al., "Early Discharge After Mastectomy. A Safe Way of Diminishing Hospital Cost", Am Surg. Mar. 1987; 53(3) Abstract.
Otolaryngology, Head and Neck Surgery, The C.V. Mosby Company, © 1986, pp. 1716, 1724 and 2521.
Otolaryngology, Volume III, Head and Neck, W.B. Saunders Company, © 1980, pp. 2963.
Lore, Jr., J.M., "An Atlas of Head and Neck Surgery", Second Edition, vol. II, W.B. Saunders Company, Ó 1973.

(56) References Cited

OTHER PUBLICATIONS

Johnson, Frank E., "An Improved Technique for Skin Graft Placement Using a Suction Drain", pp. 585-586 (Dec. 1984).
Dewan, P.A., et al., "An Alternative Approach to Skin Graft Donor Site Dressing", Aust. N.Z. J. Surg. 1986, 56, 509-510.
Svedman, P., "A dressing allowing continuous treatment of a biosurface," IRCS Medical Science: Biomedical Technology; Clinical Medicine; Surgery and Transplantation, 7:221 (1979). (Exhibit D-407).
Davydov, Y., et al., "Bacteriological and Cytological Assessment of Vacuum Therapy of Purulent Wounds," Vestn. Khir., 48-52, English translation by IRC, (Oct. 1988). (Exhibit D-290).
Davydov, Y., et al., "Vacuum Therapy in the Treatment of Purulent Lactation Mastitis," Vestn. Khir. P. 66-70, English translation by IRC, (Sep. 1986), (Exhibit D-292).
Meyer, W., et al., "Bier's Hyperemic Treatment," W.B. Saunders & Co., 1908 (Exhibit D246).
Chariker/Jeter/Tintle Slides "Closed Wound Suction" by Dr. Mark Chariker et al., 41 sheets, pp. 1-10, 19, 55-84 (D-041) (allegedly dated 1985 and 1986).
Jeter, K., list of publications, 4 sheets, (D-161).
Svedman, P., et al., "Staphylococcal wound infection in the pig: Part I. Course," Ann. Plast. Surg., 23(3):212-218, (Sep. 1989).
Sanden, G., et al., "Staphylococcal wound infection in the pig: Part II. Inoculation, quanitification of bacteria, and reproducibility," Ann. Plast. Surg., 23(3):219-223, (Sep. 1989).
Banwell, P, et al., "Topical Negative Pressure TNP Focus Group Meeting", Proceedings, London, UK 2003, pp. 1-111.
Proceedings from the 2003 National V.A.C.® Education Conference, supplement to the Apr. 2004 Wounds, 40 pages.
Dieu, T., et al., "Too Much Vacuum-Assisted Closure", ANZ J. Surg. 2003; 73: 1057-1060.
Chester, D., et al., "Adverse Alteration of Wound Flora with Topical Negative-Pressure Therapy: A Case Report", British Journal of Plastic Surgery, 2002, pp. 510-511.
Alvarez, A., et al., "Vacuum-Assisted Closure for Cutaneous Gastrointestinal Fistula Management", Gynecologic Oncology, 80, 413-416 (2001).
Nienhuijs, S.W., et al., "Can Topical Negative Pressure Be Used to Control Complex Enterocutaneous Fistulae?", Journal of Wound Care, V. 12, No. 9, Oct. 2003, pp. 343-345.
Erdmann, D., et al., "Abdominal Wall Defect and Enterocutaneous Fistula Treatment with the Vacuum-Assisted Closure (V.A.C.) System", Plastic and Reconstructive Surgery, vol. 108, No. 7, pp. 2066-2068 (Dec. 2001).
Lohman, R., et al., "Discussion: Vacuum Assisted Closure: Microdeformations of Wounds and Cell Proliferation", Plastic and Reconstructive Surgery, Oct. 2004, pp. 1097-1098.
Defranzo, A.J., et al., "109: Use of Sub-Atmospheric Pressure for Treatment of Gunshot Injuries", Plastic Surgical Forum, V. XXIII, Los Angeles, CA, Oct. 14-18, 2000, pp. 180-181.
Marks, M., et al., "Management of Complex Soft Tissue Defects in Pediatric Patients Using the V.A.C. Wound Closure", Plastic Surgical Forum, V. XXI, Boston, MA, Oct. 3-7, 1998, pp. 215-216.
Morykwas, M. and Argenta, L., "Use of Negative Pressure to Prevent Progression of Partial Thickness Burns", American Burn Association, V. 26, 26th Annual Meeting, Apr. 20-23, 1994, Orlando, Florida, pp. 157.
Morykwas, M. and Argenta, L., "Vacuum Assisted Closure (VAC Therapy) for Secondary Closure of Dehisced and Infected Wounds", Wound Repair and Regeneration, Jul.-Sep. 1995, pp. 361.
Morykwas, M. and Argenta, L., "Treatment of Burned Extremities Using Vacuum Therapy (The V.A.C.)", Wound Repair and Regeneration, V. 3, N. 3, Jul.-Sep. 1995, pp. 367.
Webb, L. and Morykwas, M., et al., "The Use of Vacuum-Assisted Closure in Composite Wound Management", The Third Riva Congress, Current Perspectives in Fracture Management and Orthopaedic Reconstruction, May 10-14, 2000, Italy, pp. 137.
Morykwas, M. and Webb, L., "Sub-Atmospheric Pressure for the Treatment of Lower Extremity Wounds", The Third Riva Congress, Current Perspectives in Fracture Management and Orthopaedic Reconstruction, May 10-14, 2000, Italy, pp. 135-136.
Argenta, L., et al., "Use of V.A.C. for Treatment of Dehisced Sternal Incisions", Plastic Surgical Forum, V. XXIII, Los Angeles, CA, Oct. 14-18, 2000, pp. 172-174.
Morykwas, M., et al., "Isolated Muscle Flap Survival with Complete Venous Occlusion: Varying Delay in External Application of Subatmospheric Pressure", Plastic Surgical Forum, V. XXI, Boston, MA, Oct. 3-7, 1998, pp. 237.
Morykwas, M. and Argenta, L., "V.A.C. Experience and Difficult Wounds", des Journees Regionales des Plaies et Cicatrisations, Sep. 22-23, 1997, pp. 76-90.
Morykwas, M. and Argenta, L., "Use of the V.A.C.™ For Treatment of a Traumatic Left Hip Disarticulation",ACA-Acta Chir. Austriaca, Supplement Nr. 150, 1998, pp. 24-25 and cover sheet.
Banwell, P., et al., "Application of Topical Sub-Atmospheric Pressure Modulates Inflammatory Cell Extravasation in Experimental Partial Thickness Burns", Wound Repair and Regeneration, Jul./Aug. 1999, V. 7, N. 4, pp. A286-287.
Banwell, P., et al., "Dermal Perfusion in Experimental Partial Thickness Burns: The Effect of Topical Subatmospheric Pressure", Jan./Feb. 2000, V. 21, N. 1, Part 2, Burn Care & Rehabilitation.
Morykwas, M., et al., "The Effect of Externally Applied Subatmospheric Pressure on Serum Myoglobin Levels After a Prolonged Crused/Ischemia Injury", The Journal of TRAUMA Injury, Infection and Critical Care, Sep. 2002, V. 53, N.3, pp. 537-540.
Molnar, J., et al., "Acceleration of Integra Incorporation in Complex Tissue Defects with Subatmospheric Pressure", Plastic and Reconstructive Surgery, Apr. 15, 2004, pp. 1339-1346.
Defranzo, A.J., et al., "The Use of Vacuum-Assisted Closure Therapy for the Treatment of Lower-Extremity Wounds with Exposed Bone", Plastic and Reconstructive Surgery, Oct. 2001, V. 108, N. 5, pp. 1184-1191.
Morykwas, M., "The Use of The V.A.C. Wound Treatment System for Acute and Subacute Wounds", Plaies & Cicatrices, Would Closure Healing, Apr. 21, 22 and 23, 1999.
Webb, L., et al., "Negative Pressure Wound Therapy in the Management of Orthopedic Wounds", Ostomy Wound Management, Apr. 2004, V. 50, Issue 4A (Suppl), pp. 26-27 and cover sheet.
Webb, L., et al., "Wound Management With Vacuum Therapy", English abstract from website printout and German article, http://www.ncbi_nlm_nih.gov/entrez/query.fcgi?cmd=Retrieve_&db=pubmed&dot=Abstra . . . , Dec. 2, 2004, 2 pages website printout, German article, Oct. 2001, pp. 918-926.
Webb, "New Techniques in Wound Management: Vacuum-Assisted Wound Closure", Journal of the American Academy of Orthopaedic Surgeons, V. 10, N. 5, Sep./Oct. 2002, pp. 303-311.
Morykwas, M. and Argenta, L., "Sub-Atmospheric Pressure Wound Treatment and Cultured Keratinocyte Allografts", Cultured Human Keratinocytes and Tissue Engineered Skin Substitutes, © 2001 Georg Thieme Verlag, pp. 343-346.
Molnar, J., et al., "Single-Stage Approach to Skin Grafting the Exposed Skull", Plastic and Reconstructive Surgery, Jan. 2000, V. 105, N. 1, 174-177.
Scherer, L, et al., "The Vacuum Assisted Closure Device: A Method of Securing Skin Grafts and Improving Graft Surival", Arch. Surg., V. 137, Aug. 2002, pp. 930-934.
Miller, P., et al., "Late Fascial Closure in Lieu of Ventral Hernia: The Next Step in Open Abdomen Management", the Journal of TRAUMA Injury, Infection and Critical Care, Nov. 2002, V. 53, N. 5, pp. 843-849.
Betancourt, S., "A Method of Collecting the Effluent From Complicated Fistula of the Small Intestine", 1986, p. 375.
Dorland's Illustrated Medical Dictionary , Twenty-Fifth Edition, 1974, pp. 1112.
Hopf, H., et al., "Adjuncts to preparing wounds for closure Hyperbaric oxygen, growth factors, skin substitutes, negative pressure wound therapy (vacuum-assisted closure)", Foot Ankle Clin N Am 6, 2001, pp. 661-682.
CHARIKER-JETER® Wound Drainage Kit, BlueSky Medical, 2 page advertisement with copy of business card from Quality Medical Supply.

(56) References Cited

OTHER PUBLICATIONS

CHARIKER-JETER® Wound Drainage Kit Instructions, Item #500. 7777, BlueSky Medical, 2 pages.
WOODING-SCOTT® Wound Drainage Kit Contents, Item #500. 8888, 1 page.
Montgomery, B., "Easy Dressing of Large, Draining Abdominal Wounds Using Moisture Vapor-Permeable Film", pp. 417-418, Techniques for Surgeons, Wiley Medical Publication, © 1985.
Herrmann, L., et al., "The Pavaex (Passive Vascular Exercise) Treatment of Obliterative Arterial Diseases of the Extremeties", The Journal of Medicine, Dec. 1933, pp. 524-529.
Herrmann, L., et al., "Passive Vascular Exercises: Treatment of Peripheral Obliterative Arterial Diseases by Rhythmic Alternation of Environmental Pressure", Archives of Surgery, v. 29, n. 5, Nov. 1934, pp. 697-704.
Sturr, R., Evaluation of Treatment of Peripheral Vascular Disease by Alternating Positive and Negative Pressure, Philadelphia, Archives of Physical Therapy, Sep. 1938, pp. 539-543.
Balin, A., et al., "Oxygen Modulates Growth of Human Cells at Physiologic Partial Pressures", Laboratory for Investigative Dermatology, J. Exp. Med.©, the Rockefeller University Press, v. 160, Jul. 1984, pp. 152-166.
Saran Resins and Films, "Fresh Thinking". website printout, 6 pages, Jan. 20, 2004.
BlueSky Medical, "A Leader in Suction Technology—Wound Drainage Experts", printout of website, 55 pages, Apr. 8, 2003, www.blueskymedical.com.
Davydov, et al., "Would Healing Under the Conditions of Vacuum Draining", Khirurgiia (Mosk). 1992, (7-8): 21-6 (with English translation by Scientific Translation Services). DV14.
Coyle, M., et al., "A Case Study: Positive Outcomes to Negative Pressure Wound Therapy—A collaborative assessment", Hospital of Saint Raphael, 1 page chart.
Nemoto, H., et al., "Stories From the Bedside: Purple Urine Bage Syndrome Development in Ileal Conduit", WVET, Journal 23(2), pp. 31-34.
Baker, B., "Negative-Pressure Therapy Looks Promising", Skin & Allergy News, Feb. 2000, p. 14.
McCallon, S., et al., "Vacuum-Assisted Closure versus Saline-Moistened Gauze in the Healing of Postoperative Diabetic Foot Wounds", Ostomy Wound Management, Aug. 2000, v.46, Issue 8.pp. 28-29, 31-32, 34.
Thomas, S., et al., "Comparative Review of the Properties of Six Semipermeable Film Dressings", The Pharmaceutical Journal, Jun. 18, 1988, pp. 785-789.
Baker, B., "Abundance of Web Sites on Wound Care Management", Family Practice News, Mar. 1, 2000, p. 52.
Cosker, T., et al., "Choice of Dressing Has a Major Impact on Blistering and Healing Outcomes in Orthopaedic Patients", Journal of Wound Care, Vo. 14, No. 1, Jan. 2005, pp. 27-29.
Townsend, P.L.G., "The Quest for a Cheap and Painless Donor-Site Dressing", Burns, 2, pp. 82-85 (Jan. 1976).
Langworthy, M., et al., "Treatment of the Mangled Lower Extremity After a Terrorist Blast Injury", Clinical Orthopaedics and Related Research, No. 422, pp. 88-96 (May 2004).
Park, G.B., et al., "The Design and Evaluation of a Burn Wound Covering", Supplied by the British Library—"The Word's Knowledge", pp. 11-15 (1978).
ACU-derm® Transparent Moisture Vapor Permeable Polyurethane Dressing, pp. 1-13 and cover sheet.
3M Ioban 2, Breathability, Conformability and Strength, Breathability—Moisture Vapor Transmission Rate and Conformability and Strength—Tensile Strength, Elongation and Fn Modulus Test (1 page).
smith&nephew website printout, Would Management, FAQs.
"Moist Wound Dressings" from Physicians Instruction Book for Moist Wound Healing.
Spahn, J.G., "Soft tissue challenges in the head and neck region,"Clinical Seminar Handout, EHOB, (46 pages).

Mendez-Eastman, S., "Guidelines for using negative pressure wound therapy", Adv. Skin Wound Care, 14 (6):314-323. (16 pp.) (Nov.-Dec. 2001).
Addition to the "Users Manual Concerning Overflow Protection-Concerns all Egnell Pumps", dated Feb. 3, 1983, 1 page Swedish, [1 page English].
Aeros, "Moblvac,""introducing the 'off the wall' vacuum system,"Aeros Instruments, Life Support Nursing, 3(1):34-37, Barlin Publishing Ltd. (Jan.-Feb. 1980).
Article in Russian, pp. 84-85.
Austad, E.D., et al., "Tissue expansion: dividend or loan?"Plast. Reconstr. Surg.,78(1):63-67 (Jul. 1986).
BlueSky Medical, 2 sheets of advertisement, "Introducing the Chariker-Jeter wound drainage kit" and "Introducing the Kremlin® wound drainage kit".
Egnell Minor, Instruction Book, First Addition [Edition], allegedly dated Feb. 1987, 21 pages Swedish, 3 pages English.
Feierabend, T.C., et al., "Injuries causing major loss of scalp", Plast. Reconstr. Surg., [Abstract only—1 pp. printout from PubMed], 76(2):189-194 (Aug. 1985).
Geronemus, R.G., et al., "The effect of two new dressings on epidermal wound healing", J. Dermatol. Surg. Oncol., 8(10):850-852 (Oct. 1982).
Miller, S.H., et al., "An inexpensive wound suction device", Surg. Gyencol. Obstet., 141(5):768 (Nov. 1975).
Miller, S.J., "Surgical wound drainage system using silicone tubing", J. Am. Podiatry Assn., 71(6): pp. 287-296, (Jun. 1981).
Nelson, R.P., et al., "Use of negative pressure suction in urology", Urology, 4(5):574-576, (Nov. 1974).
Svedman, "Irrigation Treatment of Leg Ulcers", The Lancet, Sep. 3, 1983, pp. 532-534.
Stewart, A., et al., "Cleaning v. healing," Community Outlook, pp. 22, 24 & 26 (Aug. 14, 1985).
Trammell, T.R., et al., "Closed-wound drainage systems: the Solcotrans Plus versus the Stryker-CBC ConstaVAC", Orthopaedic Review, 20(6):536-542 (Jun. 1991).
Woodley, D.T., et al., "A double-blind comparison of adhesive bandages with the use of uniform suction blister wounds", Arch. Dermatol., 128(10):1354, 1357 (Oct. 1992).
Zelko, J.R., et al., "Primary closure of the contaminated wound; closed suction wound catheter", Am. J. Surgery, 142:704-706, (Dec. 1981).
Bagautdinov, N.A., "Alternative method of external vacuum aspiration in the treatment of purulent soft tissue disease," Curr. Problems Contemporary Clin. Surg.: Interscholastic Collection, pp. 94-96, (6 sheets of English translation and certification dated May 30, 2008; four sheets of English translation, 6 sheets in Russian, and certification dated May 9, 2008; 1 sheet of English translation of alleged library index card, 1 sheet in Russian, and certification dated May, 7, 2008); I.N. Ulianov Chuvash State University, Cheboksary, (1986).
Zivadinovic, G., et al., "Vacuum therapy in the treatment of peripheral blood vessels," Conference Papers of the 5th Timok Medical Days, Majdanpek, No. 3-4, pp. 161-164, (5 sheets English translation; 5 sheets in Serbian, certification dated May 9, 2008) (1986).
Johnson, F.E., "An improved technique for skin graft placement using a suction drain", Surg. Gynecol. Obstet., 159 (6):584-585 (Dec. 1984).
Safronov, A.A., Dissertation Abstract, "Vacuum therapy of trophic ulcers of the lower leg with simultaneous autoplasty of the skin," (Central Scientific Research Institute of Traumotology and Orthopedics, Moscow, U.S.S.R.) (23 sheets English translation; 23 sheets in Russian; certification dated May 8, 2008; alleged index card(English translation; 1 sheet Russian; certification dated May 14, 2008), (1967).
Tribble, D.E., "An improved sump drain-irrigation device of simple construction," Arch. Surg., 105:511-513, (Sep. 1972).
Tennant, C.E., "The use of hyperemia in the postoperative treatment of lesions of the extremities and thorax," Jour. A.M.A., 64(19):1548-1549, (May 8, 1915).
Orgill, D.P., et al., "Microdeformational wound therapy—a new era in wound healing," Business Briefing: Global Surgery—Future Directions, pp. 22, 24-25 (2005).

(56) References Cited

OTHER PUBLICATIONS

"V.A.C.® Therapy Clinical Guidelines: A reference source for clinicians," KCI, The Clinical Advantage® (Jul. 2007).
Westaby, S., et al., "A wound irrigation device," Lancet, pp. 503-504, (Sep. 2, 1978).
Conquest, A.M., et al., "Hemodynamic effects of the vacuum-assisted closure device on open mediastinal wounds,"J. Surg. Res., 115(2):209-13 (Dec. 2003).
Copson, D., "Topical negative pressure and necrotising fasciitis", Nurs. Stand., 18(6):71-2, 74, 76, 78, 80 (Oct. 22, 2003).
Demaria, R.G., et al., "Topical negative pressure therapy. A very useful new method to treat severe infected vascular approaches in the groin,"J. Cardiovascular Surg., 44(6):757-61 (Dec. 2003).
De Vooght, A., et al., "Vacuum-assisted closure for abdominal wound dehiscence with prosthesis exposure in hernia surgery,"Plast. Recont. Surg., 112(4):1186-9 (Sep. 15, 2003).
Duxbury, M.S., et al., "Use of a vacuum assisted closure device in pilonidal disease,"J. Wound Care, 12(9):355 (Oct. 2003).
Eldad, A., et al., "Vacuum—A novel method for treating chronic wounds", Harefuah, (English abstract on last 2 pp. and 1 sheet printout from PubMed); 142(12):834-6, 878, 877 (Dec. 2003).
Evans, D., et al., "Topical negative pressure for treating chronic wounds", Cochrane Database Syst. Rev., vol. (3), accession No. 00075320-100000000-01309 (2005).
Fuchs, U., et al., "Clinical outcome of patients with deep sternal wound infection managed by vacuum-assisted closure compared to conventional therapy with open packaging: a retrospective analysis", Ann. Thorac. Surg., 79:526-31 (2005).
Gustafsson, R.I., et al., "Deep sternal wound infection: a sternal-sparing technique with vacuum-assisted closure therapy"Ann. Thorac. Surg., 76(6):2048-53 (Dec. 2003).
Herscovici Jr., D., et al., "Vacuum-assisted wound closure (VAC therapy) for the management of patients with highenergy soft tissue injuries", J. Orthop. Trauma, 17(10):683-8 (Nov.-Dec. 2003).
Huang, J., et al., "Treatment of open fracture by vacuum sealing technique and internal fixation", Zhongguo Xiu Fu Chong Jian Wai Ke Za Zhi, (English abstract on first page and 2 sheets printout from PubMed); 17(6):456-8 (Nov. 2003).
Jones, E.G., et al., "Management of an ileostomy and mucous fistula located in a dehisced wound in a patient with morbid obesity", J. Wound Ostomy Continence Nurs., 30(6):351-356 (Nov. 2003).
Langley-Hawthorne, C., "Economics of negative pressure wound therapy", Ostomy Wound Manage., 50(4A suppl):35, 36, C3 (Apr. 2004).
Neubauer, G., et al., "The cost-effectiveness of topical negative pressure versus other wound-healing therapies", J. Wound Care, 12(10):392-3 (Nov. 2003).
Orgill, D.P., et al., "Functional reconstruction following electrical injury", Ann. N.Y. Acad. Sci., 888:96-104 (Oct. 30, 1999).
Salameh, J.R., et al., "Laparoscopic harvest of omental flaps for reconstruction of complex mediastinal wounds", JSLS, 7(4):317-22 (Oct.-Dec. 2003).
Shoufani, A., et al., "Vacuum assisted closure—a new method for wound control and treatment", Harefuah, (English abstract on last page; 1 sheet printout from PubMed); 142(12):837-40, 877 (Dec. 2003).
Shvartsman, H.S., et al., "Use of vacuum-assisted closure device in the treatment of recurrent Paget's disease of the vulva", Obstet. Gynecol., Supplement, 102(5, part 2):1163-6 (Nov. 2003).
Sibbald, R.G., et al., "A consensus report on the use of vacuum-assisted closure in chronic, difficult-to-heal wounds", Ostomy Wound Manage., 49(11):52-66 (Nov. 2003).
Wagner, S., et al., "Comparison of inflammatory and systemic sources of growth factors in acute and chronic human wounds", Wound Rep. Reg., 11:253-260 (Jul.-Aug. 2003).
Wild, T., "Consensus of the German and Austrian Societies for wound healing and wound management on vacuum closure and the VAC treatment unit", MMW Fortschr. Med., (English abstract on p. 100; 1 sheet printout from PubMed); 145 Suppl. 3:97-101 (Oct. 9, 2003).

Chen, S.Z., et al., "Effect of vacuum-assisted closure on the expression of proto-oncogenes and its significance during wound healing", Zhonghua Zheng Xing Wai Ke Za Zhi, (English abstract on first page, 2 sheets printout from PubMed); 21:197-200 (May 2005).
Immer, F.F., et al., "Deep sternal wound infection after cardiac surgery: modality of treatment and outcome", Ann. Thorac. Surg., 80(3):957-61 (Sep. 2005; available online Aug. 23, 2005).
Saltzman, C.L., "Salvage of diffuse ankle osteomyelitis by single-stage resection and circumferential frame compression arthrodesis", Iowa Orthop. J., 25:47-52 (2005).
Bogart, L., "A summary of posters presented at the symposium on Advanced Wound Care: 2003 and 2004", Ostomy Wound Manage., 51(4):88-91 (Apr. 2005).
Chen, S.Z., et al., "Effects of vacuum-assisted closure on wound microcirculation: an experimental study", Asian J. Surg., 28(3):211-7 (Jul. 2005).
Paul, J.C., "Vacuum assisted closure therapy: A must in plastic surgery", Plastic Surg. Nurs., 25(2):61-5 (Apr.-Jun. 2005).
Winter, D., "Perspectives on vacuum-assisted closure therapy in pilonidal sinus surgery", Dis. Colon Rectum, 48 (9):1829-30, (Sep. 2005).
Arca, M.J., et al., "Use of vacuum-assisted closure system in the management of complex wounds in the neonate", Pediatr. Surg. Int., 21(7):532-5, 8 sheets, (published online Jun. 17, 2005).
Adamkova, M., et al., "First experience with the use of vacuum assisted closure in the treatment of skin defects at the burn center", Acta. Chir. Plast., 47(1):24-7 (2005).
Venturi, M.L., et al., "Mechanisms and clinical applications of the vacuum-assisted closure (VAC) device: a review", Am. J. Clin. Dermatol., 6(3):185-94 (2005).
Noel, B., "Management of venous leg ulcers", Rev. Med. Suisse, (English abstract on first page, 1 sheet printout from PubMed); 1(16):1062-6, 1068 (Apr. 20, 2005).
Riccio, M., et al. "Delayed microsurgical reconstruction of the extremities for complex soft-tissue injuries", Microsurgery, 25:272-83 (2005).
Sjogren, J., et al., "Clinical outcome after poststernotomy mediastinitis: vacuum-assisted closure versus conventional treatment", Ann. Thorac. Surg., 79(6):2049-55 (Jun. 2005).
Dainty, L.A., et al., "Novel techniques to improve split-thickness skin graft viability during vulvo-vaginal reconstruction", Gynecol. Oncol., 97(3):949-52 (Jun. 2005).
Clubley, L., et al., "Using negative pressure therapy for healing of a sternal wound", Nurs. Times. 101(16):44-6 (Apr. 19, 2005).
Caniano, D.A., et al., "Wound management with vacuum-assisted closure: experience in 51 pediatric patients", J. Pediatr. Surg., 40(1):128-32 (Jan. 2005).
Steenvoorde, P., et al., "Deep infection after ilioinguinal node dissection: vacuum-assisted closure therapy?"Low. Extrem. Wounds, 3(4):223-226 (Dec. 2004).
Ryan, T.J., "Evans (1966) exchange and the skin in the light of vacuum-assisted closure, yoga, and maggots", Low. Extrem. Wounds, 3(3):121-2 (Sep. 2004).
Armstrong, D.G., et al., "Decreasing foot pressures while implementing topical negative pressure (vacuum-assisted closure) therapy", Low. Extrem. Wounds, 3(1):12-15 (Mar. 2004).
Wackenfors, A., et al., "Blood flow responses in the peristemal thoracic wall during vacuum-assisted closure therapy", Ann. Thorac. Surg., 79(5):1724-31 (May 2005).
Whelan, C., et al., "Mechanics of wound healing and importance of vacuum-assisted closure® in urology", J. Urol., 173:1463-70 (May 2005).
O'Connor, J., et al., "Vacuum-assisted closure for the treatment of complex chest wounds", Ann. Thorac. Surg., 79 (4):1196-200 (Apr. 2005).
Nugent, N., et al., "Vacuum-assisted closure—management option for the burns patients with exposed bone", Burns, 31(3):390-393 (May 2005) (Epub Jan. 22, 2005).
Lambert, K.V., et al., "Vacuum assisted closure: a review of development and current applications", Eur. J. Vasc. Endovasc. Surg., 29(3):219-226 (Mar. 2005).

(56) References Cited

OTHER PUBLICATIONS

Smith, N., "The benefits of VAC Therapy in the management of pressure ulcers", Br. J. Nurs., 13(22):1359-60, 1362, 1364-65 (Dec. 9, 2004-Jan. 12, 2005).
White, R.A., et al., "Vacuum-assisted closure complicated by erosion and hemorrhage of the anterior tibial artery", J. Orthop. Trauma, 19(1):56-59 (Jan. 2005).
De Geus, H.R.H., et al., "Vacuum-assisted closure in the treatment of large skin defects due to necrotizing fasciitis", Intensive Care Med., 31(4): 601 (1 page) (Apr. 2005) (Epub Jan. 22, 2005).
Samson, D., et al., "Wound-healing technologies: low level laser and vacuum-assisted closure", Evid. Rep. Technol. Assess. (Summ.),(111):1-6, (Dec. 2004).
Gibson, K., "Vacuum-assisted closure", Am. J. Nurs., 104(12): 16 (1 page) (Dec. 2004).
Bagautdinov, N.A., "Variant of external vacuum aspiration in the treatment of purulent diseases of soft tissues," Current Problems in Modern Clinical Surgery, Interdepartmental Collection, Cheboksary, (4 pages of English translation, 6 sheets in Russian, certification dated May 22, 2008, English translation of index card, 1 sheet Russian, certification dated May 7, 2008) (1986).
Chardak, W.M., et al., "Experimental studies on synthetic substitutes for skin and their use in the treatment of burns," Ann. Surg., 155(1):127-139, (Jan. 1962).
Fujimori, R., et al., "Sponge fixation method for treatment of early scars," Plast. & Reconst. Surg., 42(4):322-326, (Oct. 1968).
Kirk-Othmer, Encyclopedia of Chemical Technology, 2nd completely revised edition, vol. 14, pp. 227, John Wiley & Sons, Inc., (1967).
Meyer, W., et al., excerpts from "Bier's Hyperemic Treatment", W.B. Saunders and Co., (48 sheets) (1908).
Zivadinovic, G., et al., "Vacuum therapy in the treatment of peripheral blood vessels," Timok Medical Journal, Abstract book of the 5th Timok Medical Days, Majdanpek, 6 sheets of English translation, (1986).
Safronov, A.A., "Vacuum therapy for trophic ulcers of the tibia with concurrent skin autoplasty," Dissertation abstract, additional abstract, Moscow, 20 sheets of English translation, (1967).
Safronov, A.A., Abstract of Invention No. 240188, "Device for wound or ulcer treatment," (2 sheets English translation and 2 sheets in Russian) (1969).
3M™ Inzisionsfolien—Produktubersicht, by 3M Medica, 6 annotated sheets.
Application for rationalization proposal, proposal entitled "Variant for vacuum treatment of purulent wounds," (4 sheets in English, 4 sheets in Russian, certificate of translation dated May 8, 2009), proposal allegedly executed Dec. 25, 1985 (Bagautdinov III).
Buschbaum, H.J., ed., et al., Strategies in Gynecologic Surgery, pp. 203, Springer-Verlag, NY, (1986).
Flynn, J-B. McC., et al., Technological Foundations in Nursing, pp. 506-507, Appleton & Lange, Norwalk, CT, (1990).
GOMCO Mobile constant and intermittent model 6030 & 6031, Operation, Maintenance and Service Manual, with annotations, 21 sheets, (Jan. 1987).
Kahlson, G., et al., "Wound healing as dependent on rate of histamine formation," The Lancet, pp. 230-234, (Jul. 30, 1960).
Karev, I.D., et al., "Foam drainage system for treating purulent wounds," pp. 87-88, (2 sheets English translation, 2 sheets Russian and certifcation of translation dated Apr. 6, 2009) (allegedly dated 1986).
Kozier, B., et al., Techniques in Clinical Nursing, 3d ed., pp. 559-560, pp. 603-605, Addison-Wesley Publishing Company, Inc., Health Sciences, Redwood City, CA, (1989).
McLean, W. C., "The role of closed wound negative pressure suction in radial surgical procedures of the head and neck," The Laryngoscope, 74(1)70-94, (Jan. 1964).
Norton, B.A., et al., Skills for Professional Nursing Practice: communication, physical appraisal, and clinical techniques, pp. 298-302, pp. 328-329, Appleton-Century-Crofts, Norwalk, CT (1986).

Bagautdinov, N.A., Report on Practical Application entitled "Variant of vacuum treatment of purulent wounds," Kazan Municipal Hospital No. 8, (1 sheet in English, 1 sheet in Russian and certificate of translation dated May 8, 2009), (allegedly dated Dec. 24, 1985). (Practical Report I).
Kuznetsov, V.A. et al., Report on Practical Application entitled "Method of vacuum-sorption treatment of purulent wounds," Kazan Municipal Hospital No. 8, (1 sheet in English, 1 sheet in Russian and certificate of translation dated Apr. 28, 2009) (allegedly dated May 19, 1986). (Practical Report II).
Bagautdinov, N.A., Report on Practical Application entitled "Method of vacuum treatment of open purulent wounds," Medical-Sanitary Ward of the Arzamas Instrument Plant, (1 sheet in English, 1 sheet in Russian and certificate of translation dated Apr. 27, 2009) (allegedly dated 1986).(Practical Report III).
Roth, B., et al., "Ubersichtsarbeit: Indication for suction-rinse drainage and hygienic certainty in drainages," GMS Krankenhaushyg. Interdiszip, 1(1):Doc27 (7 sheets in German with English abstract on first sheet) (2006).
Schneider, F.R., Handbook for the Orthopaedic Assistant, 2nd ed., pp. 185, The C.V. Mosby Company, St. Louis, (1976).
Thomas, S., Wound Management and Dressings, Chapter 4: Semipermeable film dressings (continued onto pp. 26-34), Chapter 5: Foam dressings (continued onto pp. 36-42), and pp. 166, The Pharmaceutical Press, London, (1990).
Witkowski, J.A., et al., "Synthetic dressings: wound healing in the 80's," (5 sheets), Hospital Therapy, (Nov. 1986).
Excerpts from Bier's Hyperemic Treatment, pp. 17-25, 44-46, 90-96, 167-170, 210-211 (1909).
Polly Jr., D.W., et al., "Advanced medical care for soldiers injured in Iraq and Afghanistan", Minn. Med., 87(11):42-4 (Nov. 2004).
Stone, P.A., et al., "Vacuum-assisted fascial closure for patients with abdominal trauma", J. Trauma, 57:1082-6 (Nov. 2004).
Connolly, T.P., "Necrotizing surgical site infection after tension-free vaginal tape", Obstet. Gynecol., 104(6):1275-6 (4 pages) (Dec. 2004).
Wackenfors, A., et al., "Effects of vacuum-assisted closure therapy on inguinal wound edge microvascular blood flow", Wound Rep. Regen., 12(6):600-6 (Nov.-Dec. 2004).
Schaffzin, D.M., et al., "Vacuum-assisted closure of complex perineal wounds", Dis. Colon Rectum, 47:1745-8 (Oct. 2004) (Published online Aug. 24, 2004).
Yousaf, M., et al., "Use of vacuum-assisted closure for healing of a persistent perineal sinus following panproctocolectomy: report of a case", Dis. Colon Rectum, 47(8):1403-8 (Aug. 2004) (Published online Aug. 12, 2004).
Fox, A., et al., "An unusual complication of vacuum assisted closure in the treatment of a pressure ulcer", J. Wound Care, 13(8):344-5 (Sep. 2004).
Saxena, V., et al., "Vacuum-assisted closure: microdeformations of wounds and cell proliferation", Plast. Reconstruct. Surg., 114(5):1086-96 (Oct. 2004).
Scholl, L., et al., "Sternal osteomyelitis: use of vacuum-assisted closure device as an adjunct to definitive closure with sternectomy and muscle flap reconstruction", J. Card. Surg., 19(5):453-61 (Sep.-Oct. 2004).
Ohye, R.G., et al. "Primary closure for postoperative mediastinitis in children", J. Thorac. Cardiovasc. Surg., 128.(3):480-6 (Sep. 2004).
Tang, S.Y., et al., "Influence of vacuum-assisted closure technique on expression of Bcl-2 and NGF/NGFmRNA during wound healing", Zhonghua Zheng Xing Wai Ke Za Zhi, (English abstract on first page 1 sheet printout from PubMed); 20(2):139-42 (Mar. 2004).
Armstrong, D.G., et al., "Guidelines regarding negative wound therapy (NPWT) in the diabetic foot", Ostomy Wound Manage., 50(4B Suppl.):3S-27S (Apr. 2004).
Shilt, J.S., et al., "Role of vacuum-assisted closure in the treatment of pediatric lawnmower injuries", J. Pediatr. Orthop., 24(5):482-7 (Sep.-Oct. 2004).
Antony, S., et al., "A retrospective study: clinical experience using vacuum-assisted closure in the treatment of wounds", J. Natl. Med. Assoc., 96(8):1073-7 (Aug. 2004).

(56) References Cited

OTHER PUBLICATIONS

Steenvoorde, P., et al., "Vacuum-assisted closure therapy and oral anticoagulation therapy", Plast. Reconstruct. Surg., 113(7):2220-1 (Jun. 2004).
Oczenski, W., et al., "Vacuum-assisted closure for the treatment of cervical and mediastinal necrotizing fasciitis", J. Cardiothorac. Vasc. Anesth., 18(3):336-8 (Jun. 2004).
Carson, S.N., et al., "Vacuum-assisted closure used for healing chronic wounds and skin grafts in the lower extremities", Ostomy Wound Manage., 50(3):52-8 (9 sheets) (Mar. 2004).
Marathe, U.S., et al., "Use of the vacuum-assisted closure device in enhancing closure of a massive skull defect", Laryngoscope, 114(6):961-4 (8 sheets) (Jun. 2004).
Schintler, M.V., et al., "The impact of the VAC-treatment for locally advanced malignancy of the scalp", Zentralbl. Chir., (English abstract on first page, 1 sheet printout from PubMed); 129 Suppl: 1:S141-S146 (May 2004).
Querings, K., et al., "Revitalization of a gluteal abscesses with V.A.C. therapy (vacuum assisted closure)", Zentralbl. Chir., (English abstract on first page 1 sheet printout from PubMed); 129 Suppl 1:S138-S140 (May 2004).
Kall, S., et al., "Influence of foam- and tubing material of the vacuum assisted closure device (V.A.C.) on the concentration of transforming growth factor beta 1 in wound fluid", Zentralbl. Chir., (English abstract on first page, 2 sheets printout from PubMed); 129 Suppl 1: S113-S115 (May 2004).
Mang, R., et al., "Vacuum therapy in a pre- and postsurgical ulcera crurum", Zentralbl. Chir., (English abstract on first page, 1 sheet printout from PubMed); 129 Suppl 1:S101-S103 (May 2004).
Steiert, A.E., et al., "The V.A.C. system (vacuum assisted closure) as bridging between primary osteosynthesis in conjunction with functional reconstructed of soft tissue—open fractures type 2 and type 3", Zentralbl. Chir., (English abstract on first page, 2 sheets printout from PubMed); 129 Suppl 1:S98-100 (May 2004).
Karl, T., et al., "Indications and results of V.A.C. therapy treatments in vascular surgery—state of the art in the treatment of chronic wounds", Zentralbl. Chir., (English abstract on first page, 1 sheet printout from PubMed); 129 Suppl 1:S74-S79 (May 2004).
Ferbert, T., et al., "Treatment of soft tissue defects on hang and forearm with vacuum assisted closure", Zentralbl. Chir., (English abstract on first page, 1 sheet printout from PubMed); 129 Suppl 1:S57-S58 (May 2004).
Halama, D., et al., "Intraoral application of vacuum-assisted closure in the treatment of an extended mandibular keratocyst", Zentralbl. Chir., (English abstract on first page, 1 sheet printout from PubMed); 129 Suppl 1:S53-S56 (May 2004).
Fleck, T., et al., "Early treatment of sternal wound infections with vacuum assisted closure therapy reduces involvement of the mediastinum and further diminishes the need of plastic reconstructive surgery", Zentralbl. Chir., (1 sheet printout from PubMed); 129 Suppl 1:S35-S37 (May 2004).
Kutschka, I., et al., "Vacuum assisted closure therapy improves early postoperative lung function in patients with large sternal wounds", Zentralbl. Chir., (English abstract on first page, 1 sheet printout from PubMed); 129 Suppl 1: S33-S34 (May 2004).
Labler, L., et al., "New application of V.A.C. (vacuum assisted closure) in the abdominal cavity in case of open abdomen therapy", Zentralbl. Chir., (English abstract on first page, 2 sheets printout from PubMed); 129 Suppl 1:S14-S19 (May 2004).
Wild, T., et al., "Consensus of the German and Austrian Societies for Wound Healing and Wound Management on vacuum closure and the V.A.C. treatment unit", Zentralbl. Chir., (English abstract on first page, 2 sheet printout from PubMed and 1 sheet of erratum); 129 Suppl 1:S7-S11 (May 2004).
Weed, T., et al., "Qunatifying bacterial bioburden during negative pressure wound therapy. Does the wound VAC enhance bacterial clearance?"Ann. Plast. Surg., 52(3):276-80 (Mar. 2004).
Mustoe, T., "Understanding chronic wounds: a unifying hypothesis on their pathogenesis and implications for therapy", Am. J. Surg., 187(5A):65S-70S (May 2004).

Tzeng, Y.J., et al., "Using vacuum-assisted closure (VAC) in wound management", Hu Li Za Zhi, (english abstract on last page, 1 sheet printout from PubMed); 51(2):79-83 (Apr. 2004).
Quah, H.M., et al., "Vacuum-assisted closure in the management of the open abdomen: a report of a case and initial experiences", J. Tissue Viability, 14(2):59-62 (Apr. 2004).
Emohare, O., et al., "Vacuum-assisted closure use in calciphylaxis", J. Burn Care Rehabil., 25(2):161-4 (Mar.-Apr. 2004).
Wackenfors, A., et al., "The effect of vacuum-assisted closure therapy on the pig femoral artery vasomotor responses", Wound Repair Regen., 12(2):244-51 (Mar.-Apr. 2004).
Sjogren, J., et al., "Vacuum-assisted closure therapy in mediastinitis after heart transplantation", J. Heart Lung Transplant., 23(4):506-7 (Apr. 2004).
Miller, Q., et al., "Effect of subatmospheric pressure on the acute healing wound", Cuff. Surg., 61(2):205-8 (Mar.-Apr. 2004).
Penn, E., et al., "Management of a dehisced abdominal wound with VAC therapy", Br. J. Nurs., 13(4):194, 196, 198-201 (Feb. 26-Mar. 10, 2004).
Moues, C.M., et al., "Bacterial load in relation to vacuum-assisted closure wound therapy: a prospective randomized trial", Wound Repair Regen., 12(1):11-7 (Jan.-Feb. 2004).
Schimp, V.L., et al., "Vacuum-assisted closure in the treatment of gynecologic oncology wound failures", Gynecol. Oncol., 92(2):586-91 (Feb. 2004).
Aru, G.M., et al., "Limitations on the role of vacuum-assisted closure in cardiac surgery", J. Thorac. Cardiovasc. Surg., 127(2):604-5 (Feb. 2004).
Bihariesingh, V.J., et al., "Plastic solutions for orthopaedic problems", Arch. Orthop. Trauma. Surg., 124(2):73-6 (Mar. 2004) (Epub Jan. 17, 2004).
Kaplan, M., "Managing the open abdomen", Ostomy Wound Manage., 50(1A suppl):C2, 1-8, and 1 sheet of quiz (Jan. 2004).
Colwell, A.S., et al., "Management of early groin vascular bypass graft infections with sartorius and rectus femoris flaps", Ann. Plast. Surg., 52(1):49-53 (Jan. 2004).
Evidence Report/Technology Assessment, No. 111, "Wound healing technologies: low-level laser and vacuum-assisted closure", prepared for Agency for Healthcare Research and Quality by the Blue Cross and Blue Shield Association Technology Evaluation Center Evidence-based Practice Center, under Contract No. 290-02-0026, AHRQ Publications Clearinghouse, Available Dec. 2004.
Wolvos, T., "Wound instillation—the next step in negative pressure wound therapy. Lessons learned from initial experiences", Ostomy Wound Manage., 50(11):56-58, 60-66 (Nov. 2004).
Bluman, E.M., et al., "Subatmospheric pressure-induced compartment syndrome of the entire upper extremity. A case report", J. Bone Joint Surg. (Am.), 86-A(9):2041-4 (Sep. 2004).
Kamolz, L.P., et al., "Use of subatmospheric pressure therapy to prevent burn wound progression in human: first experiences", Burns, 30(3):253-8 (May 2004) (Available online Mar. 16, 2004).
Jones, S.M., et al., "Advances in wound healing: topical negative pressure therapy", Postgrad. Med. J., 81 (956):353-7 (Jun. 2005).
Thomas, S., "Pain and wound management," Community Outlook, pp. 11-13, 15 and one extra sheet, (Jul. 1989).
Livshits, V.S., "Polymer dressings for wounds and burns (review)," All-Union Scientific-Research Institute for Medical Polymers, Moscow, pp. 515-522, (allegedly published in Pharmaceutical Chemical Journal, 22(7):790-798, translated from Russian (allegedly dated Jul. 1988)), Plenum Publishing Corp., (1989).
Calne, S., ed., Position Document: Pain at wound dressings changes, pp. 1-17 and 3 additional sheets, supported by Molnlycke Health Care, (allegedly dated 2002).
Skover, G., et al., "45: New Technologies: An Overview," Chronic Wound Care, pp. 425-430 (allegedly dated 1990).
2 sheets of documents, the citation is alleged to be: David JA, Wound Management: A Comprehensive Guide to Dressing and Healing, pp. 51-51 (allegedly dated 1986).
Thomas, S., "Selecting dresssings," Community Outlook, vol. 6, 4 sheets, (Jun. 1991).
1 sheet document, the citation is alleged to be: David J., Extract from Practical Nursing Handbook: Wound Management a Comprehensive Guide to Dressing and Healing, pp. 166-167, (allegedly dated 1986).

(56) References Cited

OTHER PUBLICATIONS

Johnson, F.E., "An improved technique for skin graft placement using a suction drain", Surg. Gynecol. Obstet., 159 (6):585-586 (Exhibit D-132) (Dec. 1984).

Svedman, P., "A dressing allowing continuous treatment of a biosurface,"IRCS Medical Science: Biomedical Technology; Clinical Medicine; Surgery and Transplantation, 7:221 (1979), with annotations.

Viljanto, J., "A new method for treatment of open wounds", Ann. Chir. Gynaecol. Fenn., (English abstract on first page and 1 sheet printout from PubMed); 60:94-100 (1972).

Yusupov, Y.N., et al., "Active drainage of wounds", Vestn. Khir. Im. I.I. Grek., (with English abstract on last page, 5 sheets of English translation, 3 pp. of English translation by BlueSky publishing and 1 sheet printout from PubMed); 138(4):42-46 (Apr. 1987).

Avery, C., et al., "Negative pressure wound dressing of the radial forearm donor site", International Journal of Oral Macillofacial Surgery, 2000; 29, pp. 198-200.

Armstrong, David G., et al., "Outcomes of Subatmospheric Pressure Dressing Therapy on Wounds of the Diabetic Foot", Ostomy/Wound Management 2002; 48(4): 64-68.

Brown, Karen M., et al., "Vacuum-Assisted Closure in the Treatment of a 9-Year-Old Child with Severe and Multiple Dog Bite Injuries of the Thorax", Society of Thoracic Surgeons, 2001; 72:1409-1410.

Catarino, Pedro A., et al., "High-Pressure Suction Drainage via a Polyurethane Foam in the Management of Poststernotomy Mediastinitis", Ann Thorac Surg 2000; 70:1891-5.

Mendez-Eastman, Susan, RN, CPSN, CWCN, Clinical Management Extra, Guidelines for Using Negative Pressure Wound Therapy, Advances in Skin & Wound Care, Nov./Dec. 2001, vol. 14, No. 6, p. 314-323.

Cooper, Susan Mary, "Topical negative pressure in the treatment of pressure ulcers", Letters posted in the Journal of the American Acad of Dermatology, August, Part 1, 1999, p. 280.

Davydov, I.A., et al., "Concept of clinico-biological control of the wound", Vestnik khirurgii imeni I.I. Grekova, v. 146, issue 2, 1991, 132-6 (with English translation).

de la Torre, Jorge I., MD, et al., "Healing a Wound with an Exposed Herrington Road: A Case Study", Ostomy Wound Management, pp. 18-19, May 2002, vol. 48, Issue 5.

de Lange, M.Y., et al., "Vacuum-assisted closure: indications and clinical experience", Eur J Plast Surg (2000) 23:178-182.

Deva, Anand, K., et al., "Topical negative pressure in wound management", MJA, Vo. 173, pp. 128-131, Aug. 7, 2000.

Elwood, Eric T., et al., "Negative-Pressure Dressings in the Treatment of Hidradenitis Suppurativa", Ann Plast Surgery Jan. 2001; 46:49-51.

Evans, D. and Land, L., "Topical negative pressure for treating chronic wounds: a systematic review", British Journal of Plastic Surgery (2001), 54, 238-242.

Fabian, Thaddeus S., MD, "The Evaluation of Subatmospheric Pressure and Hyperbaric Oxygen in Ischemic Full-Thickness Wound Healing", The American Surgeon, Dec. 2000, vol. 66, 1136-1143.

Fenn, C.H. and Butler, P.E.M., "Abdominoplasty wound-healing complications: assisted closure using foam suction dressing", British Journal of Plastic Surgery (2001), 54, 348-351.

Giovannini, Uberto M., MD, "Negative Pressure for the Management of an Exposed Vascular Dacron Polyester Patch", Annals of Plastic Surgery, 47(5): 577-578, 2001.

Gustafsson, Ronny, MD, "Vacuum-assisted closure therapy guided by C-reactive protein level in patients with deep sternal wound infection", The Journal of Thoracic and Cardiovascular Surgery, vol. 123, No. 5, pp. 895-900, May 2002.

Gwan-Nulla, Daniel N., MD and Casal, Rolando S., MD, "Toxic Shock Syndrome Associated with the Use of the Vacuum-Assisted Closure Device", Ann Plastic Surgery 2001;47:552-554.

Hersh, Robert E., MD, et al., "The Vacuum-Assisted Closure Device as a Bridge to Sternal Wound Closure", Ann Plast Surg. 2001; 46: 250-254.

Heugel, Judson R., et al., "Treatment of the Exposed Achilles Tendon Using Negative Pressure Wound Therapy: A Case Report", Journal of Burn Care and Rehabilitation, May/Jun. 2002, vol. 23, No. 3, pp. 167-171.

Joseph, Emmanuella, MD, et al., "A Prospective Randomized Trial of Vacuum-Assisted Closure Versus Standard Therapy of Chronic Nonhealing Wounds", Wounds 2000: 12(3): 60-67.

Josty, I.C., et al., "Vacuum-assisted closure: an alternative strategy in the management of degloving injuries of the foot", British Journal of Plastic Surgery (2001), 54, pp. 363-365.

Kostiuchenok, B.M., et al., "Vacuum Treatment in the Surgical Management of Suppurative Wounds", Izdatelstvo Meditsina, St. Petersburg, Sep. 1986; 137(9): 18-21 (with English Translation).

Stone, P., et al., "Bolster versus negative pressure wound therapy for securing split-thickness skin grafts in trauma patients", Wounds, 16(7):219-23 (5 sheets) (2004) (Posted Aug. 4, 2004).

Wolvos, T., "Wound instillation with negative pressure wound therapy", Ostomy Wound Manage., 51(2A suppl):21S-26S (Feb. 2005).

Jeter, K., "Closed suction wound drainage system", JWOCN, 31(2):51 (1 sheet) (Mar.-Apr. 2004).

Agarwal, J.P., et al., "Vacuum-assisted closure for sternal wounds: a first-line therapeutic management approach", Plast. Reconstr. Surg., 116(4)1035-1040 (Sep. 15, 2005).

Sjogren, J., et al., "The impact of vacuum-assisted closure on long-term survival after post-sternotomy mediastinitis", Ann. Thorac. Surg., 80(4):1270-5, (Oct. 2005).

Mendez-Eastman, S., "New advances in wound therapy", printout from Wounds1.com; 7 sheets (Apr. 15, 2005).

"Promoting wound healing", Nurses-Digest, 2(3), 6 sheets, Mar. 2005.

Roylance, L., "Nancy Sujeta, Amanda Clark,"DOME, vol. 55, Mar. 2004, 2 sheets of website printout www.hopkinsmedicine.org/dome/0405/feature4.cfm.

Agarwal, J.P., et al., "Vacuum assisted closure™ for sternal wounds: a first line therapeutic management", ASPS, Plastic Surgery 2004, Philadelphia, PA, abstract (2 sheets) (Wednesday Oct. 13, 2004).

Gomoll, A.H., et al., "Incisional vacuum-assisted closure therapy", J. Orthop. Trauma, 20(10):705-709, (Nov.-Dec. 2006).

Leininger, B.E., et al., "Experience with wound VAC and delayed primary closure of contaminated soft tissue injuries in Iraq", J. Trauma, 61(5):1207-1211 (Nov. 2006).

Gupta, S., ed., "Differentiating negative pressure wound therapy devices: an illustrative case series", Wounds, 19(1 suppl):1-9, (Jan. 2007).

Korasiewicz, L.M., "Abdominal Wound With a Fistula and Large Amount of Drainage Status After Incarcerated Hernia Repair", Journal of Wound, Ostomy & Continence Nursing. 31(3):150-153, (May-Jun. 2004).

Guntinas-Lichius, O., et al., "The role of growth factors for disease and therapy in diseases of the head and neck", DNA and Cell Biol., 22(9):593-606, (Sep. 2003).

Goldman, R., "Growth factors and chronic wound healing: past, present, and future", Adv. Skin Wound Care, 17 (1):24-35, (Jan.-Feb. 2004).

Malli, S., "Keep a close eye on vacuum-assisted wound closure", Nursing, 35(7):25 (Jul. 2005).

Lynch, J.B., et al., "Vacuum-assisted closure therapy: a new treatment option for recurrent pilonidal sinus disease. Report of three cases", Dis. Colon Rectum, 47(6):929-32 (Jun. 2004) (Published online May 4, 2004).

MX: Business Strategies for Medical Technology Executives, (Mar./Apr. 2005).

Niezgoda, J.A., "Incorporating negative pressure therapy into the management strategy for pressure ulcers", Ostomy Wound Manage., 50(11A suppl.):5S-8S, (Nov. 2004).

Banwell, P.E., "Topical negative pressure therapy: advances in burn wound management", Ostomy Wound Manage., 50(11A suppl.):9S-14S, (Nov. 2004).

Kaplan, M., "Negative pressure wound therapy in the management of abdominal compartment syndrome", Ostomy Wound Manage., 50(11A suppl):20S-25S, (Nov. 2004).

(56) References Cited

OTHER PUBLICATIONS

Gupta, S., et al., "The perioperative use of negative pressure wound therapy in skin grafting", Ostomy Wound Manage., 50(11A suppl.):26S-28S, (Nov. 2004).
Schoemann, M.B., et al., "Treating surgical wound dehiscence with negative pressure dressings", Ostomy Wound Manage., 51(2A suppl.):15S-20S, (Feb. 2005).
Bookout, K., et al., "Case studies of an infant, a toddler, and an adolescent treated with a negative rpessure wound treatment system", J. Wound OstomyContinence Nurs., 31(4):184-192, (8 pp.) (Jul./Aug. 2004).
Borkowski, S., "G tube care: managing hypergranulation tissue", Nursing, 35(8):24 (Aug. 2005).
Machen, M. S., "Management of traumatic war wounds using vacuum-assisted closure dressings in an austere environment," Army Medical Department J., pp. 17-23, (Jan.-Mar. 2007).
Peck, M.A., et al., "The complete management of extremity vascular injury in a local population: a wartime report from the 332nd Expeditionary Medical Group/Air Force Theater Hospital, Balad Air Base, Iraq," J. Vasc. Surg., pp. 1-9, (2007), (Presented at the Plenary Session of the Eastern Vascular Society's Twentieth Annual Meeting, Washington D. C., Sep. 30, 2006).
Giovannini, U.M., et al., "Topical negative therapy and vacuum assisted closure. New strategies and devices in surgical reconstruction", Minerva Chir., 60(3):191-4 (Jun. 2005).
Dunphy, J.E., ed., et al., "Current Surgical Diagnosis & Treatment" 5th ed., pp. 946-951, with 5 additional sheets, Lange Medical Publications, Los Altos, CA (1981).
British Pharmacopoeia, vol. II, pp. 903-940, London (1980).
British Pharmacopoeia 1980, pp. A81, 542, 546-549, with annotations, London—Addendum (1986).
Wagner, D.R., et al., "Combined parenteral and enteral nutrition in severe trauma," Nutrition in Clinical Practice, 7:113-116 with additional sheet, (1992).
Krizek, T.J., et al., "The use of prophylactic antibacterials in plastic surgery: A 1980s update," Plast. Reconstr. Surg., 76(6): 953-962, (Dec. 1985).
Healing of Full Thickness Defects in Swine.
Webster, J.G., "Prevention of Pressure Sores", © IOP Publishing Ltd 1991, The Adam Hilger Series on Biomedical Engineering, pp. 199-223.
Garcia-Velasco, M., et al., "Compression Treatment of Hypertrophic Scars in Burned Children", The Canadian Journal of Surgery, V.21, No. 5, Sep. 1978, pp. 450-452.
Rose, M.P., et al., "The Clinical Use of a Tubular Compression Bandage, Tubigrip, for Burn-Scar Therapy: A Critical Anaylis", Burns (1985) 12, 58-64.
Murray, Y., "Tradition Rather Than Cure", Wound Care, Nursing Times, Sep. 21, vol. 84, No. 38, 1988.
Spurlock, Gareth, "The Management of Open Joint Injuries", Wound Management, Veterinary Clinics of North American Equina Practice, vol. 5, No. 3, Dec. 1989.
Tittel, K., et al., "VariDyne—new standards in postoperative wound drainge", Jahrgang 14 (1988), Nr. 2, April, vol. 14 (1988), No. 2, April, pp. 104-107.
Queen, D., et al., "The preclinical evaluation of the Water Vapour Transmission Rate Through Burn Wound Dressings", Biomaterials 1987 vol. 8, September, pp. 367-371.
Wood, R.A.B., et al., "Foam Elastomer Dressing in the Management of Open Granulating Wounds: Experience with 250 Patients", Br. J. Surg., vol. 64 (1977), pp. 554-557.
Waymack, J.P., et al., "An Evaulation of Aquaphor Gauze Dressing in Burned Children", Burns (1986) 12, 443-448.
Winter, George D., "Epidermal Wound Healing Under a New Polyurethane Foam Dressing (Lyofoam)", Plastic & Reconstructive Surgery, Nov. 1975, Vo. 56, No. 5, pp. 531-537.
Proto, Massachusetts General Hospital Dispaches from the Frontiers of Medicine, 2 sheets, (Winter 2006).
Powell, E.T., "The role of negative pressure wound therapy with reticulated open cell foam in the treatment of war wounds," J. Orthop. Trauma, vol. 22(10) Supp.: S138-S141, (Nov./Dec. 2008).
"Negative pressure wound therapy devices," Technology assessment report; Agency for Healthcare Research and Quality, with annotations, website dated May 26, 2009, printed Jun. 26, 2009 and Jun. 28, 2009.
Thomas, S., "Atraumatic dressings," World Wide Wounds, sponsored by Molnylcke Health Care, 11 sheets, published Jan. 2003, website printout dated Jun. 29, 2009.
Orgill, D.P., et al., "The mechanisms of action of vacuum assisted closure: More to learn," Surgery, 146(1):40-51, (Jul. 2009).
Defranzo, A., et al., "4: Vacuum-assisted closure in extremity trauma," in Soft Tissue Surgery, S.L. Moran et al., p. 49-60 and additional sheet, Lippincott Williams & Wilkins (Pub. Apr. 1, 2008).
Stoeckel, W.T., et al., "30: Vacuum assisted devices for difficult wounds of the face and neck," Essential Tissue Healing of the Face and Neck, p. 399-408, and additional sheet, Horn, et al., (Pub. Jan. 28, 2009).
Demorest, R.L., "New standards in water vapour permeability testing," British Plastics & Rubber, 3 sheets, (handwritten label on first sheet shows "Exhibit TT"), (May 1995).
Kirk-Othmer, Encyclopedia of Chemical Technology, 2nd completely revised edition, vol. 9, pp. 220-232, John Wiley & Sons, Inc., (1966).
Stedman's Medical Dictionary, 25th ed., pp. 1739, Williams & Wilkins, (1990).
Standard Operating Procedure, The determination of moisture vapour permeability (MVP) and water transmission rate (WTR), implementation date: Sep. 11, 2006 and QA Operational Laboratories Analytical Report dated Nov. 13, 2008.
British Pharmacopoeia Selections: (1988) vol. II, p. 1126-1127, A223-A224; Addendum 1992, p. 1494; (1993) vol. II, p. 1266, A218-A219.
Solovev, V.A., "Treatment and prevention of suture failures after gastric resection," Dissertation abstract, with alleged index card, S.M. Kirov Gorky State Medical Institute, Gorky, U.S.S.R., (Exhibit I of Third party comments) (1988).
Solovev, V.A., "The method of treatment of immature external fistulas in the upper gastrointestinal tract," S.M. Kirov Gorky State Medical Institute, Gorky, U.S.S.R., (Exhibit J of Third party comments) (1987).
Thomas, S., "Wound Management and Dressings," The Pharmaceutical Press, London, 223 sheets, (1990).
Wood, R.A.B., et al., "A new method for treatment of open granulating wounds," Surgical Dressings in the Hospital Environment, T.D. Turner, ed., et al., Surgical Dressings Research Unit, Welsh School of Pharmacy, Uwist, Cardiff, 8 sheets, (1975).
Turner, T.D., ed., et al., Advances in Wound Management, including "The role of foam dressings in wound management" by S. Thomas, "Clinical aspects of Synthaderm®" by T. Martin, et al., "Lyofoam®—Used in the treatment of leg ulcers" by J. Creevy, and "Clinical experience of Silastic® foam dressing," by K.G. Harding; John Wiley & Sons, 17 sheets, (Proceedings dated Mar. 20-21, 1985) (1986).
PCT/US08/30581—International Report on Patentability (Jul. 22, 2010).
U.S. Appl. No. 12/351,331—Official Action (Dec. 21, 2011).
Parikh, R.S., et al., "Self-adhesive drape (Opsite) for management of leaking abdominal wounds", Indian J. Gastroenterol., 19(4):178-180 (Oct./Dec. 2000).
Alexis, A.F., et al., "Reassessment of the suction blister model of wound healing: introduction of a new higher pressure device", Int. J. Dermatol., 38(8):613-617 (Aug. 1999).
Gnanaraj, J., "A simple, sterile, low-cost, closed suction drainage system", Trop. Doct., 27(2):104 (Apr. 1997).
Klemm, K.W., "Antibiotic bead chains", Clin. Orthop. Rel. Res., (295):63-76 (Oct. 1993).
Pignatti, M., et al., "Mobile-VAC for the treatment of lower limb ulcers", Plast. Reconstr. Surg., 108(6):1837-1838 (Nov. 2001).
Schaum, K.D., "Payment strategies: a new medicare part B wound care policy", Adv. Skin & Wound Care, 14 (5):238-240 (Sep./Oct. 2001).

(56) References Cited

OTHER PUBLICATIONS

Chariker, M.E., Presentation entitled, "Vacuum therapy in wound management", (Chariker deposition exhibit No. 1220), dated Oct. 27, 2005.
Chariker, M.E., Presentation entitled, "Closed wound suction", (Chariker deposition exhibit No. 1219), dated Mar. 17, 2005.
Argenta, P.A., et al., "Vacuum-assisted closure in the treatment of complex gynecologic wound failures," Obstet. Gynecol., 99(3):497-501, (9 sheets) (Mar. 2002).
Azad, S., et al., "Topical negative pressure may help chronic wound healing" B.M.J., 324:1100 (1 sheet) (May 4, 2002).
Ballard, K., et al., "Developments in wound care for difficult to manage wounds," Br. J. Nurs., 9(7):405-8,410,412 (Apr. 13-26, 2000).
Ballard, K., et al., "Vacuum-assisted closure," Nurs. Times, 97(35):51-2 (5 sheets) Aug. 30-Sep. 5, 2001.
Ballard, K., et al., "Use of vacuum-assisted closure therapy following foot amputation," Br. J. Nurs., 10(15 Supplement):S6, 8, 11-12 (Aug. 2001).
Banwell, P.E., "Topical negative pressure therapy in wound care," J. Wound Care, 8(2):79-84 (Feb. 1999).
Bartels, C.G., et al., "The vacuum sealing technique. A new approach to cover soft tissue defects, used after the resection of a leiomyosarcoma", (English abstract on 2nd page and 1 page printout from PubMed); Hautarzt, 52 (7):653-7 (Jul. 2001).
Bauer, P., et al., "Possibilities of preliminary treatment of infected soft tissue defects by vacuum sealing and PVA foam", (English abstract on first page and 1 sheet PubMed abstract), Handchir. Mikrochir. Plast. Chir., 30(1):20-3 (Jan. 1998).
Baynham, S.A., et al., "Treating stage IV pressure ulcers with negative pressure therapy: a case report", Ostomy Wound Manage., 45(4):28-32, 34-35 (Apr. 1999).
Birchall, L., et al., "Developing a trust-wide centralised approach to the use of TNP", J. Wound Care, 11(8):311-4 (Sep. 2002).
Brody, G.S., "Biological creep", Plast. Reconstr. Surg., 92(6):1202-1203 (Nov. 1993).
Campton-Johnston, S., et al., "Infected wound management: advanced technologies, moisture-retentive dressings, and die-hard methods", Crit. Care Nurs. Q, 24(2):64-77 (Aug. 2001).
Chen, K.D., et al., "Mechanotransduction in response to shear stress", J. Biol. Chem., 274(26):18393-18400, (Jun. 25, 1999).
Clare, M.P., et al., "Experience with the vacuum assisted closure negative pressure technique in the treatment of non-healing diabetic and dysvascular wounds", Foot Ankle Int., 23(10):896-901 (Oct. 2002).
Claxton, M.J., et al., "Healing the diabetic wound and keeping it healed: modalities for the early 21st century", Curr. Diab. Rep., 2(6):510-B (Dec. 2002).
Coggrave, M., et al., "Topical negative pressure for pressure ulcer management", Br. J. Nurs., 11(6 Suppl):S29-31, S33-34, S36 (Mar. 2002).
Collier, M., "Know how: Vacuum assisted closure (VAC)", Nurs. Times, 93(5):32-3 (Jan. 29-Feb. 4, 1997).
Cooper, S.M., et al., "Topical negative pressure", Int. J. Dermatol., 39(12):896-8 (Dec. 2000).
Cozart, R.F., et al., "The use of controlled subatmospheric pressure to promote wound healing in preparation for split-thickness skin grafting in a fourth degree burn", Tenn. Med., 92(10):382-4 (Oct. 1999).
Cro, C., et al., "Vacuum assisted closure system in the management of enterocutaneous fistulae," Postgrad. Med. J., 78(925):364-5 (Nov. 2002).
De Filippo, R.E., et al., "Stretch and growth: the molecular and physiologic influences of tissue expansion". Plast. Reconstr. Surg., 109(7):2450-2462 (Jun. 2002).
Deva, A.K., et al., "Vacuum-assisted closure of a sacral pressure sore", J. Wound Care, 6(7):311-312, (Jul. 1997).
Dunford, C., "Hypergranulation tissue", J. Wound Care, 8(10):506-507 (Nov. 1999).

Dunford, C.E., "Treatment of a wound infection in a patient with mantle cell lymphoma", Br. J. Nurs., 10(16):1056, 1060, 1062, 1064-5 (Sep. 13-26, 2001).
Espensen, E.H., et al., "Use of subatmospheric (VAC) therapy to improve bioengineered tissue grafting in diabetic foot wounds", J. Am. Podiatr. Med. Assoc., 92(7):395-7 (Jul.-Aug. 2002).
Fleck, T.M., et al., "The vacuum-assisted closure system for the treatment of deep sternal wound infections after cardiac surgery", Ann. Thorac. Surg., 74(5):1596-600 (Nov. 2002).
Fleischmann, W., et al., "Vacuum assisted closure of wounds following dermatofasciotomy of the leg", Unfallchirurg., (English abstract on p. 284, and 1 sheet printout from PubMed); 99(4):283-7, (Apr. 1996).
Ford, C.N., et al., "Interim analysis of a prospective, randomized trial of vacuum-assisted closure versus the healthpoint system in the management of pressure ulcers", Ann. Plast. Surg., (11 sheets); 49(1):55-61 (Jul. 2002).
Gouttefangeas, C., et al., "Functional T lymphocytes infiltrate implanted polyvinyl alcohol foams during surgical wound closure therapy," Clin. Exp. Immunol., 124(3):398-405 (Jun. 2001).
Greer, S.E., et al., "Subatmospheric pressure dressing for saphenous vein donor-site complications," Ann. Thorac. Surg., (6 sheets); 71(3):1038-40 (Mar. 2001).
Hawkins-Bradley, B., et al., "Treatment of a nonhealing wound with hypergranulation tissue and rolled edges", J. Wound Ostomy Continence Nurs., 29(6):320-324 (Nov. 2002).
Harlan, J.W., "Treatment of open sternal wounds with the vacuum-assisted closure system: a safe, reliable method", Plast. Reconstruct. Surg., 109(2):710-12 (Feb. 2002).
Hartnett, S., "Heparin-induced thrombocytopenia as the cause of gluteus muscle necrosis: a case study describing the benefits of multidisiplinary physical and psychosocial interventions", Ostomy Wound Manage., 47(5):18-26 (May 2001).
Hersh, R.E., et al., "A technique for the treatment of sternal infections using the vacuum assisted closure™ device", Heart Surg. Forum, 4(3):211-15 (2001).
Ingber, D.E., "Mechanical signaling and the cellular response to extracellular matrix in angiogenesis and cardiovascular physiology", Circ. Res., 91:877-887 (Nov. 15, 2002).
Kalailieff, D., "Vacuum-assisted closure: wound care technology for the new millennium", Perspectives, 22(3):28-9 (Fall 1998).
Kercher, K.W., et al., "Successful salvage of infected PTFE mesh after ventral hernia repair", Ostomy Wound Manage., 48(10):40-5 (Oct. 2002).
Kiernan, M., "The process of granulation and its role in wound healing", Community Nurse, 5(5):47-48 (Jun. 1999).
Kloth, L.C., "5 questions-and answers-about negative pressure wound therapy", Adv. Skin Wound Care, 15(5):226, 228-9 (Sep.-Oct. 2002).
Kusel, C., "Use of V.A.C. (vacuum-assisted closure) therapy in general surgery: problem wounds deprived of air", Pflege Z., (and 1 sheet printout from PubMed); 55(6):408-412 (Jun. 2002).
Labler, L., et al., "Vacuum sealing of problem wounds", Swiss Surg., (English abstract on first page, 1 sheet printout from PubMed); 8(6)266-7 (2002).
Marston, W.A., et al., "The efficacy and safety of Dermagraft in improving the healing of chronic diabetic foot ulcers: results of a prospective randomized trial", Diabetes Care, 26(6) 10 pp., (Exhibit 271) (Jun. 1, 2003).
Mendez-Eastman, S., "New treatment for an old problem: negative-pressure wound therapy", Nurs., 32(5):58-64. (12 sheets) (May 2002).
Muller, G., "Vacuum dressing in septic wound treatment", Langenbecks Arch. Chir. Suppl. Kongressbd., (English abstract on p. 537, and 1 sheet printout from PubMed); 114:537-41 (1997).
McGuinness, J.G., et al., "Vacuum-assisted closure of a complex pilonidal sinus", Dis. Colon Rectum, 46(2):274-6 (Feb. 2003).
Moran, S.G., et al., "Vacuum-assisted complex wound closure with elastic vessel loop augmentation: a novel technique", J. Wound Care, 12(6):212-3 (Jun. 2003).
Schipper, J., et al., "The preconditioning and prelamination of pedicled and free microvascular anastomised flaps with the technique

(56) References Cited

OTHER PUBLICATIONS of vacuum assisted closure", Laryngorhinootologie, (English abstract on first page, and 2 sheets printout from PubMed); 82(6). 421-7, (Jun. 2003).
Shi, B., et al., "Effects of vacuum-assisted closure (VAC) on the expressions of MMP—1, 2, 13 in human granulation wound", Zhonghua Zheng Xing Wai Ke Za Zhi, (English abstract on first page and 1 sheet printout from PubMed); 19 (4):279-81 (Jul. 2003).
Silver, F.H., et al., "Mechanobiology of force transduction in dermal tissue", Skin Res. Technol., 9(1):3-23 (Feb. 2003).
Silver, F.H., et al., "Mechanosensing and mechanochemical transduction: how is mechanical energy sensed and converted into chemical energy in an extracellular matrix?" Crit. Rev. Biomed. Eng., 31(4):255-331 (2003).
Skillman, J., et al., "Vacuum assisted closure (VAC) dressing for skin graft application following exenteration of the orbit", Orbit, 22(1):63-5 (Mar. 2003).
Song, D.H., et al., "Vacuum assisted closure for the treatment of sternal wounds: the bridge between debridement and definitive closure", Plast. Recontr. Surg., 111(1):92-7 (Jan. 2003).
Wanner, M.B., et al., "Vacuum-assisted wound closure for cheaper and more comfortable healing of pressure sores: a prospective study", Scand. J. Plast. Reconstruct. Surg. Hand Surg., 37(1):28-33 (2003).
Weaver, B. "The nursing needs of a patient with a complicated abdominal wound", Prof. Nurse, 18(5):269-73 (Jan. 2003).
Wongworawat, M.D., et al., "Negative pressure dressings as an alternative technique for the treatment of infected wounds", Clin. Orthop. Relat. Res., (414):45-8 (Sep. 2003).
Baker, E.A., et al., "Growth factor profiles in intraperitoneal drainage fluid following colorectal surgery: relationship to wound healing and surgery", Wound Rep. Reg., 11(4):261-267, (Jul.-Aug. 2003).
Alberty, A., et al., "Effects of distraction and compression on proliferation of growth plate chondrocytes. A study in rabbits.", Acta Orthop. Scand., (1 sheet printout from PubMed): 64(4):449-455 (Aug. 1993).
Juchli, L., "Krankenpflege [Nursing] Practice and Theory of Promoting Health and Patient Care," Georg Theme Verlag Stuttgart, labeled as "Anlage 6.1" 1991 (allegedly dated Feb. 1991), and email dated May 30, 2007 labeled as "Anlage 6.2," both in German with English translations.
Fleischmann, W., et al., "Combination osteosynthesis in the treatment of pylon fractures with soft tissue damage," labeled "Anlage NK10," pp. 178-181 and showing "6. German-Austrian-Swiss Trauma Conference in Vienna May 21-25, 1991," published in "Der Unfallchirurg" [The Traumatologist] in 1993, in German with English translation.
"Coldex," labeled as "Anlage NK12" in German with English translation.
Turner, T.D., et al., eds., Excerpts from "Advances in wound management," including "Recent advances in wound management products" by T.D. Turner and "The role of foam dressings in wound management" by S. Thomas, Proceedings of a symposium held at the Welsh School of Pharmacy, University of Wales Institute of Science and Technology, Cardiff, Mar. 20-21, 1985, labeled as "Anlage NK13," 1986.
Fleischmann, W., et al., "Combination osteosynthesis in treating pilon fractures involving soft tissue injuries," in "Translation of an excerpt from the brochure regarding the Sixth German-Austrian-Swiss Accident Congress" allegedly dated 1991, in German with English translation.
ISO 10079-1, "International Standard," "Medical suction equipment—Part 1: electrically powered suction equipment—Safety requirements," dated May 15, 1991.
Moues, C.M., et al., "An economic evaluation of the use of TNP on full-thickness wounds", J. Wound Care, 14 (5):224-7 (May 2005).
Lee, S.S., et al., "Management of intractable sternal wound infections with topical negative pressure dressing", J. Card. Surg., 20(3):218-22 (May-Jun. 2005).

Jethwa, P., et al., "Using topical negative pressure therapy to resolve wound failure following perineal resection", J. Wound Care, 14(4):166-7 (Apr. 2005).
Banwell, P.E., et al., "Topical negative pressure therapy: mechanisms and indications", Int. Wound J., 1(2):95 (15 pages) (Jun. 2004).
Melano, E., et al., "The effects of Panafil when using topical negative pressure to heal an infected sternal wound,"J. Wound Care, 13(10):425-6 (Nov. 2004).
Morton, N., "Use of topical negative pressure therapy in postoperative dehisced or infected wounds", J. Wound Care, 13(8):346-8 (Sep. 2004).
Moisidis, E., et al., "A prospective, blinded, randomized, controlled clinical trial of topical negative pressure use in skin grafting", Plast. Reconstr. Surg., 114(4):917-22 (7 sheets) (Sep. 15, 2004).
Tachi, M., et al., "Topical negative pressure using a drainage pouch without foam dressing for the treatment of undetermined pressure ulcers", Ann. Plast. Surg., 53(4):338-42 (7 sheets) (Oct. 2004).
Jones, S.M., et al., "Complications of topical negative pressure therapy in small-diameter wounds", Plast. Reconstr. Surg., 114(3):815-817 (5 sheets) (Sep. 1, 2004).
Loree, S., et al., "Is vacuum assisted closure a valid technique for debriding chronic leg ulcers?"J. Wound Care, 13 (6):249-52 (Jun. 2004).
Vogt, P.M., et al., "Several aspects of foam materials and their possible interactions with the wound surface in the vacuum therapy", Zentralbl. Chir., (English abstract on first page, 1 sheet printout from PubMed); 129 Suppl 1:S92-S94 (May 2004).
Haslik, W., et al., "The use of subatmospheric pressure to prevent burn wound progression: first experiences in burn wound treatment", Zentralbl. Chir., (English abstract on first page, and 1 sheet printout from PubMed); 129 Suppl. 1: S62-63 (May 2004).
Steenvoorde, P., et al., "Combining topical negative pressure and a Bogota bag for managing a difficult laparostomy", J. Wound Care, 13(4):142-3 (Apr. 2004).
Pullen, R., "Treatment of pressure sores in elderly patients", Z. Genrontol. Geriatr., (English abstract on first page, 1 sheet printout from PubMed); 37(2):92-9 (Apr. 2004).
Gottrup, F., "Optimizing wound treatment through health care structuring and professional education", Wound Repair Regen., 12(2):129-33 (Mar.-Apr. 2004).
(Anon.) "New best practice guidelines for managing pressure ulcers with negative pressure wound therapy published", Home Healthcare Nurse, 23(7):469 (one sheet) (Jul. 2005).
Stechmiller, J.K., et al., "Effect of negative pressure wound therapy on the expression of TNF-alpha, IL-1beta, MMP-2, MMP-3, and TIMP-1 in wound fluids of adults with pressure ulcers", Wound Repair Regen., 13(2):A16 (Mar.- Apr. 2005).
Snyder, R.J., "Negative pressure wound therapy (NPWT)/ vacuum-assisted closure® (VAC®) as an adjunct in the treatment of pyoderma gangrenosum", Wound repair and regeneration, 13:A29 (Mar. 2005).
Armstrong, D.G., et al., "Negative pressure wound therapy in treatment of diabetic foot wounds: a marriage of modalities", Ostomy Wound Manage., 50(4A suppl):9-12 (Apr. 2004).
Armstrong, D.G., et al., "Plantar pressure changes using novel negative pressure wound therapy technique", J. Am. Podiatr. Med. Assoc., 94(5):456-60 (Sep.-Oct. 2004).
Baharestani, M.M., "Negative pressure wound therapy: An examination of cost-effectiveness", Ostomy Wound Manage., 50(11A suppl):29S-33S (Nov. 2004).
Bernstein, B.H., et al., "Combination of subatmospheric pressure dressing and gravity feed antibiotic instillation in the treatment of post-surgical diabetic foot wounds: a case series,"parts 1 and 2, Wounds, 17(2):37-48 (23 sheets) (Feb. 2005).
Datiashvili, R.O., et al., "Negative pressure dressings: An alternative to free tissue transfers?"Wounds, 17 (8):206-212 (Aug. 2005).
De Leon, J., "Negative pressure wound therapy in pressure ulcer management", Ostomy Wound Manage., 51(2A suppl):3S-8S (Feb. 2005).
Dobke, M.K., et al., "A novel approach to acute infection of the glenohumeral joint following rotator cuff repair—a case series", Wounds, 17(6):137-40 (6 sheets) (Jun. 2005).

(56) References Cited

OTHER PUBLICATIONS

Dunbar, A., et al., "Addressing the pain: Silicone net dressings as an adjunct with negative pressure wound therapy", Ostomy Wound Manage., 51(4):18-20 (4 sheets) (Apr. 2005).
Etoz, A., et al., "The use of negative pressure wound therapy on diabetic foot ulcers: A preliminary controlled trial", Wounds, 16(8):264-9 (Aug. 2004).
Fife, C.E., et al., "Healing dehisced surgical wounds with negative pressure wound therapy", Ostomy Wound Manage., 50(4A suppl):28-31 (Apr. 2004).
Geller, S.M., et al., "Ulceration of pyoderma gangrenosum treated with negative pressure wound therapy", J. Am. Podiatr. Med. Assoc., 95(2):171-4 (Mar.-Apr. 2005).
Gray, M., et al., "Is negative pressure wound therapy effective for the management of chronic wounds?"J. Wound Ostomy Continence Nurs., 31(3):101-5 (May-Jun. 2004).
Gupta, S., et al., "A literature review of negative pressure wound therapy", Ostomy Wound Manage., 50(11A suppl):2S-4S (Nov. 2004).
Gupta, S., et al., "The perioperative use of negative pressure wound therapy in skin grafting", Ostomy Wound Mangage., 50(4A suppl):32-4 (Apr. 2004).
Gupta, S., et al., "Guidelines for managing pressure ulcers with negative pressure wound therapy", Adv. Skin Wound Care, 17(Suppl 2):1-16 (Nov.-Dec. 2004).
Huljev, D., et al., "Necrotizing fasciitis of the abdominal wall as a post-surgical complication: a case report", Wounds, 17(7):169-77 (10 sheets) (2005) (Posted Aug. 11, 2005).
Kaplan, M., "Negative pressure wound therapy in the management of abdominal compartment syndrome", Ostomy Wound Manage., 51(2A suppl):29S-35S (Feb. 2005).
Mendez-Eastman, S., "Determining the appropriateness of negative pressure wound therapy for pressure ulcers", Ostomy Wound Manage., 50(4A suppl):13-16 (Apr. 2004).
Mendez-Eastman, S., "Using negative-pressure for positive results", Nursing, 35(5):48-50 (May 2005).
Miller, M.S., et al., "Negative pressure wound therapy: 'A rose by any other name'", Ostomy Wound Manage., 51 (3):44-9 (11 sheets) (Mar. 2005).
Niezgoda, J.A., et al., "The economic value of negative pressure wound therapy", Ostomy Wound Manage., 51 (2A suppl):44S-47S (Feb. 2005).
Niezgoda, J.A., "Combining negative pressure wound therapy with other wound management modalities", Ostomy Wound Manage., 51(2A suppl):S36-8 (Feb. 2005).
Orgill, D.P., et al., "Guidelines for treatment of complex chest wounds with negative pressure wound therapy", Supplement B to Wounds: A Compendium of Clinical Research and Practice, (24 sheets) (Dec. 2004).
Orgill, D.P., "Utilizing negative pressure wound therapy on open chest/sternotomy wounds", Ostomy Wound Manage., 50(11A suppl):15S-17S (Nov. 2004).
Orgill, D.P., "Advancing the treatment options of chest wounds with negative pressure wound therapy", Ostomy Wound Manage., 51(2A suppl):39S-43S (Feb. 2005).
Page, J.C., et al., "Retrospective analysis of negative pressure wound therapy in open foot wounds with significant soft tissue defects", Adv. Skin Wound Care, 17(7):354, 356, 358-60, 362-64 (Sep. 2004).
Page, J.C., et al., "Negative pressure wound therapy in open foot wounds with significant soft tissue defects", Ostomy Wound Manage., 51(2A suppl):9S-14S (Feb. 2005); excerpted from Page, J.C., et al., "Retrospective analysis of negative pressure wound therapy in open foot wounds with significant soft tissue defects", Adv. Skin & Wound Care, 17(7):354-364, (2004).
Pattison, P.S., et al., "Case report: Using dual therapies—Negative pressure wound therapy and modified silicone gel liner—to treat a limb postamputation and dehiscence", Wounds, 17(8):233-40 (11 sheets) (Aug. 2005).

Ratliff, C.R., "Negative-pressure wound therapy. Adjunct relief for chronic wounds", Adv. Nurs. Pract., 12(7):47-9 (3 sheets) (Jul. 2004) (Issue date: Jul. 1, 2004).
Sarsam, S.E., et al., "Management of wound complications from cesarean delivery,"Obstet. Gynecol. Surv., 60 (7):462-73 (Jul. 2005).
Schaum, K.D., "Payment perspective: Negative pressure wound therapy pumps and ostomy supplies", Ostomy Wound Manage., 51(3):20-22 (2 sheets) (Mar. 2005).
Simman, R., et al., "A comparative histological study of skin graft take with tie-over bolster dressing versus negative pressure wound therapy in a pig model: a preliminary study [brief communication]", Wounds, 16(2):76-80 (7 sheets) (Feb. 2004).
Kuznetsov, V.A., et al., Report on Practical Application entitled "Method of vacuum-sorption treatment of purulent wounds," Kazan Municipal Hospital No. 8, (1 sheet in English, 1 sheet in Russian and certificate of translation dated Apr. 28, 2009), (allegedly dated May 19, 1986).
Alexander, J.W., et al., "Clinical evaluation of epigard, a new synthetic substitute for homograft and heterograft skin," J. of Trauma, 13:374-383, (1973).
Anon., "Standard Test Methods for Water Vapor Transmission of Materials," ASTM, Designation: E 96/E 96M-05, Published Jun. 2005, 11 sheets, (Exhibit D-184).
Byers, R.M., "Clinical effects of closed suction drainage on wound healing in patients with head and neck cancer,"Arch. Otolaryngol., vol. 108:723-6, (Nov. 1982).
Cesany, P., "Suction in the Treatment of Torpid Ulcerations," Rozhledy v chirurgii, 48-9, MINCO22894-MINCO22898, cover sheet and pp. 406-409 English abstract on p. 409 (1 sheet printout from PubMed) (Sep. 1969).
Chinn, S.D., "Closed wound suction drainage," J. Foot Surg., vol. 24: 76-81, (Jan.-Feb. 1985).
Email dated Jan. 14, 2002 with attachments, including "Report of Meeting with DG Consulting" dated Jan. 10, 2002, 5 sheets, (Exhibit D-157).
Westaby, S., "Treatment of purulent wounds and fistulae with an adhesive wound irrigation device," Annals of the Royal College of Surgeons, vol. 63: 353-6 (1981).
Hartz, R.R., et al., "Healing of the Perineal Wound," Arch. Surg., vol. 115, 471-474, (1980), (Exhibit D-395).
Mizuno, K., "Suctioning Sponge," Arch. Opthalmol., vol. 101:294, (Feb. 1983).
Morykwas, Laboratory Notebook pages and charts; 38 pages (Exhibit D-46) dated prior to Mar. 1993.
Morykwas, Laboratory notebook pages and charts, 16 sheets, (Exhibit D-286) dated prior to Mar. 1993.
Morykwas, Laboratory notebook pages and charts, 17 sheets, (Exhibit D-233) dated prior to Nov. 1991.
Morykwas, Laboratory notebook pages of charts, Aug. 29 and Dec. 19, 3 sheets, (Exhibit P-664) dated prior to Nov. 1991.
Nikolov, A., "Method of treatment of postphlebitic and varicose trophic ulcers on the lower extremities by vacuum [Vacuum treatment method in postphlebitic and varicose trophic ulcers of the lower extremities]," Khirurgiia, pp. 368-374, (English abstract on p. 371 and 1 sheet printout from PubMed) (1981).
Smith, S.R.G., "Surgical drainage", Br. J. Hosp. Med., 33(6):308-315 (Jun. 1985).
Svedman, "A dressing system providing fluid supply and suction drainage used for continuous or intermittent irrigation," Ann. Plast. Surg., vol. 17, 9 pages, (Aug. 1986).
Svedman, "Irrigation treatment in split thickness skin grafting of intractable leg ulcers," Scand. J. Plast. Reconstr. Surg., vol. 19:211-213, (1985).
Morykwas, Laboratory Notebook pages and charts; (D-46) dated prior to Nov. 1991.
Morykwas, Laboratory Notebook pages and charts; (D-286) dated prior to Nov. 1991.
Bagautdinov, N.A., "Variant of external vacuum aspiration in the treatment of purulent disease of soft tissue," pp. 94-96 and Introduction by V.E. Volkov and an opinion by V. V. Shutova dated Feb. 4, 2009, in Russian with English translation, with alleged card cata-

(56) References Cited

OTHER PUBLICATIONS logue card with English translation, and certification of translation dated Feb. 19, 2009, Current Problems in Modem Clinical Surgery, (1986).
Kuznetsov, V.A., "Vacuum and vacuum-sorption treatment of open septic wounds," in II All-union conference "Wounds and wound infection" "(Abstracts of presentations)" in Russian with English translation, and card with English translation, Moscow, Oct. 28-29, 1986. (Bagautdinov II).
Robson, M.C., et al., Chapter 10 "Wounds and wound healing," p. 107-114 in Essentials of General Surgery, P.F. Lawrence ed., Williams & Wilkins, (1988).
Robson, M.C., et al., Chapter 11 "Wounds and wound healing," p. 119-126 in Essentials of General Surgery, 2nd edition, P.F. Lawrence ed., Williams & Wilkins, (1992).
Smith, D.J. Jr., et al., Chapter 7 "Wounds and wound healing," p. 113-122 in Essentials of General Surgery, 3d edition, P.F. Lawrence ed., Lippincott Williams & Wilkins, (2000).
Talboy, G.E., et al., "Chapter 8: Wounds and wound healing," p. 147-161 in Essentials of General Surgery, B. Sun ed., Lippincott Williams & Wilkins, (2006).
Garrison, R.N., et al., "Chapter 9: Surgical infections," p. 163-179 in Essentials of General Surgery, B. Sun ed., Lippincott Williams & Wilkins, (2006).
Sumpio, B.E., et al., "Role of negative pressure wound therapy in treating peripheral vascular graft infections," Vascular, 16(4):194-200, (2008).
Taber's Cyclopedic Medical Dictionary, Edition 20, pp: 306-309, 728-729, 765, 1726, and 2006-2009. (2005).
Mills, N., Polymer Foams Handbook: engineering and biomechanics applications and design guide, pp. 2-3, (2007).
Bucknall, T.E., et al.. eds., "Sutures and dressings," p. 88-93 in Wound Healing for Surgeons, (1984).
Parker, S.P., ed., McGraw-Hill Dictionary of Scientific and Technical Terms. 5th ed., pp. 139, 533, 772, and 1672 (1994).
Alger, M.S.M., Polymer Science Dictionary, (4 sheets), Elsevier Science Publishers Ltd. (1989).
Stedman's Medical Dictionary, 25th ed., pp. 554, 667-668, and 1603-1604, Williams & Wilkins, (1990).
Webster's New World Dictionary of the American Language, pp. 1105, Simon & Schuster, Inc., (1984).
Transeal transparent wound dressing, DeRoyal, 4 sheets (2003).
Kuznetsov, V.A., "Vacuum and vacuum-sorption treatment of open septic wounds," in II All-union conference "Wounds and wound infections" "(Presentation abstracts)" in Russian with English translation dated Apr. 2, 2009, with table of contents, Moscow, Oct. 28-29, 1986.
British Pharmacopoeia 19, vol. II, p. 927 and p. 548 of 1986 addendum, (vol. II—1980, addendum—1986).
KCI, "The V.A.C. operations summary," 7 sheets, (1999).
Kanshin, N.N., "Closed treatment of suppurative processes by the method of active lavage drainage," Third Surgical Clinic of the N.V. Sklifosovkiy Moscow Scientific Research Institute of Emergency Care, pp. 18-23, (6 sheets in English, 6 sheets in Russian and English abstract on pp. 22-23), allegedly submitted 1979.
Lokhvitskii, S.V., et al., "External vacuum aspiration in the treatment of purulent disorders of the soft tissues," Inpatient Surgery Clinic of the Therapeutic Department at Karagandy Medical Institute, Municipal Hospital No. 1, Temirtau, pp. 130-134 (5 sheets English, 5 sheets Russian), allegedly submitted Sep. 22, 1982.
Ersh, Z. Ya., "Use of polyurethane foam for treating purulent cavities and wounds," Purulent Septic Unit of Hospital No. 35, (2 sheets English and 2 sheets Russian), allegedly submitted for publication Mar. 21, 1984.
3M™ Tegaderm™ Transparent film dressings—wound, Commonly asked questions, 4 sheets, (Jan. 2007).
Greene, A.K., et al., "Microdefomiational wound therapy," Ann. Plast. Surg., 56(4):418-422, (2006).
Bui, T.D., et al., "Negative pressure wound therapy with off-the-shelf components," Am. J. Surg., 192:235-237, (2006).

Larichev, A.B., et al., "Vacuum-therapy in the complex of treatment of festering wounds," Khirurgiia (Mosk.), 6:22-26, (13 sheets English translation, 5 sheets in Russian, English abstract on pp. 22), (2008).
Scherer, S.S., et al., "The mechanism of action of the vacuum-assisted closure device," Plast. Reconstr. Surg., 122: 786-797, (presented at the Wound Healing Society Meeting 2007 in Tampa, Florida, Apr. 28-May 1) (2008).
Marks, M.W., et al., "Principles & Applications of Vacuum Assisted Closure (VAC)" Plastic Surgery Secrets, 2nd ed., Mosby Elsevier, (2010).
Bonnamy, C., et al., "Use of the vacuum-assisted closure system for the treatment of perineal gangrene involving the abdominal wall", Ann. Chir., (English abstract on first page and 1 sheet PubMed abstract) 125(10):982-4 (Dec. 2000).
Wong, S.L., et al., "Loxoscelism and negative pressure wound therapy (Vacuum-assisted closure): a clinical case series," Am. Surg., 75:1128-1131, (Nov. 2009).
Covey, D.C. et al., "Orthopaedic war injuries: From combat casulty care to definitive treatment: A current review of clinical advances, basic science, and research opportunities," Instr. Course Lect. 57:65-86 (2008).
Pirela-Cruz, M.A., et al., "Management of large soft-tissue wounds with negative pressure therapy—lessons learned from the war zone," J. Hand Ther. 21:196-203, (2008).
Vertrees, A., et al., "Modem management of complex open abdominal wounds of war: A 5-year experience," J. Am. Coll. Surg., 207:801-809, (2008).
Geiger, S., et al.. "War wounds: Lessons learned from Operation Iraqi Freedom," Plast. Reconstr. Surg., 122:146-153, (2008).
Hospenthal, D.R., et al., "Guidelines for the prevention of infection after combat-related injuries," J. Trauma, 64(3): S211-S220, (2008).
Murray, C.K., et al., "Prevention and management of infections associated with combat-related extremity injuries," J. Trauma, 64(3):S239-S251, (2008).
Campbell, P.E., et al., "Retrospective clinical evaluation of gauze-based negative pressure wound therapy," Int. Wound J., 5(2):280-286, (2008).
Argenta, A., et al., "Deformation of superficial and deep abdominal tissues with application of a controlled vacuum", European Tissue Repair Society, Focus group meeting Topical Negative Pressure (TNP) Therapy, London UK (Dec. 4-6, 2003).
Vacuum Assisted Closure (V.A.C.(R)) Therapy: an overview of scientific, clinical, and cost effectiveness evidence, (19 sheets) KCI Licensing, Inc., 2009.
Merriam-Webster Online, "reepithelialization," printout of webpage dated Apr. 17, 2009.
Oxford English Dictionary Online, "deformable," "deform," and "flexible," printout of webpages dated Apr. 17, 2009.
Murphey, G.C., et al., "Depth of penetration of negative pressure wound therapy into underlying tissues," Wound Repair and Regeneration, 17:113-117 (2009).
Jargin, S.V., "Limited access to foreign medical literature in Russia," Chartered Institute of Library and Information Professionals Health Libraries Group Newsletter, 25(4):7-10, (Dec. 2008).
Website printout "Chemical of the week" polymers, 5 sheets, printout dated Apr. 17, 2009.
Chariker, M.E., et al., "An algorithmic approach to the use of gauze-based negative-pressure wound therapy as a bridge to closure in pediatric extremity trauma," Plast. Reconstr. Surg., 123:1510-1520, (2009).
Cornelius, M., "Care in the air Bringing the wounded closer to home," Plast Surg. Nurs., 29(3):165-168, (Jul.-Sep. 2009).
Kumar, A.R., et al., "Lessons from Operation Iraqi Freedom: Successful subacute reconstruction of complex lower extremity battle injuries," Plast. Reconstr. Surg., 123:218-229, (2009).
*Kinetic Concepts, Inc.*, et al., v. *Bluesky Medical Corporation*, et al., Civil Action No. SA-03-CA-0832-RF, U.S. District Court, W. Dist. of Texas San Antonio Div., Promotional Slide Presentation BlueSky Medical Negative Pressure Wound Care with Versatile 1 Presentation Presented by Penny Campbell and Shelly Burdette-Taylor 27 pages (dated Oct. 14, 2005).

(56) References Cited

OTHER PUBLICATIONS

Barillo, D., et al., "Management of Burns to the Hand", Wounds 15,(1):4-9, 2003 Health Management Publications, Inc., Posted Feb. 12, 2003.
Medical Technology & Innovation, "Medical Technology is Extending Life, Reducing Costs", vol. 1, Issue 46, Dec. 4, 2000.
Wu, Lisa C., et al., "Vacuum-Assisted Closure for the Treatment of Sternal Wounds: The Bridge Between Debridement and Definitive Closure", printout from www.plasticsurgery.org, 3 pages (printout dated Apr. 20, 2005).
Bertone, A., "Management of Exuberant Granulation Tissue", Wound Management, pp. 551-562 (Dec. 1989).
Taber's Cyclopedic Medical Dictionary, Edition 18, pp. 937, 942 and 1375.
Harris, Ann, et al., "Hypergranulation Tissue: a Nontraumatic Method of Management", Ostomy/Would Management, vol. 40, No. 5, Jun. 1994.
Webster's New Universal Unabridged Dictionary Deluxe Second Edition, p. 631.
Chariker-Jeter Technique Tutorial by Penny E. Campbell, Wound Care Solutions, 1 page tutorial chart.
Bluesky Medical, Negative Pressure Wound Therapy, Product Catalog Fall 2005, "Finally a choice . . . " 8 pages.
Chariker-Jeter Status Link from the website www.trademark.com/cbi-bin/tmlist, Oct. 14, 2005, 1 page.
Bluesky Medical Support, printout of webpages www.woundvacuum.com/Standard%20Pages/support.htm, Oct. 11, 2005, pp. 1-3.
Leaper, D.J., "The Wound Healing Process," Advances in Wound Management, T.D. Turner, et al., eds., pp. 7-16, New York: John Wiley and Sons, (1986).
Svedman, P. et al., "A dressing system providing fluid supply and suction drainage used for continuous or intermittent irrigation", Ann. Plast. Surg., 17(2):125-33 (Aug. 1986).
"Pressure equivalents," McGraw-Hill Encyclopedia of Science & Technology, 6th ed., New York, pp. 249, (1987).
Thomas, S., "Wound management and dressings," cover sheet, preface, sheet labeled "Chapter 5" and pp. 36-39 (1990).
Taber's Cyclopedic Medical Dictionary, 16th edition, pp. 613-614, 643, 679, 1444, and 1686-1688, (1989).
Parker, S.P., ed., McGraw-Hill Dictionary of Scientific and Technical Terms, 4th ed., pp. 1462, (1989).
Gove, P.B., ed., Webster's Third New International Dictionary Unabridged, pp. 869 and 2627 (1986).
Peacock, Jr., E.E., Wound Repair, 3d edition, W.B. Saunders Company pp. 12-14, pp. 38-51, Chapter 6 Repair of skin wounds, (1984).
Spartanburg Regional Medical Center Operative reports, 35 sheets, dated 1989.
Johnson, F.E., "Expanded use of suction drains," pp. 469 and 1 sheet of drawings (allegedly dated 1985).
Brossy, J.-J., "Foam elastomer dressings in surgery," SA Medical Journal, 59:559-560, (Apr. 1981).
Groves, A.R., et al., "Silastic foam dressing: an appraisal," Annals of the Royal College of Surgeons of England, vol. 67, pp. 117-118 and additional page, (1985).
Harding, K.G., et al., "Silastic foam dressing for skin graft donor sites—a preliminary report," Br. J. Plast. Surg., 33:418-421, (1980).
Malone, W.D., "Wound dressing adherence: a clinical comparitive study," Archives of Emergency Medicine, 4:101-105, (1987).
Moblvac II advertising materials, 4 sheets, allegedly dated 1984.
Bucknall, T.E. ed., et al., "Wound healing for surgeons," Introduction, Chapter 1 the healing wound, Chapter 2 Wound strength, Chapter 3 Factors affecting healing, Chapter 4 Sutures and dressings, Chapter 5 Clinical trials, Chapter 6 Skin healing and burns, and Chapter 7 the abdominal wall, (1984).
Brubacher, L.L., "To heal a draining wound," RN, 45(3):30-36 (Mar. 1982).
Dahlin, P.A., et al., "Cerebrospinal fluid leak because of pressure sore fistula in a quadriplegic," Spine, 12(1):72-75, (1987).

Downie, P.A., ed., Cash's textbook of medical conditions for physiotherapists, Chapter 1 Inflammation and healing, Chapter 2 Oedema, Chapter 19 Skin conditions, Chapter 20 Burns, B. Lippincott Co., (1979).
Ersh, Z. Ya., "Use of polyurethane foam for cleaning of purulent cavities and wounds," I.I. Grekov J. of Surg., 133 (9):134-135 and additional sheets (10 sheets in English and 5 sheets in Russian) (1984).
Fasol, P., et al., "The foil vacuum dressing for the treatment of infected skin defects," Acta Chir. Austriaca 116-118, (2 sheets English and 3 sheets German) (1976).
Gruendemann, B.J., et al., Alexander's Care of the patient in surgery, 8th ed., C.V. Mosby Co., pp. 138-139 (1987).
Kirk-Othmer Encyclopedia of chemical technology, 3d ed., vol. 8, pp. 201-203 (1979).
Kostyuchenok, B.M., et al., "Vacuum treatment of purulent wounds," Soviet Medicine, pp. 18-21, (4 sheets English, 4 sheets Russian, with English abstract on last page), (1984).
Kuzin, M.I., et al., "Method of vacuum treatment of wounds," Wounds and Wound Infection, pp. 348-350, (2 sheets) (1981).
Kuzin, M.I., ed., et al., "Vacuum treatment of a purulent wound," Wounds and Wound Infection, Handbook for Physicians, 2nd revised and supplemented ed., pp. 243-246, (3 sheets) (1990).
Tranchell, H.G., et al., Circulatory Ulcers a Physicial Approach, John Wright & Sons Ltd., Bristol, Foreword, I. Ulcers: a comparison, II. The ulcer, pp. 44-47, and 54-55, (1960).
Parish, L.C., et al., "The infected decubitus ulcer," Int. J. Dermatol., 28:643-647 (Dec. 1989).
Davydov, Y.A., et al., "Device and method for vacuum therapy of purulent lactation mastites," Khirurgiya, (4):131-132, (Apr. 1988).
Davidov, Y.A., et al., "Justifying the usage of forced early secondary sutures in treatment of purulent wounds by the vacuum therapy," Vestnik Chirugia 126-129, (2 sheets in English and 3 sheets in Russian) (Mar. 1990).
Davydov, Y.A., et al., "Pathogenic mechanisms of the effect of vacuum therapy on the course of the wound process," Khirurgiya, 6:42-47 (7 sheets English and 8 sheets Russian, with English abstract on pp. 46-47) (1990).
Davydov, Y.A., et al., "Bacteriological and cytological evaluation of vacuum therapy of purulent wounds", Vestnik khirurgii, 10:48-52, (5 sheets English, 5 sheets Russian, English abstract on pp. 52) (Received 1987).
Davydov, Y.A., et al., "Vacuum therapy in the treatment of purulent lactation mastitis," pp. 66-70 (5 sheets English, 5 sheets Russian, English abstract on pp. 70) (Received 1986).
Davydov, Y.A., et al., "Vacuum therapy in the treatment of acute purulent diseases of soft tissues and purulent wounds", Vest. Khir. 141(9):43-46 (6 sheets English, 6 sheets Russian, English abstract on pp. 46) (1988).
Bagautdinov, N.A., "Variant of external vacuum aspiration in the treatment of purulent diseases of soft tissues," Current Problems in Modern Clinical Surgery, Interdepartmental Collection, Cheboksary, pp. 94-96, and library card, in English and Russian, (KCI_Con00220647-59) (1986).
Kuznetsov, V.A., et al., "Vacuum and vacuum-sorption treatment of open purulent wounds," II All-Union Conference "Wounds and Wound Infections" Moscow, pp. 91-92, with library card and table of contents, in English and Russian, (KCI_Con00220660-89) (1986).
Williams, R.S., "A simple technique for successful primary closure after excision of pilonidal sinus disease," Ann. R. Coll. Surg. England, 72:313-315, (only 2 sheets provided), (1990).
Gray, A.J., et al., "Small bowel perforation following vacuum suction drainage," J. R. Coll. Surg. Edinb. 30(5):324-5 and additional sheet, (Oct. 1985).
Kumar, A.R., "Standard wound coverage techniques for extremity war injury," J. Am. Acad. Orthop. Surg., 14:S62-S65, (2006).
Helgeson, M.D., et al., "Bioartificial dermal substitute: A preliminary report on its use for the management of complex combat-related soft tissue wounds," J. Orthop. Trauma, 21(6):394-399, (Jul. 2007).
Ingari, J.V., et al., "Civilian and detainee orthopaedic surgical care at an air force theater hosptial," Tech. Hand Upper Extr. Surg., 11(2):130-134, (2007).

(56) References Cited

OTHER PUBLICATIONS

Covey, D.C., "Combat orthopaedics: A view from the trenches," J. Am. Acad. Orthop. Surg., 14:S10-S17, (2006).
Andersen, R.C., et al., "Definitive treatment of combat casulties at military medical centers," J. Am. Acad. Orthop. Surg., 14:S24-S31, (2006).
Wagner, D. R., et al., "Bioelectrical impedance as a discriminator of pressure ulcer risk," Adv. Wound Care, 9 (2):30-37, (1996).
Mulder, G.D., et al., "Prospective randomized study of the efficacy of hydrogel, hydrocolloid, and saline solution-moistened moistened dressings on the management of pressure ulcers," Wound Rep. Reg., 1:213-218, (1993).
Tintle, T.E., et al., "Early experience with a calcium alginate dressing," Ostomy/Wound Management, pp. 74-81, (May/Jun. 1990).
Jeter, K.F., et al., "Comprehensive wound management with a starch-based copolymer dressing," J. Enterostom. Ther., 13(6):217-225, (Nov.-Dec. 1986).
Winter, G.D., "Formation of the scab and the rate of epithelization of superficial wounds in the skin of the young domestic pig," Nature, No. 4812, p. 293-294 (Jan. 20, 1962).
Robson, M.C., et al., "Bacterial quantification of open wounds," Military Medicine, pp. 19-24, (Jan. 1969).
Jackson, D.M., "The diagnosis of the depth of burning," Br. J. Surgery, 40(164):588-596 and 7 additional sheets, (May 1953).
Morykwas, M.J., "38: Vacuum-assisted closure of wounds" in "Wound Healing," A. Falabella et al., eds., Taylor & Francis, NY, pp. 503-515, (2005).
DeFranzo, A.J., et al., "Vacuum assisted closure for the treatment of abdominal wounds," Clin. Plast. Surg. 33(2):.213-224 (Apr. 2006).
DeFranzo, A.J., et al., "Vacuum-assisted closure for defects of the abdominal wall," Plast. Reconstr. Surg., 121(3):832-839, (Mar. 2008).
Park, C.A., et al., "Breast asymmetry: presentation of a giant fibroadenoma," Breast J., 12(5):451-461, (2006).
Zannis, J., et al., "Comparison of fasciotomy wound closures using traditional dressing changes and the Vacuum-Assisted Closure device," Ann. Plast. Surg., 62(4):407-409, (Apr. 2009).
Thompson, J.T., et al., "Outcome analysis of helmet therapy for positional plagiocephaly using a three-dimensional surface scanning laser," J. Craniofasc. Surg., 20(2):362-365, (Mar. 2009).
Argenta, L.C., et al., "Advances in hemangioma evaluation and treatment," J. Craniofac. Surg., 17(4):748-755 (Jul. 2006).
Plikaitis, C.M., et al, "Neurocutaneous melanosis: clinical presentations," J. Craniofac. Surg., 16(5):921-925 (Sep. 2005).
David, L.R., et al., "Proboscis lateralis: a rare craniofacial anomaly, reconstruction, and long-term evaluation," J. Craniofac. Surg., 19(4):1107-1113, (Jul. 2008).
Sanger, C., et al., "Dynamic spring mediated cranioplasty in an experimental model with resorbable foot plates," J. Craniofac. Surg., 18(1):54-59, (Jan. 2007).
Morykwas, M.J., et al., "Vacuum-assisted closure: state of basic research and physiologic foundation," Plast. Reconstr. Surg., 117(7) (Suppl): 121S-126S, (Jun. 2006).
Hill, C.A., et al., "Superior sternal cleft repair using autologous rib grafts in an infant with complex congenital heart disease," Ann. Thorac. Surg., 84:673-4, (2007).
McGee, M.P., et al., "Swelling and pressure-volume relationships in the dermis measured by osmotic-stress technique," Am. J. Physiol. Regul. Integr. Comp. Physiol., 296:R1907-R1913, (Mar. 25, 2009).
Morykwas, M., "Vacuum assisted closure," 91 sheets of slides.
Morykwas, M., et al., "El use de la plantilla de regeneracion integra en la cirugia reconstructiva," 121 sheets of slides.
Morykwas, M., et al., "Aplicaciones de tratamientos con presion sub-atmosferica en el cuidado de quemaduras," 140 sheets of slides.
Argenta, A., et al., "Deformation of superficial and deep abdominal tissues with application of a controlled vacuum", 1 sheet.
Banwell, P.E., et al., "Topical negative pressure (TNP): the evolution of a novel wound therapy," J. Wound Care, 12 (1):22-8 (Jan. 2003).
Cardozo, M., "A case study of holistic wound management in intensive care", Br. J. Nurs., 12(11 Suppl):S35-37, S40-42 (Jun. 2003).

Collier, M., "Topical negative pressure therapy", Nurs. Times, 99(5):54-5 (Feb. 4-10, 2003).
Domkowski, P.W., et al., "Evaluation of vacuum-assisted closure in the treatment of poststerotomy mediastinitis," J. Thorac. Cardiovasc. Surg., 126(2):386-90 (Aug. 2003).
Eginton, M.T., et al., "A prospective randomized evaluation of negative-pressure wound dressings for diabetic foot wounds", Ann. Vasc. Surg., 17(6):645-9 (2003).
Ferreira, M.C., et al., "The vacuum assisted closure of complex wounds: report of three cases", Rev. Hosp. Clin. Fac. Med. S. Paulo, 58(4):227-30 (2003).
Fisher, A., et al., "Vacuum assisted wound closure therapy", Issues Emerg. Health Technol., Issue 44, 6 pp. (Mar. 2003).
Hallberg, H., et al., "Vaginal construction with skin grafts and vacuum-assisted closure", Scand. J. Plast. Reconstr. Surg. Hand Surg., 37(2):97-101 (2003).
Hess, C.L., et al., "A review of mechanical adjuncts in wound healing: hydrotherapy, ultrasound, negative pressure therapy, hyperbaric oxygen, and electrostimulation", Ann. Plast. Surg., 51(2):210-8 (Aug. 2003).
Hodzic, J., et al., "Vacuum sealing of extensive wound healing disorders after kidney transplantation," Urologe A., (6 sheets in German, English abstract on p. 2 and 1 sheet printout from PubMed); 42(8):1097-100 (Aug. 2003) (Epub Apr. 3, 2003).
Kaufman, M.W., et al., "Vacuum-assisted closure therapy: wound care and nursing implications", Dermatol. Nurs., 15 (4):317-20, 323-236 (Aug. 2003).
Luckraz, H., et al., "Vacuum-assisted closure as a treatment modality for infections after cardiac surgery", J. Thorac. Cardiovasc. Surg., 125(2):301-5 (Feb. 2003).
Slides and photographs of patient treatment, 19 sheets, (Exhibit D-152) (allegedly dated 1987).
Slides, drawings, photographs of patient treatment and presentation slides, 20 sheets, (Exhibit D-151) (allegedly dated 1987).
Photographs of wound coverings and patient treatment, 16 sheets, (Exhibit D-240) (allegedly dated 1989).
Letter to Mr. Urs Tanner from Michael Baniak regarding: Updated Opinion of Non-infringement and Invalidity of Zamierowski U.S. Patent 4,969,880 and Argenta U.S. Patent 5,636,643, 30 pp., (Exhibit D-140) (dated Aug. 23, 2004).
Davydov, Y.A., et al., "The bacteriological and cytological assessment of vacuum therapy of purulent wounds", Vestnik Khirurgii imeni I.I. Grekova, (1 sheet of title page and pp. 48-52, 5 sheets of Russian text and English abstract on p. 52); 141(10):48-52, (Oct. 1988).
Davydov, Y.A., et al., "Bacteriological and cytological assessment of vacuum therapy of purulent wounds," (7 sheets of translation, pp. 48-52 of Russian text and English abstract on p. 52); 141(10):48-52 (Oct. 1988).
Davydov, Y.A., et al., "Vacuum therapy in the treatment of purulent lactation mastitis", Vestnik Khirurgii Imeni I.I. Grekova, (1 Sheet of Title page and pp. 66-70, 6 sheets of Russian text and English abstract on p. 70); 137 (11):66-70, (Nov. 1986).
Davydov, Y.A., et al., "Vacuum therapy in the treatment of purulent lactation mastitis", (8 sheets of English translation, pp. 66-70 of Russian text, and English abstract on p. 70); 137(11):66-70, (Nov. 1986).
Davydov, Y.A., et al., "Vacuum therapy in the treatment of acute purulent diseases of soft tissues and purulent wounds", (4 sheets of Translation, 4 sheets of Russian text and English abstract on p. 46); 141(9):43-46 (Sep. 1988).
Davydov, Y.A., et al., "Vacuum therapy in treatment of acute purulent diseases of soft tissues and purulent wounds," Vestnik Khirurgii (Surgeon's Herald), No. 9 Medicine Publishers, (5 sheets of translation), (1986).
Morykwas, M.J., "Use of sub-atmospheric pressure to prevent adriamycin extravasation ulcers in a pig model", first presented at the 44th Annual Meeting of Plastic Surgery Research Council, Pittsburg, PA, (May 22-26, 1999).
"The Remington Report: Business and clinical strategies for home care executives", containing articles by J.A. Molnar, D.G. Armstrong, et al., and S. Mendez-Eastman; (Nov. / Dec. 2004).
Molnar, J.A., "V.A.C. and burn care", presentation.

(56) References Cited

OTHER PUBLICATIONS

Slides regarding use of V.A.C.
Photographs showing patient treatment, "sheet 2", (Jeter deposition Exhibit 741) (allegedly dated 1985).
Egnell Minor, Instruction Book, First Edition allegedly dated Feb. 1987, 34 pages of English translation.
Addition to the "Users Manual Concerning Overflow Protection-Concerns all Egnell Pumps", dated Feb. 3, 1983, 2 pages of English translation.
M. Gosta Arturson, *The Pathophysiology of Severe Thermal Injury,* JBCR, 6(2):129-146 Mar.-Apr. 1985.
R. A.F. Clark et al., The Molecular and Cellular Biology of Wound Repair, Chapter 1 (1988).
Jeter, K.F. et al. (eds.), "Managing Draining Wounds and Fistulae: New and Established Methods," Chronic Wound Care: Health Management Publications, 1990, pp. 240-246.
Aeros, "Moblvac II."
Aeros, Aeros Instruments, Inc. 1111 Lakeside Drive, Gurnee, IL 60031. Aug. 1993. "Care-E-Vac."
Emerson, Series 55. J. H. Emerson Co., 22 Cottage Park Ave., Cambridge, MA 02140. "Emerson Post-Operative Suction Pumps."
Emerson, J. H. Emerson Co., (address: same as above). "Emerson Transport Suction Unit."
Aeros, Aeros Instruments, Inc. 3411 Commercial Ave., Northbrook, IL 60062. Oct. 1988. Part No. 1504-02 7M. "Instavac Aspirator."
"Pleur-evac. Adult-Pediatric, Non-Metered." Code Number: A-4000. Control Number: F7961J.
Instruction Manual, Creative Medical Laboratories, Inc. P.O. Box 6347, Rochester, Minn. 55903. "TUGS" (Transportable Universal Gradient Suction).
Deknatel, Div. of Howmedica, Inc. Quenns Village, NY 11429. "Pleur-evac."
Sparta Instrument Corp. 26602 Corporate Ave., Hayward, CA 94545. "Power Source Multi-Purpose Surgical Aspirator."
Wells Johnson Company, 2045 N. Forbes Blvd., Suite 106, Tucson, AZ. "Point 5 Aspirator."
Microtek Heritage, Inc. P.O. Box 2487, Columbus, MS 39704. "Wound-Evac ET."
Fleischmann, W. *Wund Forum Spezial.* IHW '94. "Vakuumversiegelung zur Behandlung von Probelmwunden" (with English translation: "Vacuum sealing for Treatment of Problematical Wounds."
Fleischmann, W. *Acta Orthopaedica Belgica.* vol. 58, Suppl. Jan. 1992 "Treatment of Bone and Soft Tissue Defects in Infected Nonunion."
Fleischmann, W. Strecker W, Bombelli M, Kinzl L. Unfall Chirurg. Springer-Variag 1993. 96:488-92 "Vakuumversiegelung zur Behandlung des Weichteilschadens bei offenen Frakturen." with English translation [Vacuum sealing as treatment of soft tissue damage in open fractures]. [German].
Valenta, A.L. *American Journal of Nursing.* Apr. 1994. "Using the Vacuum Dressing Alternative for Difficult Wounds." 94:44-5.
Bier, A., "Hyperemia by Suction Apparatus" Chapter VIII, Hyperemia as a Therapeutic Agent, Chicago, IL, Roberts Publishing, 74-85, (1905).
Saunders, J. W., The Lancet, pp. 1286-1287, Jun. 28, 1952, "Negative-Pressure Device for Controlled Hypotension during Surgical Operations".
Landis, et al., Robinette Foundation of the Hospital of the University of Pennsylvania, "The Effects of Alternate Suction and Pressure on Blood Flow to the Lower Extremities" (Sep. 1933).
Hargens et al., Space Physiology Laboratory, Life Science Division, NASA Ames Research Center, "Control of Circulatory Function in Altered Gravitational Fields" (Feb. 1992).
Wolthuis et al, Physiological Reviews, 54: 566-595, Jul. 1974, "Physiological Effects of Locally Applied Reduced Pressure in Man".
Viljanto et al., Br. J. Surg., 63: 427-430, 1976, "Local Hyperalimentation of Open Wounds".
Dillon, R. Angiology—The Journal of Vascular Diseases, pp. 47-56, Jan. 1986, "Treatment of Resistant Venous Stasis Ulcers and Dermatitis with the End-Diastolic Pneumatic Compression Boot".
Lundvall et al., Acta Physiol Scand, 136: 403-409, accepted Jan. 28, 1989, "Transmission of externally applied negative pressure to the underlying tissue. A study on the upper arm of man".
Klemp et al., The Journal of Investigative Dermatology, pp. 725-726 (1989), "Subcutaneous Blood Flow in Early Male Pattern Baldness".
A. Harle, Z. Orthop., 127: 513-517 (1989), "Schwachstellen herkommlicher Drainagen" with English Translation.
Dunlop et al., Br. J. Surg., 77: 562-563 (1990), "Vacuum drainage of groin wounds after vascular surgery: a controlled trail".
Maddin et al., International Journal of Dermatology, 29: 446-450 (1990), "The Biological Effects of a Pulsed Electrostatic Field with Specific Reference to Hair: Electrotrichogenesis".
Nakayama et al., Ann. Plast. Surg., 26:499-502 (1991), "A New Dressing Method for Free Skin Grafting in Hands".
Hargens et al., Aviation, Space and Environmental Medicine, pp. 934-937, Oct. 1991, "Lower Body Negative Pressure to Provide Load Bearing in Space".
Author unknown, Science, Sep. 1992, p. 42, "The Not-So-Bald-Truth".
Techno Takatsuki Co., Ltd., 8-16 Hatchonishimachi, Takatsuki City, Osaka, Japan, "HiBlow Air Pump".
Wells Johnson Company, 2045 N. Forbe Blvd., Suite 106, Tucson, AZ, "Suction Tips".
Industrial Equipment News, P.O. Box 1158, Skokie, IL 60076-9786, "Miscellaneous Equipment".
Letsou et al. "Stimulation of Adenylate Cyclase Activity in Cultured Endothelial Cells Subjected to Cyclic Stretch." Cardiovascular Surgery 3. Toronto. Sep. 1989. 634-639.
Bucalo et al. "Inhibition of Cell Proliferation by Chronic wound Fluid." Wound Repair and Regeneration. 181-186 Jul. 1993.
Falanga, Vincent. "Growth Factors and Chronic Wounds: The need to Understand the Microenvironment." Journal of Dermatology, Bol. 19: 667-672. 1992.
Urschel et al. "The Effect of Mechanical Stress on Soft and Hard Tissue Repair; a Review." British Journal of Plastic Surgery. 41, 182-186. 1988.
Gogia, Prem P. "The Biology of Wound Healing." Ostomy/Wound Management. Nov.-Dec. 1992. pp. 12, 14-16, 18-20, 22.
Wysocki et al. "Wound Fluid from Chronic Leg Ulcers Contains Elevated Levels of Metalloproteinases MMP-2 and MMP-9." The Society for Investigative Dermatology, Inc. Jul. 1993. 64-68.
Olenius et al. "Mitotic Activity in Expanded Human Skin." Plastic and Reconstructive Surgery. Feb. 1993. 213-216.
Mulder, G. D. et al. (eds.), *Clinicians' Pocket Guide to Chronic Wound Repair*, (Spartanburg, SC: Wound Healing Publications), 1991, pp. 54-55.
Chariker, M. E. et al. (eds), "Effective Management of Incisional and Cutaneous Fistulae with Closed Suction Wound Drainage," Contemporary Surgery, vol. 34, Jun. 1989, pp. 59-63.
Rastgeldi, S.: I. Pressure Treatment of Peripheral Vascular Diseases. II. Intermittent Pressure Treatment of Peripheral Vascular Diseases. Opuscula Medica, Suppl. XXVII, 1972.
OP-Journal Nr. 3, Jahr. 6, Dec. 1990, pp. 31-35 W. Fleischmann, M. Mentzel, L. Kinzl "BWS, Gefahren und Komplikationen der Therapie" with English Trans.
Zumtobel et al., (1991) "Wunddrainage in der Elektiveund Notfallchirurgie" Wolfgang Pabst Verlag, relevant p. 12, left column. English Translation attached.
Saechtling, Kunststoff-Taschenbuch, 24. Ausgabe 1989, S. 439, 477. English Translation attached.
Mutschler, W. Bakker D. J., "Temporarer Hautersatz", ZFA 1989, Heft 24, S. 714-720 als Sonderdruck. English Translation attached.
W. Fleischmann, U. Becker, M. Bischoff, H. Hoekstra, "Vacuum sealing: indication, technique, and results", Eur. J. Orthop & Traumato (1995) 5:37-40.
Argenta LC, Morykwas MJ. Vacuum-assisted closure: a new method for wound control and treatment: clinical experience. Ann Plast Surg 1997;38: 563-577.

(56) References Cited

OTHER PUBLICATIONS

Morykwas MJ, Argenta LC, Shelton-Brown EI, McGuirt W. Vacuum-assisted closure: a new method for wound control and treatment: animal studies and basic foundation. Ann Plast Surg 1997; 38:553-62.

Davydov IA, Larichev AB, Smirnov AP, Flegontov VB. Vakuum-terapiia v lechenii ostrykh gnoinykh zabolevanii miagkikh tkanei I gnoinykh ran. [Vacuum therapy of acute suppurative diseases of soft tissues and suppurative wounds]. Russian Vestnik Khirurgii Imeni I-I-Grekova 1988; 141: 43-6 with Eng.Trans.

Davydov IA, Abramov AI, Larichev AB. Vakuum-terapiia v preduprezhdenii posleoperatsionnoi ranevoi infektsii. [Vacuum therapy in the prevention of postoperative wound infection]. Russian Vestnik Khirurgii Imen I-I-Grekova 1991; 147:91-5, with English Translation.

Iankov NI. Simuliatsiia konsolidatsii perelomov nizhnei cheliusti vaktuumnoi terapiei. [Stimulation of consolidation of mandibular fractures by means of vacuum therapy] Russian. Stomatologiia 1971; 50: 86, with Eng. Trans.

Inoiatov IM, Aleksandrov VB. Lechenie promezhnostnoi rany posle amputatsii priamoi kishki vakuum-aspiratsiei. [Vacuum aspiration in the treatment of the perineal wound following extirpation of the rectum]. Russian. Khirurgiia 1971; 47: 74-8, with English Translation.

Kochnev VA. Primenenie vakuum-drenazhnoi sistemy dlia profilaktiki posleoperatsionnykh ranevykh oslozhnenii u bol'nykh opukholiami. [The use of a vacuum drainage system in the prevention of postoperative wound complications in tumor patients]. Russian. Voprosy Onkologii 1967; 13:102-5, w/Eng. Trans.

Mirazimov BM. Svobodnaia Kozhnaie plastika stopy s podgotovkoi ranevoi poverkhnosti vakumiravaniem [Free skin graft of the foot with vacuum preparation of the wound surface]. Russian. Orthopediia Travmatologiia I Protezirovanie 1966;27:19-22, with English Translation.

Mirazimov BM, Vasina TA, Mezhericher MI. Mikroflora dlitel'no nekazhivaiushchikh ran i effektivnost' metoda vakuumirovaniia. [Microflora of prolonged non-healing wounds and the effectiveness of the vacuum evaporative method]. Russian. Khirurgiia 1967; 43: 40-3, with English Translation.

Mirazimov BM. Vorbereitung von Wunden und Geschwuren zur Hautplastik unter Anwendung der Vakuumierung [Preparation of wounds and abcesses for dermatoplasty by means of a vacuum device]. German. Beitrage zur Orthopadie und Traumatologie 1967; 14:224-30, with Eng. Translation.

Netudykhatka O. Vliianie nizkogo dozirovannogo vakuuma na techenie reparativnogo protsessa v kostnoi tkani [Effect of low vacuum on the course of the reparative process in bone tissue]. Russian. Voprosy Kurortologii, Fizioterapii i Lechebnoi Fizicheskoi Kultury 1972; 37:411-5, w/Eng. Trans.

Volkov LA. Ispol'zovanie vakuum-drenazhnoi sistemy v khirurgicheskoi praktike. [Use of vacuum-drainage system in surgical practice]. Russian. Klinicheskaia Khirurgiia. 1973;7:54-5, with English Translation.

Teder H, Sanden G, Svedman P. Continuous Wound Irrigation in the Pig. J Invest Surg 1990;3:399-407.

Nakayama Y, Tomotari I, Soeda S. A New Method for the Dressing of Free Skin Grafts. Plast Reconstr Surg 1990;86:1216-1219.

Brock WB, Barker DE, Burns RP. Temporary Closure of open abdominal wounds: the vacuum pack. Amer Surg 1995;61:30-5.

Shein M, Saadia R, Jameson JR, Decker GAG. The "sandwich technique" in the Management of the Open Abdomen. Br J Surg 1986;73:369-70.

Broome A. Hansson L, Lundgren F, Smedberg S. Open Treatment of Abdominal Septic Catastrophies. World J. Surg 1983;7:792-6.

Vatanasapt V, Areemit S, Jeeravipoolvarn P, et al. Red rubber bulb, cheap and effective vacuum drainage. Journal of the Medical Association of Thailand 1989;72:193-7.

Brummelkamp WH, Taat CW, Slors JF. High-vacuum drainage and primary perineal wound closure in abdominoperineal excision of the rectum. Netherlands Journal of Surgery 1991;43:236-9.

Morykwas J, Argenta LC. Nonsurgical modalities to enhance healing and care of soft tissue wounds. Journal of the Southern Orthopaedic Association 1997;6:279-88.

Sames CP. Sealing of wounds with vacuum drainage [letter] Br Med J 1977;2:1123.

Greer SE, Longaker MT, Margiotta M. Preliminary Results from a Multicenter, Randomized, Controlled, Study of the Use of Subatmospheric Pressure Dressing for Pressure Ulcer Healing. Wound Repair and Regeneration 1999;7:255.

Greer SE, Longaker MT, Margiotta M, Matthews AJ, Kasabian A. The Use of Subatmospheric Pressure Dressing for the Coverage of Radial Forearm Free Flap Donor-Site Exposed Tendon Complications. Ann Plast Surg 1999;43:551-554.

Greer SE, Duthie E, Cartolano B, Koehler KM, Maydick-Youngberg D, Longaker MT. Techniques for Applying Subatmospheric Pressure Dressing to Wounds in Difficult Regions of Anatomy. JWOCN 1999;26:250-3.

Greer SE, Kasabian A, Thorne C, Borud L, Sims CD, Hsu M. The Use of Subatmospheric Pressure Dressing to Salvage a Gustilo Grade IIIB Open Tibia Fracture with Concomitant Osteomyelitis and Avert a Free Flap. Ann Plast Surg 1998;41:687.

Genecov DG, Schneider AM, Morykwas MJ, et al. A Controlled subatmospheric pressure dressing increases the rate of skin graft donor site reepithelialization. Ann Plast Surg 1998;40:219-25.

Mendez-Eastman S. Negative pressure wound therapy. Plastic Surgical Nursing 1998;18:27-9, 33-37.

Banwell P. Withey S, Holten I. The use of negative pressure to promote healing [letter; comment]. Brit J Plast Surg 1998;51:79.

Blackburn J H Boemi L, Hall WW. et al. Negative-pressure dressings as a bolster for skin grafts. Ann Plast Surg 1998;40:453-7.

Smith LA, Barker DE, Chase CW, et al. Vacuum Pack Technique of Temporary Abdominal Closure: A Four-Year Experience. Amer Surg 1997;63:1102-8.

McCulloch JM, Kemper CC. Vacuum-Compression Therapy for the Treatment of an Ischemic Ulcer. Physical Therapy 1993;73:165-9.

Mullner T, Mrkonjic L, Kwasny O, Vecsei V. The use of negative pressure to promote the healing of tissue defects: a clinical trial using the vacuum sealing technique [see comments]. Brit J Plast Surg 1997;50:194-9.

Mirazimov, B.M.: Free Skin Grafting of Wounds and Ulcers using the "Vacuum Treatment" Method. [Orthop. Travmatol. Protez., 28(1):54-58.] with English Trans. 1967.

Greer, Steven E., "Whither Subatmospheric Pressure Dressing?" The Institute of Reconstructive Plastic Surgery, The New York University Medical Center, New York, NY April Issue of Annals of Plastic Surgery 2000.

Registration No. 1982349. Owner, KCI Inc., 3440 E. Houston Street San Antonio Texas 78219. Source: United States Patent and Trademark Office official website. Filing date May 1, 1995 Registration Date Jun. 25, 1996.

Hidden Interest—A Special Report.; When Physicians Double as Entrepreneurs. The New York Times. 11pp. Nov. 30, 1999.

Defranzo, Anthony J., et al., "Vacuum-Assisted Closure for the Treatment of Degloving Injuries." Plastic and Reconstructive Surgery 104 (7) 2145-48: (1999).

Morykwas, Michael J., et al., "Use of Subatmospheric Pressure to Prevent Progression of Partial-Thickness Burns in a Swine Model". Journal of Burn Care & Rehabilitation 20 (1 Part 1): 15-21 (1999).

Morykwas, Michael J., et al., "Use of Subatmospheric Pressure to Prevent Doxorubicin Extravasation Ulcers in a Swine Model". Journal of Surgical Oncology 72:14-17 (1999).

Schneider, Andrew M., et al., "A New and Reliable Method of Securing Skin Grafts to the Difficult Recipient Bed". Plastic and Reconstructive Surgery 102(4) 1195-98 (1998).

Rosser, Charles J., et al., "A New Technique to Manage Perineal Wounds". Infections in Urology 13(2) 45-47, 56 (2000).

Philbeck, Thomas E., et al., "The Clinical and Cost Effectiveness of Externally Applied Negative Pressure Wound Therapy in the Treatment of Wounds in Home Healthcare Medicare Patients". Ostomy/Wound Management 45(11) 41-44, 46-50 (1999).

Meara, John G., et al., "Vacuum-Assisted Closure in the Treatment of Degloving Injuries". Annals of Plastic Surgery 42(6) 589-594 (1999).

(56) References Cited

OTHER PUBLICATIONS

Obdeijn, Miryam C., et al., "Vacuum-Assisted Closure in the Treatment of Poststernotomy Mediastinitis". Ann Thorac Surgery 68 2358-60 (1999).
Mendez-Eastman, Susan., "When wounds won't heal". RN 20-24 (1998).
Hartnett, Jacqueline M., "Use of Vacuum-Assisted Wound Closure in Three Chronic Wounds". JWOCN 25 (6) 281-290 (1998).
Mendez-Eastman, Susan., "Use of Hyperbaric Oxygen and Negative Pressure Therapy in the Multidisciplinary Care of a Patient with Nonhealing Wounds". JWOCN 26(2) 67-76 (1999).
Wooding-Scott, Margaret et al., "No-Wound is Too Big for Resourceful Nurses". RN, Dec. 22-25, 1988.
Davydov, et al., "Pathenogenic mechanism of the effect of vacuum therapy on the course of the wound process". Khirurgiia, Jun. 1990 (with English translation).
Davydov, et al., "Vacuum therapy in the treatment of suppurative lactation mastitis". Vestn. Khir., Nov. 1986 (with English translation).
Davydov, et al., "Bacteriological and cytological evaluation of the vacuum therapy of suppurative wounds". Vestn. Khir., Oct. 1988 (with English translation).
Davydov, et al., "Basis of the use of forced early secondary suture in the treatment of suppurative wounds by the vacuum therapy method". Vestn. Khir., Mar. 1990 (with English translation).
Borzov, et al., "Vacuum therapy of some skin diseases". Vestn. Dermatol. Venerol., Aug. 1965 (with English translation).
M.J. Morykwas and L.C. Argenta, "Techniques in Use of V.A.C. Treatment (in English)", Acta Chir. Austriaca Supplement Nr. 150, 1998, p. 3-4 of 2-28.
Garcia-Rinaldi, et al., "Improving the Efficiency of Wound Drainage Catheters", J. Surg., 1975, pp. 372-373.
Raffl, et al. "The Five Year Survival Rate for Gastric Cancer: Statistical Study from Syracuse Medical Center", Cancer, 6:756-759, Jul. 1953.
Raffl, et al., The Use of Negative Pressure Under Skin Flaps After Radical Mastectomy, Ann. Surg. 136: 1048, Dec. 1952.
Marie Knight, "A Second Skin for Patients with Large Drainage Wounds," Nursing 6(1) p. 37, 1976.
Oscar Ramirez, "Optimal Wound Healing under Op-Site Dressing" Plas. & Recon. Surg., 73(3): 474-475; 1984.
Helen Bibleheiner, "Dealing with a Wound that Drains 1.5 Liters per Day," RN Aug. 1986.
Peter Schwab, "Primary Closure of the Perineal Wound After Proctectomy" Mayo Clin. Proc., Mar. 1974, vol. 49.
PCT/US08/79364—Written Opinion and International Search Report (Dec. 16, 2008).
PCT/US08/79364—International Report on Patentability (Apr. 13, 2010).
PCT/US03/16763—Written Opinion, International Preliminary Examination Report, and International Search Report, (Dec. 18, 2003, Apr. 19, 2004, and Sep. 2, 2004).
PCT/US08/30581—Written Opinion and International Search Report (Feb. 20, 2009).
PCT/US09/50806—Written Opinion and International Search Report (Sep. 15, 2009).
PCT/US09/50806—International Report on Patentability (Jan. 27, 2011).
Van Susante, J.L.C., et al., "Linkage of chondroitin-sulfate to type I collagen scaffolds stimulates the bioactivity of seeded chondrocytes in vitro," Biomaterials, 22:2359-2369 (2001).
Wang, Y., et al., "A tough biodegradable elastomer," Nature Biotechnology, 20:602-606 (Jun. 2002).
Sasaki, N., et al., "Stress-strain curve and Young's Modulus of a collagen molecule as determined by the x-ray diffraction technique," J. Biomechanics, 29(5):655-658 (1996).
Nagata, M., et al., "Synthesis, characterization, and enzymatic degradation of network aliphatic copolyesters," Journal of Polymer Science: Part A: Polymer Chemistry, 37:2005-2011 (1999).

Causa, F., et al., "A multi-functional scaffold for tissue regeneration: The need to engineer a tissue analogue," Biomaterials, 28(34):5093-5099 (Dec. 2007; available online Aug. 6, 2007).
Nair, L.S., et al., "Development of novel tissue engineering scaffolds via electrospinning," Expert Opin. Biol. Ther. 4 (5):659-668 (May 2004), (2 sheets), abstract.
Webb, A.R., et al., "Biodegradable polyester elastomers in tissue engineering," Expert Opin. Biol. Ther. 4(6):801-812 (2004).
Zhong, S.P., et al., "Development of a novel collagen-GAG nanofibrous scaffold via electrospinning," Materials Science and Engineering: C, 27(2):262-266 (Mar. 2007) (available online Jun. 8, 2006).
Li, C., et al., "Electrospun silk-BMP-2 scaffolds for bone tissue engineering," Biomaterials, 27(16):3115-3124 (Jun. 2006) (available online Feb. 3, 2006).
Teo, W.E., et al., "Electrospun scaffold tailored for tissue-specific extracellular matrix," Biotechnology Journal, 1 (9):918-929 (Sep. 2006) (published online Aug. 28, 2006).
Yi, F., et al., "Poly(glycerol sebacate) nanofiber scaffolds by core/shell electrospinning," Macromol. Biosci. 8:803-806 (2008).
Wang, Y., et al., "In vivo degradation characteristics of poly(glycerol sebacate)," J. Biomed Mater Res A, 66 (1):192-197 (Jul. 1, 2003) (published online Jun. 10, 2003).
Ifkovits, J.L., et al., "Biodegradable and radically polymerized elastomers with enhanced processing capabilities," Blamed Mater. 3(3):034104 (Sep. 2008) (published Aug. 8, 2008).
Ekaputra, A.K., et al., "Composite electrospun scaffolds for engineering tubular bone grafts," Tissue Eng. Part A 15 (12):3779-3788 (Dec. 8, 2009) (published online Jul. 20, 2009; online ahead of print: Jul. 24, 2009; online ahead of editing: Jun. 15, 2009).
Schofer, M.D., et al., "Characterization of a PLLA-collagen I blend nanofiber scaffold with respect to growth and osteogenic differentiation of human mesenchymal stem cells," ScientificWorldJournal 9:118-129 (Feb. 15, 2009).
Venugopal, J.R., et al., "Nanobioengineered electrospun composite nanofibers and osteoblasts for bone regeneration," Artif. Organs 32(5):388-397 (2008).
Heydarkhan-Hagvall, S., et al., "Three-dimensional electrospun ECM-based hybrid scaffolds for cardiovascular tissue engineering," Biomaterials 29(19):2907-2914 (Jul. 2008; available online Apr. 9, 2008).
Chen, D., et al., "Application of electrostatic spinning technology in nano-structured polymer scaffold," Zhongguo Xiu Fu Chong Jian Wai Ke Za Zhi, 21(4):411-415 (Apr. 2007), 1 sheet abstract.
Qiu, H., et al., "A citric acid-based hydroxyapatite composite for orthopedic implants," Biomaterials 27:5845-5854 (2006) (available online Aug. 21, 2006).
Nair, L.S., et al., "Nanofibers and nanoparticles for orthopaedic surgery applications," J. Bone Joint Surg. Am. 90 (Supp. 1):128-131 (2008).
Abdel-Fattah, W.I., et al., "Synthesis, characterization of chitosans and fabrication of sintered chitosan microsphere matrices for bone tissue engineering," Acta Biomaterialia 3:503-514 (2007).
Li, M., et al., "Co-electrospun poly(lactide-co-glycolide), gelatin, and elastin blends for tissue engineering scaffolds," J. Biomed. Mater. Res. A. 79(4):963-973 (Dec. 15, 2006) (published online Aug. 31, 2006).
Li, M., et al., "Electrospun blends of natural and synthetic polymers as scaffolds for tissue engineering," Conf. Proc. IEEE Eng. Med. Biol. Soc. 6:5858-5861 (2005), 1 sheet abstract.
Yang, X., et al., "Multifunctional nanofibrous scaffold for tissue engineering," Journal of Experimental Nanoscience 3 (4):329-345 (2008).
Deng, M., et al., "Biomimetic, bioactive etheric polyphosphazene-poly(lactide-co-glycolide) blends for bone tissue engineering," J. Biomed Mater Res A 92:114-125 (2010; published online Jan. 22, 2009).
Roshi, R.A., "Nanoporous biodegradable elastomers," Adv. Mater. 21:188-192 (2009).
Yang, J., et al., "Synthesis and evaluation of poly(diol citrate) biodegradable elastomers," Biomaterials 27:1889-1898 (2006; available online Nov. 15, 2005).

(56) References Cited

OTHER PUBLICATIONS

Yoshimoto, H., et al., "A biodegradable nanofiber scaffold by electrospinning and its potential for bone tissue engineering," Biomaterials 24(12):2077-2082 (May 2003).
Ndreu, A., et al., "Electrospun biodegradable nanofibrous mats for tissue engineering," Nanomedicine (Lond.) 3 (1):45-60 (Feb. 2008), 1 sheet abstract.
Kim, S.S., et al., "Accelerated bonelike apatite growth on porous polymer/ceramic composite scaffolds in vitro," Tissue Eng. 12(10):2997-3006 (Oct. 2006).
Li, M., et al., "Electrospun protein fibers as matrices for tissue engineering," Biomaterials 26(30):5999-6008 (Oct. 2005) (available online May 13, 2005).
Kidoaki, S., et al., "Mesoscopic spatial designs of nano- and microfiber meshes for tissue-engineering matrix and scaffold based on newly devised multilayering and mixing electrospinning techniques," Biomaterials 26(1):37-46 (Jan. 2005) (available online Mar. 2, 2004).
Ma, Z., et al., "Potential of nanofiber matrix as tissue-engineering scaffolds," Tissue Engineering 11(1/2):101-109 (2005).
Faria, M.L.E., et al., "Recombinant human bone morphogenetic protein-2 in absorbable collagen sponge enhances bone healing of tibial osteotomies in dogs," Veterinary Surgery 36(2):122-131 (Feb. 2007; first published online Mar. 2, 2007).
Li, W.J., et al., "Fabrication and characterization of six electrospun poly(alpha-hydroxy ester)-based fibrous scaffolds for tissue engineering applications," Acta Biomater. 2(4):377-385 (Jul. 2006; published online May 6, 2006).
Smith, L.A., et al., "Nano-fibrous scaffolds for tissue engineering," Colloids and Surfaces B: Biointerfaces 39 (3):125-131 (Dec. 10, 2004; available online Feb. 4, 2004).
Smith, I.O., et al., "Nanostructured polymer scaffolds for tissue engineering and regenerative medicine," Interdisciplinary Reviews: WIREs Nanomed. Nanobiotechnol. 1(2):226-236 (Mar./Apr. 2009) (Jan. 12, 2009).
Dong, B., et al., "Electrospinning of collagen nanofiber scaffolds from benign solvents," Macromolecular Rapid Communications 30(7):539-542 (Feb. 5, 2009).
Wang, W., et al., "Biodegradable polyurethane based on random copolymer of L-lactide and ε-caprolactone and its shape-memory properly," J. Appl. Polym. Sci. 104:4182-4187 (2007).
Chen, Y., et al., "Increased osteoblast functions in the presence of BMP-7 short peptides for nanostructured biomaterial applications," J. Biomed. Mater. Res. A 91:296-304 (2009; published online Nov. 3, 2008).
Chronakis, I.S., "Novel nanocomposites and nanoceramics based on polymer nanofibers using electrospinning process—A review," Journal of Materials Processing Technology 167:283-293 (2005).
Guan, J., et al., "Preparation and characterization of highly porous, biodegradable polyurethane scaffolds for soft tissue applications," Biomaterials 26:3961-3971 (2005; available online Dec. 8, 2004).
Soletti, L., et al., "A bilayered elastomeric scaffold for tissue engineering of small diameter vascular grafts," Acta Biomaterialia 6:110-122 (2010; available online Jun. 18, 2009).
Kim, H.W., et al., "Bioactive glass nanofiber-collagen nanocomposite as a novel bone regeneration matrix," J. Biomed. Mater. Res. A 79:698-705 (2006; published online Jul. 18, 2006).
Nair, L.S., et al., "Biodegradable polymers as biomaterials," Prog. Polym. Sci. 32:762-798 (2007; available online Jun. 11, 2007).
Zhang, Y., et al., "Electrospun biomimetic nanocomposite nanofibers of hydroxyapatite/chitosan for bone tissue engineering," Biomaterials 29:4314-4322 (2008; available online Aug. 20, 2008).
Wan, Y., et al., "Biphasic scaffold for annulus fibrosus tissue regeneration," Biomaterials 29:643-652 (2008; available online Nov. 13, 2007).
Um, I.C., et al., "Electro-spinning and electro-blowing of hyaluronic acid," Biomacromolecules 5:1428-1436 (2004; published online May 7, 2004).
Boland, E.D., et al., "Electrospinning polydioxanone for biomedical applications," Acta Biomaterialia 1:115-123 (2005).
Ji, Y., et al., "Electrospun three-dimensional hyaluronic acid nanofibrous scaffolds," Biomaterials 27:3782-3792 (2006: available online Mar. 23, 2006).
Fujihara, K., et al., "Guided bone regeneration membrane made of polycaprolactone/calcium carbonate composite nano-fibers," Biomaterials 26:4139-4147 (2005; available online Dec. 24, 2004).
Krogman, N.R., et al., "The influence of side group modification in polyphosphazenes on hydrolysis and cell adhesion of blends with PLGA," Biomaterials 30:3035-3041 (2009: available online Apr. 5, 2009).
Sethuraman, S., et al., "Novel low temperature setting nanocrystalline calcium phosphate cements for bone repair: Osteoblast cellular response and gene expression studies," J. Biomed. Mater. Res. A 82:884-891 (2007; published online Mar. 2, 2007).
Deng, M., et al., "Miscibility and in vitro osteocompatibility of biodegradable blends of poly[(ethyl alanato) (p-phenyl phenoxy) phosphazene] and poly(lacitic acid-glycolic acid)," Biomaterials 29:337-349 (2008; available online Oct. 17, 2007).
Boissard, C.I.R., et al., "Nanohydroxyapatite/poly(ester urethane) scaffold for bone tissue engineering," Acta Biomaterialia 5:3316-3327 (Nov. 2009; available online May 12, 2009).
Shah, P.N., et al., "Electrospinning of L-tyrosine polyurethanes for potential biomedical applications," Polymer 50:2281-2289 (May 2009; available online Mar. 19, 2009).
Lu, X.L., et al., "Shape memory property of poly(L-lactide-co-ε-caprolactone) copolymers," Materials Science and Engineering A 438-440:857-861 (2006).
Leonelli, C., et al., "Synthesis and characterization of cerium-doped glasses and in vitro evaluation of bioactivity," Journal of Non-Crystalline Solids 316:198-216 (2003).
U.S. Appl. No. 12/351,331—Official action (Mar. 26, 2011).
Zheng ZL, Morykwas MJ, Campbell D, et al. Mechanical tissue resuscitation at the site of traumatic brain injuries reduces the volume of injury and hemorrhage in a Swine model. Neurosurgery, 2014. 75(2): pp. 152-1562. NPL-996.
Young, W., Methylprednisolone and spinal cord injury. J Neurosurg, 2002. 96(1 Suppl): pp. 141-142. NPL-997.
Basso, D.M., M.S. Beattie, and J.C. Bresnahan, A sensitive and reliable locomotor rating scale for open field testing in rats. J Neurotrauma, 1995. 12(1): pp. 1-21. NPL-998.
Bozzo A, Marcoux J, Radhakrishna M, Pelletier J, Goulet B. The role of magnetic resonance imaging in the management of acute spinal cord injury. J Neurotrauma, 2011. 28(8): p. 1401-1411. NPL-999.
Kozlowski P, Raj D, Liu J, Lam C, Yung AC, Tetzlaff W. Characterizing white matter damage in rat spinal cord with quantitative MRI and histology. J Neurotrauma, 2008. 25(6): pp. 653-676. NPL-1000.
Ramu J, Herrera J, Grill R, Bockhorst T, Narayana P. Brain fiber tract plasticity in experimental spinal cord injury: diffusion tensor imaging. Exp Neurol, 2008. 212(1): pp. 100-107. NPL-1001.
Ellingson, B.M., S.N. Kurpad, and B.D. Schmit, Ex vivo diffusion tensor imaging and quantitative tractography of the rat spinal cord during long-term recovery from moderate spinal contusion. J Magn Reson Imaging, 2008. 28(5): pp. 1068-1079. NPL-1002.
Yu C, Jagid J, Ruenes G, Dietrich WD, Marcillo AE, Yezierski RP. Detrimental effects of systemic hyperthermia on locomotor function and histopathological outcome after traumatic spinal cord injury in the rat. Neurosurgery, 2001. 49(1): pp. 152-158; discussion 158-9. NPL-1003.
Sundgren PC, Dong Q, Gomez-Hassan D, Mukherji SK, Maly P, Welsh R. Diffusion tensor imaging of the brain: review of clinical applications. Neuroradiology, 2004. 46(5): pp. 339-350. NPL-1004.
Vedantam A, Jirjis MB, Schmit BD. et al. Diffusion tensor imaging and tractography in Brown-Sequard syndrome. Spinal Cord, 2012. 50(12): pp. 928-930. NPL-1005.
Cohen-Adad J, Leblond H, Delivet-Mongrain H, Martinez M, Benali H, Rossignol S. Wallerian degeneration after spinal cord lesions in cats detected with diffusion tensor imaging. Neuroimage, 2011. 57(3): pp. 1068-1076. NPL-1006.
Jirjis, M.B., S.N. Kurpad, and B.D. Schmit, Ex vivo diffusion tensor imaging of spinal cord injury in rats of varying degrees of severity. J Neurotrauma, 2013. 30(18): pp. 1577-1586. NPL-1007.
Konomi T, Fujioshi K, Hikishima K, et al.Conditions for quantitative evaluation of injured spinal cord by in vivo diffusion tensor imaging

(56) References Cited

OTHER PUBLICATIONS and tractography: preclinical longitudinal study in common marmosets. Neuroimage, 2012. 63(4): pp. 1841-1853. NPL-1008.
Harsan LA, Poulet P, Guignard B, Parizel N, Skoff RP, Ghandour MS. Astrocytic hypertrophy in dysmyelination influences the diffusion anisotropy of white matter. J Neurosci Res, 2007. 85(5): pp. 935-944. NPL-1009.
Jones, D.K., T.R. Knosche, and R. Turner, White matter integrity, fiber count, and other fallacies: the do's and don'ts of diffusion MRI. Neuroimage, 2013. 73: pp. 239-254. NPL-1010.
Wang JY, Abdi H, Bakhadirov K, Diaz-Arrastia R, Dvous MD, Sr. A comprehensive reliability assessment of quantitative diffusion tensor tractography. Neuroimage, 2012. 60(2): pp. 1127-1138. NPL-1011.
Son SM, Park SH, Moon HH, et al. Diffusion tensor tractography can predict hemiparesis in infants with high risk factors. Neurosci Lett, 2009. 451(1): pp. 94-97. NPL-1013.
Kinoshita M, Hasimoto N, Goto T, et al. Fractional anisotropy and tumor cell density of the tumor core show positive correlation in diffusion tensor magnetic resonance imaging of malignant brain tumors. Neuroimage, 2008. 43(1): pp. 29-35. NPL-1014.
Hendrix P, Griessenauer CJ, Cohen-Adad J, et al. Spinal diffusion tensor imaging: A comprehensive review with emphasis on spinal cord anatomy and clinical applications. Clin Anat, 2014. NPL-1015.
Kajstura J, Cheng W, Reiss K, et al. Apoptotic and necrotic myocyte cell deaths are independent contributing variables of infarct size in rats. Lab Invest 1996;74(1):86-107. NPL-981.
Lindstedt S, Johansson M, Hlebowicz J, et al. Myocardial topical negative pressure increases blood flow in hypothermic, ischemic myocardium. Scand Cardiovasc J Mar. 4, 2008;1-9. NPL-984.
Trivedi R, Husain N, Rathore RK, et al. Correlation of diffusion tensor imaging with histology in the developing human frontal cerebrum. Dev Neurosci, 2009. 31(6): p. 487-496. NPL-1012.
Yellon DM, Hausenloy DJ. Myocardial reperfusion injury. N. Engl J Med Sep. 13, 2007;357(11):1121-35. NPL-974.
Frangogiannis NG, Smith CW, Entman ML. The inflammatory response in myocardial infarction. Cardiovasc Res Jan. 2002;53(1):31-47. NPL-975.
Jordan JE, Zhao ZQ, Vinten-Johansen J. The role of neutrophils in myocardial ischemia-reperfusion injury. Cardiovasc Res Sep. 1999;43(4):860-78. NPL-976.
Bolli R. Oxygen-derived free radicals and myocardial reperfusion injury. An overview. Cardiovasc Drugs Ther 1991;5:249-68. NPL-977.
Jordan JE, Montalto MC, Stahl GL. Inhibition of mannose-binding lectin reduces postischemic myocardial reperfusion injury. Circulation Sep. 18, 2001;104(12):1413-8. NPL-978.
Amsterdam EA, Stahl GL, Pan HL, et al. Limitation of reperfusion injury by a monoclonal antibody to C5a during myocardial infarction in pigs. Am J Physiol 1995;268:H448-57. NPL-979.
Gottlieb RA, Burleson KO, Kloner RA, et al. Reperfusion injury induces apoptosis in rabbit cardiomyocytes. J Clin Invest 1994;94:1621-8. NPL-980.
Jordan JE, Mays JJ, Shelton JE, et al. Mechanical tissue resuscitation protects against myocardial ischemia-reperfusion injury. J Card Surg Jan. 2014;29(1):116-23. NPL-982.
Argenta LC, Morykwas MJ, Mays JJ, et al. Reduction of myocardial ischemia-reperfusion injury by mechanical tissue resuscitation using sub-atmospheric pressure. J Card Surg Mar. 2010;25(2):247-52. NPL-983.

Eisenhardt SU, Schmidt Y, Thiele JR, et al. Negative pressure wound therapy reduces the ischaemia/reperfusion-associated inflammatory response in free muscle flaps. J Plast Reconstr Aesthet Surg Dec. 1, 2011. NPL-985.
Jordan JE, Zhao Z-Q, Sato H, et al. Adenosine A2 receptor activation attenuates reperfusion injury by inhibiting neutrophil accumulation, superoxide generation and coronary endothelial adherence. J Pharmacol Exp Ther 1997;280 (1):301-9. NPL-986.
Sato H, Jordan JE, Zhao ZQ, et al. Gradual reperfusion reduces infarct size and endothelial injury but augments neutrophil accumulation. Ann Thorac Surg Oct. 1997;64(4):1099-107. NPL-987.
Manka R, Kozerke S, Rutz AK, et al. A CMR study of the effects of tissue edema and necrosis on left ventricular dyssynchrony in acute myocardial infarction: implications for cardiac resynchronization therapy. J Cardiovasc Magn Reson 2012;14:47. NPL-988.
Ostergaard L, Kristiansen SB, Angleys H, et al. The role of capillary transit time heterogeneity in myocardial oxygenation and ischemic heart disease. Basic Res Cardiol May 2014;109(3):409. NPL-989.
Schmiedl A, Haasis G, Schnabel PA, et al. Morphometric evaluation of volume shifts between intra-and extra-cellular space before and during global ischemia. Anat Rec Mar. 1995;241(3):319-27. NPL-990.
Laine GA, Allen SJ. Left ventricular myocardial edema. Lymph flow, interstitial fibrosis, and cardiac function. Circ Res Jun. 1991;68(6):1713-21. NPL-991.
Dongaonkar RM, Stewart RH, Geissler HJ, et al. Myocardial microvascular permeability, interstitial oedema, and compromised cardiac function. Cardiovasc Res Jul. 15, 2010;87(2):331-9. NPL-992.
Lindstedt S, Malmsjo M, Ingemansson R. No hypoperfusion is produced in the epicardium during application of myocardial topical negative pressure in a porcine model. J Cardiothorac Surg 2007;2:53. NPL-993.
Lindstedt S, Malmsjo M, Sjogren J, et al. Impact of different topical negative pressure levels on myocardial microvascular blood flow. Cardiovasc Revasc Med Jan. 2008;9(1):29-35. NPL-994.
Borgquist O, Anesater E, Hedstrom E, et al. Measurements of wound edge microvascular blood flow during negative pressure wound therapy using thermodiffusion and transcutaneous and invasive laser Doppler velocimetry. Wound Repair Regen Nov. 2011;19(6):727-33. NPL-995
Argenta, L.C., et al., "A new method for modulating traumatic brain injury with mechanical tissue resuscitation," Neurosurgery, 70:1281-1295 (2012). NPL-966.
Powers, et al., "Vacuum-assisted closure for complex cranial wounds involving the loss of dura mater," J Neurosurg (2013) 118:302-308. NPL-970.
Wagner, et al., "Biodegradable polymers useful in wound repair requiring negative pressure wound therapy," FASEB J. (Apr. 2009) 23:469.7, XP-002735954. NPL-971.
Timmers, et al., "The effects of varying degrees of pressure delivered by negative-pressure wound therapy on skin perfusion," Ann Plast Surg (2005) 55:665-671. NPL-972.
Extended European Search Report received in European Patent Application No. 09701384.1, dated Feb. 13, 2015. NPL-973.
Extended European Search Report dated Sep. 2, 2015 in corresponding European Application No. 09798735.8.
Wagner, et al., "Biodegradable polymers useful in wound repair requiring negative pressure wound therapy," FASEB J. (Apr. 2009) 23:469.7, XP-002735954, including poster presentation. NPL-1017.

* cited by examiner

APPARATUS AND METHOD FOR CARDIAC TISSUE MODULATION BY TOPICAL APPLICATION OF VACUUM TO MINIMIZE CELL DEATH AND DAMAGE

RELATED APPLICATIONS

The present application claims the benefit of priority of U.S. Provisional Application 61/088,558, filed on Aug. 13, 2008 and U.S. Provisional Application No. 61/081,997, filed on Jul. 18, 2008, the entire contents of which are incorporated herein by reference.

FIELD OF THE INVENTION

The present invention relates generally to a method and apparatus for treating cardiac tissue, and more particularly, but not exclusively, to modulating ischemic and reperfused heart tissue with topical sub-atmospheric pressure to minimize cell death and damage.

BACKGROUND OF THE INVENTION

Myocardial ischemia occurs when a portion of the heart does not receive sufficient oxygen and energy substrates to meet its demand. This usually occurs because of a blockage in the artery due to either atherosclerotic plaque or thrombus formation. In a myocardial infarction there is an area of injury where the cells, because of lack of blood flow, will die immediately. There is a layer adjacent where there is impaired blood flow that is equivalent to the zone of stasis and there is a more peripheral unaffected zone. Unfortunately the infarcted heart will attempt to increase rate of contracture and overall work to compensate for areas of the heart that are not functioning adequately. Consequentially the areas that are in the "zone of stasis" are called upon to do more work which will increase the energy requirements placed upon them and will subsequently result in further progression of death. If left untreated, this ischemia will lead to an expanding zone of infarction that may eventually extend transmurally across the thickness of the ventricle.

Limiting the degree of infarction resulting from myocardial ischemia is paramount to improving both short- and long-term outcomes in patients. Therefore, in order to salvage this myocardial tissue, timely reperfusion (re-establishment of coronary blood flow) of the tissue must take place. The amount of salvageable tissue within an ischemic zone is dependent on the timeliness of reperfusion. While reperfusion halts the ischemic processes by delivering oxygen and nutrients (including energy substrates), this process also rapidly sets into motion a series of events and cascades that exacerbates injury, extending the area of necrosis beyond that encountered during ischemia alone. Much of this reperfusion injury appears to be inflammatory in nature, but inappropriately directed against host tissues instead of foreign substances. Being able to reduce this reperfusion injury allows for the salvage of the greatest amount of myocardium.

Reperfusion injury manifests itself in a number of ways, including myocardial dysfunction (myocardial stunning), arrhythmias, and a collection of events that result in lethal reperfusion injury. Currently, there are effective pharmacologic therapies to treat reperfusion arrhythmias, and myocardial stunning will generally resolve by itself given time, leaving the mediators of lethal reperfusion injury as the logical targets in an attempt to preserve ischemic-reperfused, but viable tissue.

There are a large number of potential mediators of lethal reperfusion injury including calcium overload, oxygen radicals, changes in osmotic gradients (and subsequent cell swelling), the mitochondrial permeability transition pore, and inflammation (itself a complex set of cascades and mediators including complement activation, leukocyte infiltration and pro-inflammatory cytokines and mediators). In addition, the cardioprotective effects of selective inhibition of any and all of these phenomenon, including antioxidants, sodium-hydrogen exchange inhibitors, anti-inflammatory agents (including adenosine, adhesion molecule antibodies and complement inhibitors) in animal models of myocardial ischemia-reperfusion are known. However, very few have demonstrated any degree of clinical success in people, likely due to the fact that these therapeutics act selectively at a single point within a cascade of events, or on a single facet of a very complex and multifaceted process. Thus, though the application of negative (or sub-atmospheric) pressure therapy to wounded cutaneous and subcutaneous tissue demonstrates an increased rate of healing compared to traditional methods (as set forth in U.S. Pat. Nos. 5,645,081, 5,636,643, 7,198,046, and 7,216,651, as well as US Published Application Nos. 2003/0225347, 2004/0039391, and 2004/0122434, the contents of which are incorporated herein by reference), there remains a need in the art for devices and methods for treating myocardial ischemia. In these type wounds of cutaneous and subcutaneous wounds the screen/dressing can often be easily and non-invasively changed at routine, pre-determined intervals without significant disruption to the healing tissues. However, when techniques are used to treat tissues or organs in which the overlying skin is intact, the overlying skin must be surgically disrupted by the deliberate creation of a wound through the overlying tissue to expose the tissue or organ that was originally injured. The overlying, originally healthy tissues which were disrupted to expose the injured tissue can be sutured closed over top of the injured tissue. This allows for negative pressure treatment of the wounded tissues with restoration of the suprawound tissues. Current commercially available embodiments of negative pressure dressings and cover are not biodegradable or bioresorbable. This lack of biodegradability/bioresorbability necessitates re-opening of the sutured incision, removal of the dressing and cover, placement of a new dressing and cover, and again suturing the incision closed. This sequence would have to be repeated until the original wounded tissue is healed, with one final re-opening of the incision to remove the dressing and cover. Every time the incision is opened to change or remove the dressing and cover, it increases the risk that the site will become infected.

SUMMARY OF THE INVENTION

The present invention relates to devices and methods for treating damaged heart tissue, such as myocardial infarction in the ischemic or early reperfusion phase, by treatment with sub-atmospheric (or negative) pressure. Treatment with the devices and methods of the present invention may salvage cells in the zone of stasis and thereby decrease the size of the infarct. Such treatment would be especially efficacious in endstage myocardial disease where bypass or stenting would not be possible. The treatment would also be useful as an adjunct to ECMO (extracorporeal membrane oxygenation) for resting the heart, following cardiac arrest, in situations with left main artery lesions, etc.

An exemplary negative pressure therapy device of the present invention may include a vacuum dressing, e.g., porous material, for placement over the tissue to be treated.

The vacuum dressing may be bio-incorporable in nature so that a second stage for removal would not be required. (As used herein the term "bio-incorporable" is defined to describe a material that may be left in the patient indefinitely and is capable of being remodeled, resorbed, dissolved, and/or otherwise assimilated or modified.) The device of the present invention may also include a bio-incorporable overlay cover for placement over the vacuum dressing to form a sealed enclosure in which sub-atmospheric pressure may be provided and maintained to the vacuum dressing and the tissue to be treated. The overlay cover may be adherent to the dressing and extend beyond the vacuum dressing to permit attachment of the overlay cover to surrounding non-damaged heart tissue. The overlay cover may be gelatinous in nature to contour to the heart and may be sufficiently pliable so as not to interfere with cardiac function. The overlay cover may be secured to the myocardium with fibrin glue, mini-staples, or sutures.

In use, the device of the present invention may be placed thoracoscopically over the area of muscle that has infarcted and over the adjacent zone of stasis. The device may be placed through a small incision made in the chest wall and perforated through the pericardium. The vacuum dressing may be collapsible in structure such that it can be rolled up or folded so as to be small enough for insertion through a thoracoscope tube. The epicardium may be perforated with a $CO_2$ or similar laser or other cutting instrument to expose the underlying ischemic myocardium. The vacuum dressing may then be placed directly over this ischemic area. The overlay cover may also be placed and secured to surrounding heart tissue endoscopically as well. A vacuum tube, e.g., a small catheter, may then be introduced so that the distal end of the vacuum tube is in gaseous communication with the enclosure under the overlay cover to supply sub-atmospheric pressure to the enclosure and the tissue to be treated. The other end of the vacuum tube may then be placed in gaseous communication with a vacuum source to produce sub-atmospheric pressure, and the vacuum source may be activated to supply the sub-atmospheric pressure to effect negative pressure therapy of the damaged heart tissue. In addition, the sub-atmospheric pressure may be supplied intermittently at a rate that is matched to the heart rate.

The present invention may also provide delayed treatment of myocardial infarction where there is already a stable zone of myocardial cell death. Again through an endoscope and a small incision in the chest wall, a bio-incorporable vacuum dressing may be placed on the area that is infarcted. Again, exposure of the myocardium involved and adjacent myocardium may be required and provided with a $CO_2$ or similar cutting device to perforate the epicardium. The vacuum dressing may be modified so that a lattice of myocardial or peripheral muscle cells may be incorporated within it. The vacuum dressing may also incorporate a small catheter with the ability to reinfuse additional myocardial cells, pleuripotent progenitor cells, or peripheral muscle cells at subsequent serial times. In areas where there is near complete cell death or there is little or no contraction of the muscle cells in the damaged cardiac tissue, new contractile cells could be seeded to replace and restore the contractile function of the damaged cardiac tissue. Initially, peripheral muscle or peripheral muscle cells grown from culture could be used. These cells have a finite life cycle and would be expected to fatigue over time. The myocardium could be biopsied at the time of the treatment of the initial treatment and myocardial cells removed and cultured to create a larger mass of viable of cells. The harvested myocardial cells could be maintained in culture and used for later periodic infusion to develop a myocardial patch that would cover the area of previous infarction.

Also, progenitor cells could be harvested and immediately infused to the area of damaged cardiac tissue, or they could be grown in culture and periodically infused to the area of damaged cardiac tissue with the expectation that they would develop into cardiac myocytes. Over time the introduced cells would be induced to undergo mitosis or self-replication thus increasing the functional mass of the heart. The ability to progressively add cells that would be progressively vascularized is a major step in regenerative medicine where presently only a sheet of cells can be expected to survive.

More specifically, in one of its aspects the present invention provides a method for treating damaged cardiac tissue using sub-atmospheric pressure. The method comprises placing a porous material in direct or indirect contact with the damaged cardiac tissue to provide gaseous communication between one or more pores of the porous material and the damaged cardiac tissue. The porous material may comprise at least one of an electrospun material, a cast material, an open-cell foam, or a printed material. Alternatively or additionally, the porous material may comprise a bio-incorporable material. The porous material may include, for example, collagen, chitosan, polycaprolactone, polyglycolic acid, polylactic acid, and combinations thereof. In addition, the porous material may be a polyvinyl alcohol foam which may be disposed in direct contact with the damaged cardiac tissue.

The porous material may be sealed in situ over the damaged cardiac tissue to provide a region about the damaged cardiac tissue for maintaining sub-atmospheric pressure at the damaged cardiac tissue. The porous material may be operably connected with a vacuum source for producing sub-atmospheric pressure at the damaged cardiac tissue, and the vacuum source activated to provide sub-atmospheric pressure at the damaged cardiac tissue. The sub-atmospheric pressure may be maintained at the damaged cardiac tissue for a time sufficient to reduce edema (thus restoring contractility and compliance), decrease interstitial pressure, remove inflammatory mediators, remove inflammatory amplifiers, modulate intracellular mediators, increase reperfusion and microvascular flow, decrease microvascular plugging, and/or decrease retention of inflammatory cells within the damaged cardiac tissue. Micro and macro deformation of the cardiac tissue being treated would increase vasculoneogenesis or the formation of new blood vessels in the ischemic tissue. This would increase the survivability of the cardiocytes and ultimately improve function of the ischemic portion of the heart. In addition, macro and micro deformation of small arterioles already existing in the heart would result in their physical reorientation into the areas of ischemic tissue, thus increasing perfusion and ultimately function.

For example, the sub-atmospheric pressure may be maintained at about 25-125 mm Hg below atmospheric pressure. The method may also include locating a cover, such as a bio-incorporable cover, over damaged cardiac tissue and sealing the cover to tissue proximate the damaged cardiac tissue, e.g., to non-damaged cardiac tissue, for maintaining sub-atmospheric pressure at the damaged cardiac tissue. The cover may be provided in the form of a self-adhesive sheet which may be located over the damaged cardiac tissue. In such a case, the step of sealing the cover may include adhesively sealing and adhering the self-adhesive sheet to tissue surrounding the damaged cardiac tissue to form a seal between the sheet and tissue surrounding the damaged cardiac tissue.

In another of its aspects the present invention provides an apparatus for treating damaged cardiac tissue. The apparatus includes a porous material for treating damaged cardiac tissue having a pore structure configured to permit gaseous communication between one or more pores of the porous material and the cardiac tissue to be treated. The porous material may include at least one of an electrospun material, a cast material, and a printed material. Alternatively or additionally, the porous material may comprise a bio-incorporable material. In such instances, it may also be beneficial for the porous material to be formulated in such a manner that the outer edges of the porous material would be resorbed or degraded more quickly than the inner portion. The rate of removal (resorption/degradation) of the porous material could be matched to the rate of formation of new tissue. One way to control the rate of degradation or resorption is by varying the number of crosslinks introduced into the porous material.

The apparatus may also include a vacuum source for producing sub-atmospheric pressure; the vacuum source may be disposed in gaseous communication with the porous material for distributing the sub-atmospheric pressure to the cardiac tissue. The porous material may have, at least at a selected surface of the porous material, pores sufficiently small to prevent the growth of tissue therein. In addition, the porous material may have, at least at a selected surface of the porous material, a pore size smaller than the size of fibroblasts and cardiac cells, and may have a pore size at a location other than the selected surface that is larger than that of fibroblasts and cardiac cells. The pore size of the porous material may be large enough to allow movement of proteins the size of albumin therethrough. Also, the porous material may include at least one surface that is sealed to prevent the transmission of sub-atmospheric pressure therethrough. The apparatus may also include a cover, such as a bio-incorporable cover, configured to cover the damaged cardiac tissue to maintain sub-atmospheric pressure under the cover at the damaged cardiac tissue.

The bio-incorporable porous material and/or cover may be constructed from synthetic materials such as polyglycolic acid, polylactic acid, or poly-o-citrate, or they can be constructed of naturally occurring molecules such as collagen, elastin, or proteoglycans. Combinations of synthetic molecules, combinations of naturally occurring molecules, or combinations of synthetic with naturally occurring molecules can be used to optimize the material properties of the porous material and cover.

An example of a material which may be used to fabricate the porous material is polycaprolactone (PCL). In one exemplary formulation, polycaprolactone is mixed with sodium chloride (1 part caprolactone to 10 parts sodium chloride) and placed in a sufficient volume of chloroform to dissolve the components. The solution is poured into an appropriately sized and shaped container and allowed to dry for twelve hours. The sodium chloride is then leached out in water.

A second exemplary cast formulation for the porous material is chitosan, 1.33% (weight/volume) in 2% acetic acid. The solution (20 ml) is poured into an appropriately sized container and frozen for 2 hours at −70° C., then transferred to a lyophylizer and vacuum applied for 24 hours. The freeze dried dressing is then crosslinked with 2.5 to 5% glutaraldehyde vapor for 12 to 24 hours.

Thus, the present invention provides devices and methods for minimizing the progression of pathologic processes, minimizing the disruption of physiological cardiac integrity, and minimizing the interference with cardiac blood flow and nutrition and increasing revascularization of ischemic areas of the heart by vascular neogenesis and reorientation of existing vessels. By decreasing cardiac edema and interstitial pressure the risk of cardiac cell death and compromise may be minimized. In addition, the present invention facilitates the removal of mediators, degradation products, and toxins that enhance the inflammatory and pathophysiological response in the damaged cardiac tissue.

BRIEF DESCRIPTION OF THE DRAWINGS

The foregoing summary and the following detailed description of the preferred embodiments of the present invention will be best understood when read in conjunction with the appended drawings, in which.

DETAILED DESCRIPTION OF THE INVENTION

Figure 1:
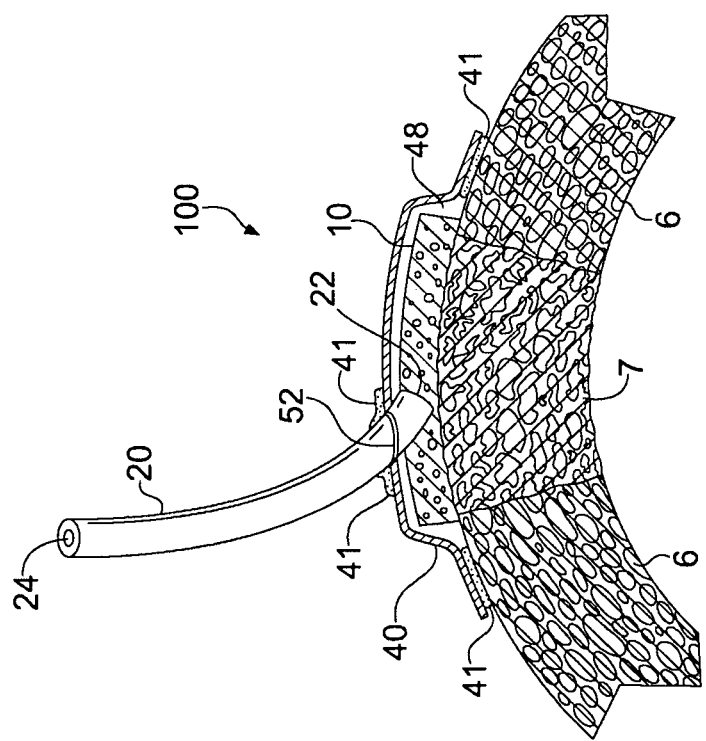
FIG. 1 schematically illustrates a partial cross-sectional view of an exemplary configuration of an apparatus of the present invention in situ prior to the application of sub-atmospheric pressure.

Referring now to the figures, wherein like elements are numbered alike throughout, the present invention relates to devices and methods that use sub-atmospheric (or negative) pressure for treating damaged cardiac tissue, where "damaged" tissue is defined to include tissue that is injured, compromised, or in any other way impaired, such as damage due to trauma, disease, infection, surgical complication, or other pathologic process, for example. More specifically, the devices and methods of the present invention can effect treatment of myocardial infarction.

An exemplary configuration of a sub-atmospheric cardiac treatment device 100 of the present invention may include a vacuum source 30 for supplying sub-atmospheric pressure via a tube 20 to a porous material 10, such as a bio-incorporable porous material, disposed in direct or indirect contact with the damaged cardiac tissue 7, FIGS. 1-4. As used here, "indirect contact" is defined to mean placement of an intermediate material for transmitting sub-atmospheric pressure in contact with both the damaged cardiac tissue 7 and the porous material 10. In this regard, the porous material 10 may be structured to deliver and distribute sub-atmospheric pressure to the damaged cardiac tissue 7. Alternatively, the porous material 10 may be comprised of a material that needs to be removed after sub-atmospheric therapy is given, which could require a second surgery. The cardiac treatment device 100 may be applied to a patient by locating a porous material 10 in contact with the damaged cardiac tissue 7 to provide gaseous communication between one or more pores of the porous material 10 and the damaged cardiac tissue 7. A tube 20 may be connected to the porous material 10 at a distal end 22 of the tube 20, and the porous material 10 may be sealed in situ by sutures 8 in the skin 1 and subcutaneous tissues 2 to provide a region about the damaged cardiac tissue 7 for maintaining sub-atmospheric pressure, FIG. 4. The proximal end 24 of the tube 20 may be attached to a vacuum source 30 to operably connect the porous material 10 to the vacuum source 30 for producing sub-atmospheric pressure at the damaged cardiac tissue 7 upon activation of the vacuum source 30. Optionally, an overlay cover 40, such as a bio-incorporable overlay cover 40, may be located over the damaged cardiac tissue 7 and sealed proximate the damaged cardiac tissue 7 to maintain sub-atmospheric pressure at the damaged cardiac tissue 7.

Figure 2:
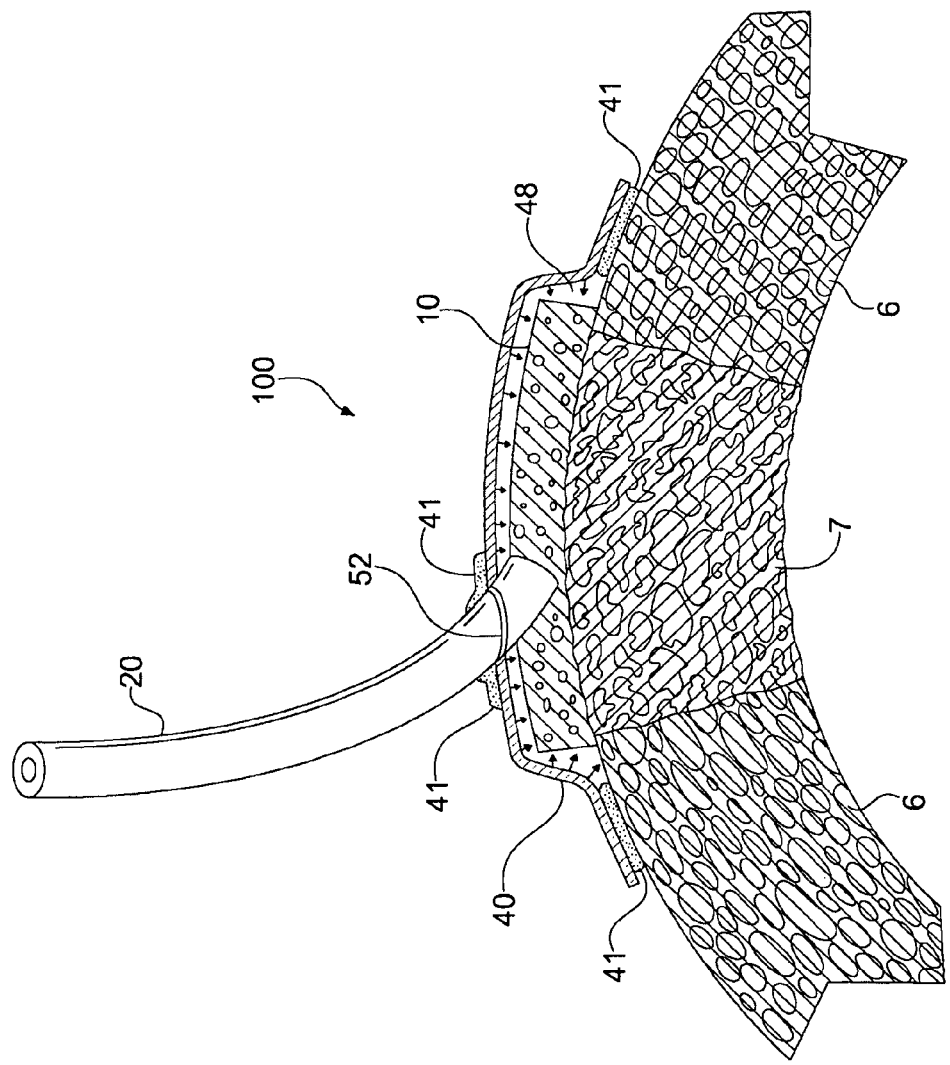
FIG. 2 schematically illustrates the partial cross-sectional view of FIG. 1 as a sub-atmospheric pressure is being applied.
Figure 3:
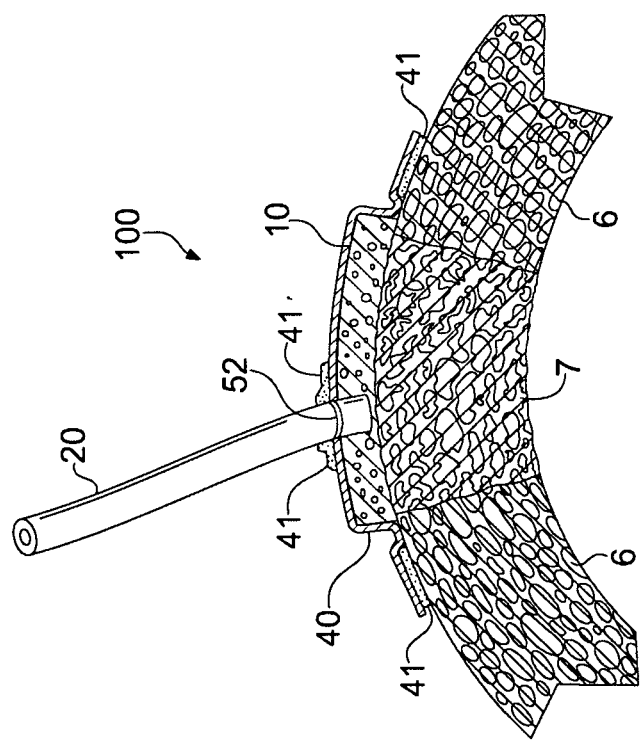
FIG. 3 schematically illustrates the partial cross-sectional view of FIG. 1 after sub-atmospheric pressure has been applied.

Turning to FIGS. 1-4 in greater detail, an exemplary configuration of a sub-atmospheric pressure cardiac treatment device 100 of the present invention is illustrated in partial cross-section with the porous material 10 in contact with the damaged cardiac tissue 7. An overlay cover 40 covers the porous material 10 and may extend onto healthy cardiac tissue 6 creating an enclosed space 48. An adhesive 41, such as fibrin glue or other material, may be placed between the overlay cover 10 and the healthy cardiac tissue 6. The adhesive 41 may also or alternatively be placed around the periphery of the overlay cover 10 to prevent leaks, and may also be placed around a passthrough 52 where the tube exits from the overlay cover 10 to prevent leaks. FIG. 1 depicts the device 100 prior to application of sub-atmospheric pressure. FIG. 2 depicts the device 100 as sub-atmospheric pressure is being applied, and the enclosed space 48 decreases in volume as fluid and gas are evacuated from the enclosed space 48 and the overlay cover 40 conforms to the porous material 10. FIG. 3 depicts the device 100 after sub-atmospheric pressure has been applied, with the overlay cover 40 conforming to the shape of the porous material 10.

Figure 4:
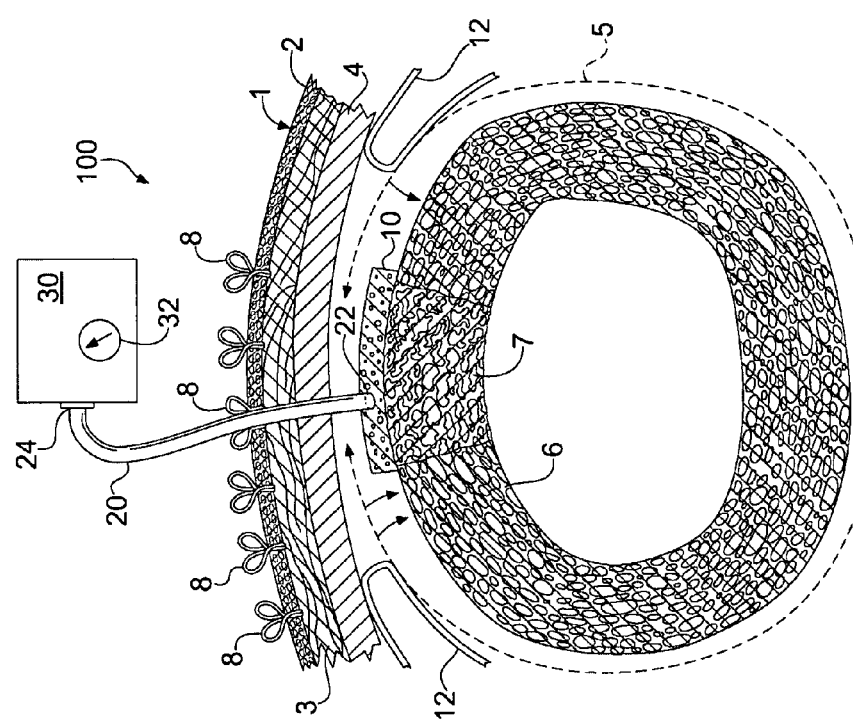
FIG. 4 schematically represents a cross-sectional view of an exemplary configuration of the present invention in situ in which the tissues overlying the heart have been closed around the tube to create a space capable of maintaining a vacuum so no overlay cover is required.

Turning to FIG. 4 specifically, an exemplary configuration of a sub-atmospheric cardiac treatment device 100 of the present invention is illustrated in situ in a patient with surrounding tissues shown in partial cross-section. The tissues illustrated include the skin 1 and subcutaneous tissue 2, muscle 3, bone 4, pericardium 5, healthy non-damaged cardiac tissue 6, the damaged cardiac tissue 7, and the pleural tissues 12. To provide access to the damaged cardiac tissue 7, a portion of the pericardium 5 may be missing due to surgical dissection or injury. A porous material 10, such as an open-cell collagen material, may be placed in the subcutaneous space in contact (direct or indirect) with the cardiac tissue 7 to be treated with sub-atmospheric pressure to decrease edema and interstitial pressure, oxygen radicals, inflammatory mediators, and other molecules which may adversely affect cellular resuscitation or viability within the damaged cardiac tissues to improve physiologic function, for example. The distal end 22 of the tube 20 may connect to the porous material 10 and the tube 20 may exit the body through an incision. The tube 20 may have one or more fenestrations 23 in that portion of the tube 20 in contact with the porous material 10, FIG. 6. The tissues between the cardiac tissue 7 up to and including the skin 1 are closed with, for example sutures 8, to create an airtight seal capable of maintaining a vacuum. When sub-atmospheric pressure is applied, the edges of the incised tissues 1-5 are drawn together and the pleural tissues 12 are drawn toward the porous material to help maintain the vacuum. The proximal end of the tube 24 may be connected to a vacuum source 30 and the level of sub-atmospheric pressure controlled by a controller 32. The vacuum source 30 may include a canister to collect any fluid removed.

The cover 40 may serve to further confine the region about the damaged cardiac tissue 7 at which sub-atmospheric pressure is maintained. That is, as illustrated in FIGS. 1-3, 7-9, the cover 40, 50 provides an enclosed space/region 48, 58 about the damaged cardiac tissue 7 under the cover 40, 50, which can serve to isolate the tissues exterior to the cover 40, 50 from exposure to the sub-atmospheric pressure applied to the damaged cardiac tissue 7. In contrast, as illustrated in FIG. 4, in the absence of an overlay cover, sub-atmospheric pressure delivered to the porous material 10 and damaged cardiac tissue 7 may draw the surrounding tissues, such as the pericardium 5 and pleural tissues 12, inward towards the tube 20 and porous material 10 along the directions of the arrows shown in FIG. 4. In this regard the stretched and/or moved tissues, such as pericardium 5 and pleural tissues 12 can help to confine the applied sub-atmospheric pressure to a region between the pericardium 5 and the damaged cardiac tissue 7. In addition the covers 40, 50 may further protect the damaged cardiac tissue 7 from exogenous infection and contamination beyond the protection already afforded by the porous material 10 and sutured skin 1 and subcutaneous tissue 2. Likewise, the covers 40, 50 may further protect the damaged cardiac tissue 7 from the spread of infections from the surrounding tissues (such as cardiac abscesses and mediastinitis).

Figure 7:
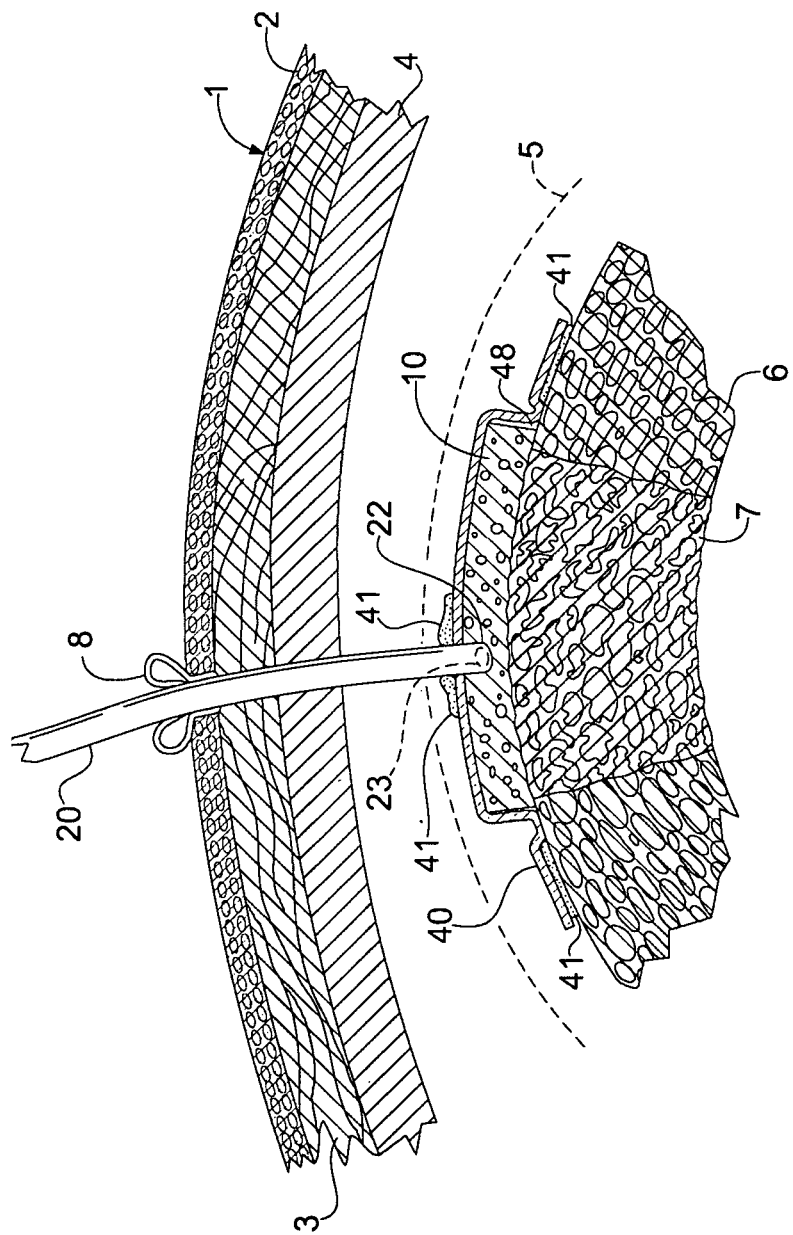
FIG. 7 schematically represents a cross-sectional view of an exemplary configuration of the present invention in which an overlay cover has been placed over the porous material and potential leaks sealed with fibrin glue.
Figure 8:
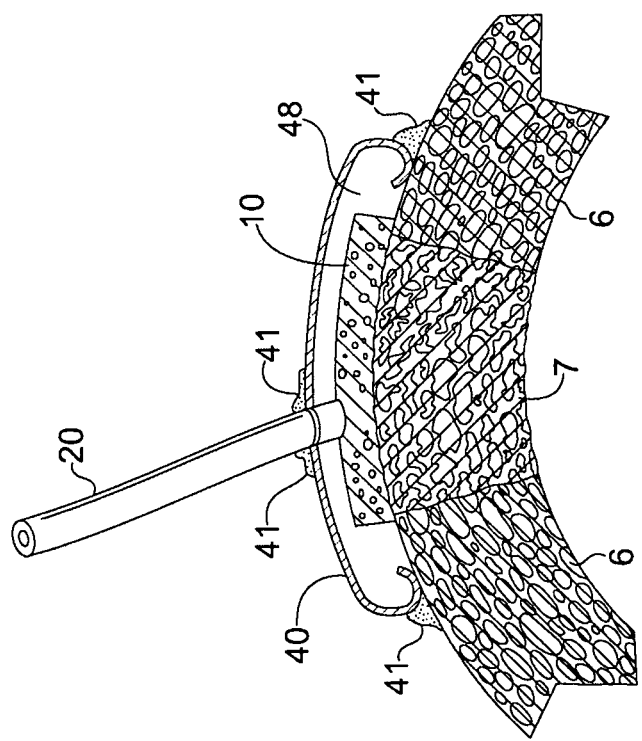
FIG. 8 schematically represents a partial cross-sectional view of an exemplary configuration of the present invention in which the edges of the overlay cover have been turned under.

To assist in maintaining the sub-atmospheric pressure at the damaged cardiac tissue 7, a flexible overlay cover 40 (FIG. 7), or a self adhesive flexible overlay cover 50 (FIG. 9) may be provided over the damaged cardiac tissue 7 to provide a region 48, 58 about the damaged cardiac tissue 7 where sub-atmospheric pressure may be maintained, FIGS. 7, 8. Specifically, with reference to FIGS. 7, 8, and 9, an overlay cover 40, 50 may be provided over the damaged cardiac tissue 7 and porous material 10 by adhering the cover 40, 50 to cardiac tissues proximate the damaged cardiac tissue 7 to define an enclosed region 48, 58 about the damaged cardiac tissue 7 and porous material 10. For instance, the cover 40 may be glued to cardiac tissue using an adhesive 41, such as a fibrin glue. The adhesive 41 may comprise an auto-polymerizing glue and/or may desirably include a filler to provide the adhesive 41 with sufficient bulk to permit the adhesive 41 to conform to the shapes of the potentially irregular surfaces which the adhesive 41 contacts. The adhesive 41 may be provided as a separate component or as a portion of the cover 40. For the flexible overlay cover 40, an outside edge or border of the flexible overlay cover 40 may either be rolled away from (or laid flat on) the non-damaged cardiac tissue 6 or rolled under (or toward) the damaged cardiac tissue 7, FIGS. 7, 8. The adhesive 41 may be placed between the edge of the overlay cover 40 and the healthy cardiac tissue 6 to promote an airtight seal. The adhesive 41 may also be placed around the tube 20 where it exits through the overlay cover 40. Alternatively, a self-adhesive flexible overlay cover 50 may be curled out away from the damaged cardiac tissue 7 so that the underside of the cover 50 (that side facing the porous material 10) may then contact with the surrounding non-damaged cardiac tissue 6, FIG. 9.

In addition to an open-cell collagen material, the porous material 10 may also include a polyglycolic and/or polylactic acid material, a synthetic polymer, a flexible sheet-like mesh, an open-cell polymer foam, a foam section, a porous sheet, a polyvinyl alcohol foam, a polyethylene and/or polyester material, or other suitable materials which may be fabricated by electrospinning, casting, or printing, for example. Such materials include a solution of chitosan (1.33% weight/volume in 2% acetic acid, 20 ml total volume) which may be poured into an appropriately sized mold. The solution is then frozen for 2 hours at −70° C., and then transferred to the lyophylizer and vacuum applied for 24 hours. The dressing may be cross-linked by 2.5%-5% glutaraldehyde vapor for 12-24 hours to provide a cast porous material.

Additionally, the porous material 10 may be made by casting polycaprolactone (PCL). Polycaprolactone may be mixed with sodium chloride (1 part caprolactone to 10 parts sodium chloride) and placed in a sufficient volume of chloroform to dissolve the components. A desired amount, e.g., 8 ml, of the solution may be poured into an appropriately sized and shaped container and allowed to dry for twelve hours. The sodium chloride may then be leached out in water for 24 hours.

The overlay cover 40 may also be bio-incorporable and may consist of an electrospun mixture of Type I collagen and poly 1,8-octanediol citrate (POC) (80%:20% weight/weight). The solution concentration may be 15% dissolved in hexafluoro-2 proponal (HFP) with a total volume of 9.5 ml. The solution may then be ejected from a syringe through an 18 gauge needle at a flow rate of 1-3 ml/hour. The voltage may be 25 KV with a working distance of 20-25 cm. The film may then be heat polymerized at 80° C. for 48 hours (of 90° C. for 96 hours) and cross-linked in 2.5%-10% glutaraldehyde vapor for 24 hours.

It is also possible to use electrospun materials for the porous material 10 and cast materials for the overlay cover 40. One example of a formulation and method for making an electrospun porous material 10 is a combination of collagen Type I:chondroitin-6-sulfate (CS):poly 1,8-octanediol citrate (POC) in a ratio of 76%:4%:20%: by weight. Two solvents were utilized for the collagen/CS/POC. The CS was dissolved in water and the collagen and POC were dissolved in 2,2,2-trifluoroethanol (TFE). A 20% water/80% TFE solution (volume/volume) solution was then used. For electrospinning, the solution containing the collagen:CS:POC mixture was placed in a 3 ml syringe fitted to an 18 Ga needle. A syringe pump (New Era Pump Systems, Wantaugh, N.Y.) was used to feed the solution into the needle tip at a rate of 2.0 ml/hr. A voltage of 10-20 kV was provided by a high voltage power supply (HV Power Supply, Gamma High Voltage Research, Ormond Beach. FL) and was applied between the needle (anode) and the grounded collector (cathode) with a distance of 15-25 cm. The dressings were then cross-linked with glutaraldehyde (Grade II, 25% solution) and heat polymerized (80° C.) for 48 hours. It is also possible to electrospin collagen Type I dressings starting with an initial concentration of 80 mg/ml of collagen in 1,1,1,3,3,3-hexafluoro-2-propanol (HFP), then use the same electrospinning conditions as the collagen:CS:POC combination.

Examples of cast overlay cover formulas include the use of 1,8 poly (octanediol) citrate (POC) or other combinations of diol citrates, which could be 1,6 hexanediol or 1,10 decanediol, for example. To make the cast overlay cover 40, equimolar amounts of anhydrous citric acid and the diol of choice may be combined in a round bottom flask. (As an example: 38.4 g citric acid and 29.2 g octanediol). The solution may be heated in an oil bath for 10 min at 165° C. until melted, then continued to be heated at 140° C. for 45 min. The polymer may be used in this form although unreacted monomers are also present. To remove the unreacted monomer, equivolume amounts of polymer and 100% acetone may be added to a flask and shaken until the polymer is completely dissolved, then poured into an appropriately shaped mold. The acetone may be evaporated overnight in a chemical hood at room temperature. The films may be polymerized at 80° C. for 36 hr and then 18 hr at 110° C.

Alternatively, to cast overlay covers 40 of chitosan, a solution of 2% acetic acid in water may be added to 1% chitosan weight/volume. (For example 400 µl acetic acid may be added to 20 ml water, then 200 mg chitosan added.) Films may be prepared by pouring the mixture directly into the mold and allowing the solution to dry overnight. Cast overlay covers 40 of poly L (lactic acid) or poly D,L (co-glycolic lactic acid) dissolved in chloroform can also be made by pouring the solution into molds and evaporating the solvent (chloroform) off.

An additional method for creating porous materials 10 and overlay covers 40 is to use thermal inkjet printing technologies. Bio-incorporable materials such as collagen, elastin, hyaluronic acid, alginates, and polylactic/polyglycolic acid co-polymers may be printed. As examples, Type I collagen (Elastin Products Co., Owensville, Mo.) dissolved in 0.05% acetic acid, then diluted to 1 mg/ml in water can be printed, as can sodium alginate (Dharma Trading Co., San Raphael, Calif.) 1 mg/ml in water. A mixture of Type I collagen (2.86 mg/ml in 0.05% acetic acid) and polylactic/polyglycolic acid (PURAC America, Blair, Nebr.) (14.29 mg/ml in tetraglycol (Sigma Aldrich, St. Louis Mo.)) can also be printed. Hardware from a Hewlett Packard 660c printer can be attached to a platform for which the height can be adjusted for printing in layers. With minimal changes to the hardware, no software changes need to be made.

Figure 5:
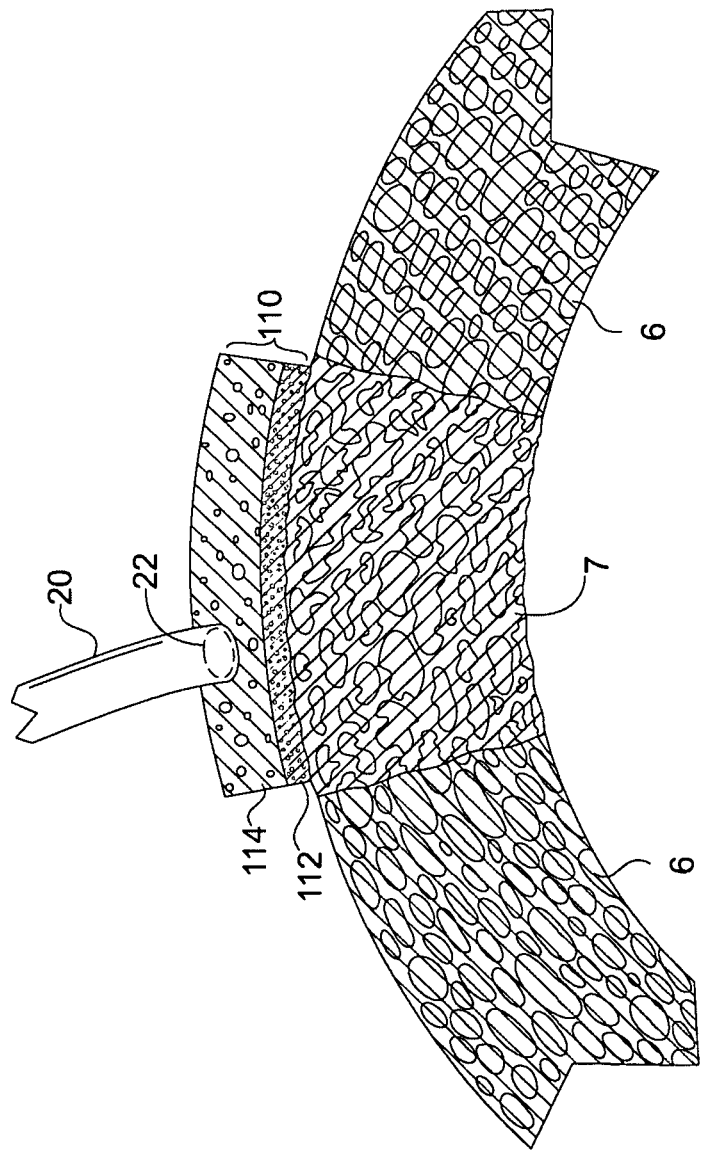
FIG. 5 schematically represents a partial cross-sectional view of the apparatus of the present invention in situ in which the porous material is layered with a smaller pore layer adjacent to the damaged tissue and a layer with larger pores above the smaller pore layer.

Turning to FIG. 5, the porous material 10 may comprise layers, with the layer 112 closest to the damaged cardiac tissue containing pores sufficiently small at the interface between the porous material 110 and the damaged cardiac tissue 7 to prevent the growth of tissue therein, e.g., a pore size smaller than the size of fibroblasts and cardiac cells. Otherwise the porous material 110 may stick to the damaged cardiac tissue 7 and cause bleeding or trauma, and potentially even disruption of the ventricular wall when the porous material 110 is removed. Additionally, growth of tissues into the porous material 110 may result in eventual erosion through the ventricular wall or pleural tissues with continual movement and rubbing of the porous material 110 against these tissues if the porous material 110 is left in the patient. Further, growth of tissues into the porous material 110 may result in non-contractible scar formation within the porous material or potential calcification of tissues within the porous material 110 if the porous material 110 is left within the patient. In addition, the pore size at the interface between the porous material 10, 110 and the damaged cardiac tissue 7 may be sufficiently small so as to avoid the excessive production of granulation or scar tissue at the damaged cardiac tissue 7 which may interfere with the physiologic function of the heart. At the same time, the pore size of the porous material 10, 110 may be large enough to allow movement of proteins the size of albumin therethrough to permit undesirable compounds to be removed, such as mediators, degradation products, and toxins.

The porous material 10, 110 may, however, have a larger pore size (e.g., larger than that of fibroblasts and cardiac cells) interior to the porous material 10, 110 or at any other location of the porous material 10 that is not in contact with cardiac tissue 7. For example, the porous material 110 may comprise a multi-layer structure with a non-ingrowth layer 112 having a sufficiently small pore size to prevent the growth of tissue therein for placement at the cardiac tissue 7, and may have an additional layer 114 of a different material that has a relatively larger pore size in contact with the non-ingrowth layer 112.

Figure 6:
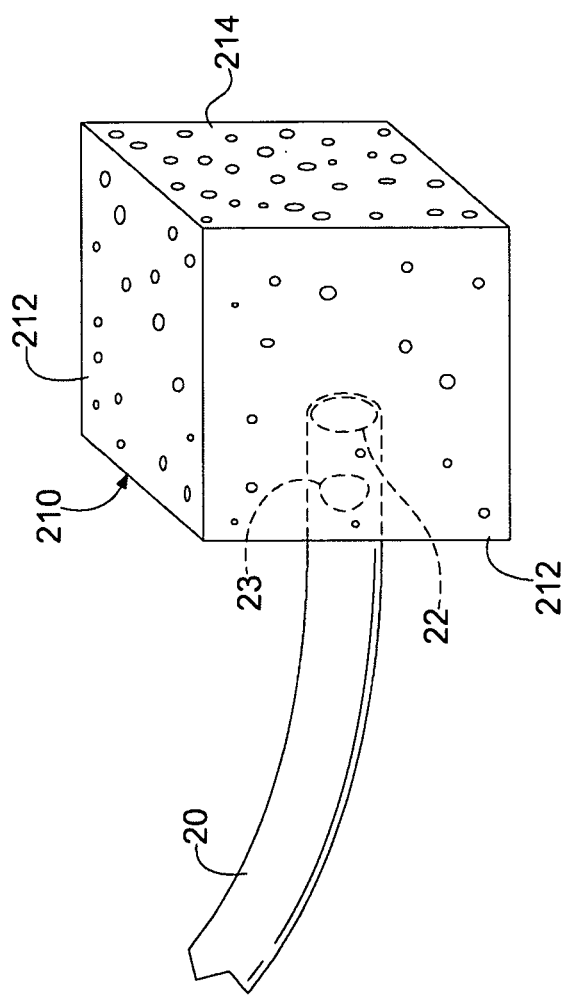
FIG. 6 schematically represents a view of an exemplary configuration of a porous material of the present invention in which only one side of the porous material is open and not sealed.

Alternatively, as depicted in FIG. 6, the porous material 210 may be homogeneous in composition and/or morphology. At a location away from the interface with the damaged cardiac tissue, the porous material 210 may have a pore size sufficiently large to promote the formation of granulation tissue at other tissues in the spaces surrounding the damaged cardiac tissue, such as promotion of granulation tissue in areas where cardiac disruption has occurred. In addition, the porous material 210 may have a configuration in which one or more sides or surfaces 212 of the porous material 210 are sealed to prevent the transmission of sub-atmospheric pressure through such a sealed surface 212, while at the same time having at least one surface 214 through which sub-atmospheric pressure may be transmitted. Such a configuration of the porous material 210 can present preferential treatment of tissue on one side of the porous material 210 while not treating tissue on the other side. For instance, the damaged cardiac tissue could be treated with the non-sealed interface on one side 214 of the porous material 210.

In addition, the porous material 10 may comprise a non-metallic material so that an MRI can be performed while the porous material 10 is in situ. The porous material 10 may also comprise a material that is sufficiently compliant so that it does not interfere with cardiac function. At the same time, the porous material 10 may comprise a material that is sufficiently firm so that the porous material 10 does not collapse so much as to create a pull on, or distortion of, the cardiac tissue 6, 7 that might interfere with cardiac function.

Turning to FIG. 7, to deliver sub-atmospheric pressure to the porous material 10 for distribution to the damaged cardiac tissue 7, a tube 20 may be connected directly or indirectly in gaseous communication with the porous material 10 at the distal end 22 of the tube 20. For example, the distal end 22 of the tube 20 may be embedded in the porous material 10 or may be placed over the porous material 10. The distal end 22 of the tube 20 may also include one or more fenestrations 23 to assist in delivering the sub-atmospheric pressure to the porous material 10 and the damaged cardiac tissue 7. The tube 20 may extend through an opening in the skin 1 and subcutaneous tissue 2 which may be secured about the tube 20 with a suture 8 to assist in providing a seal about the tube 20. The proximal end 24 of the tube 20 may be operably connected to a vacuum source 30 (e.g., The V.A.C., Model 30015B, Kinetic Concepts, Inc., San Antonio, Tex.) to provide sub-atmospheric pressure that is transmitted via the tube 20 to the porous material 10 and the damaged cardiac tissue 7.

The vacuum source 30 may include a controller 32 to regulate the production of sub-atmospheric pressure. For instance, the vacuum source 30 may be configured to produce sub-atmospheric pressure continuously or intermittently; e.g., the vacuum source 30 may cycle on and off to provide alternating periods of production and non-production of sub-atmospheric pressure. The duty cycle between production and non-production may be between 1 to 10 (on/off) and 10 to 1 (on/off). In addition, intermittent sub-atmospheric pressure may be applied by a periodic or cyclical waveform, such as a sine wave, or may be cycled after initial treatment to mimic a more physiologic state, such as the heart rate. The sub-atmospheric pressure may also be cycled on-off as-needed as determined by monitoring of the pressure in the damaged cardiac tissue 7. In general, the vacuum source 30 may be configured to deliver sub-atmospheric pressure between atmospheric pressure and 200 mm Hg below atmospheric pressure to minimize the chance that the sub-atmospheric pressure may result in reduction in localized blood flow due to either constriction of capillaries and small vessels or due to congestion (hyperemia) within the damaged cardiac tissue 7 or otherwise be deleterious to the damaged cardiac tissue 7. The application of such a sub-atmospheric pressure can operate to remove edema from the damaged cardiac tissue 7, thus preserving cardiac function to increase the probability of recovery and survival in a more physiologically preserved state.

Figure 10:
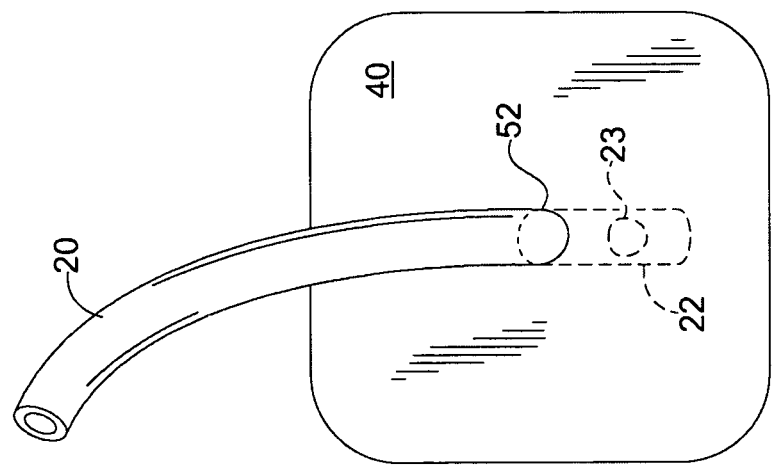
FIG. 10 schematically represents an exemplary configuration of the cover of the present invention in which the tube passes through the overlay cover.
Figure 9:
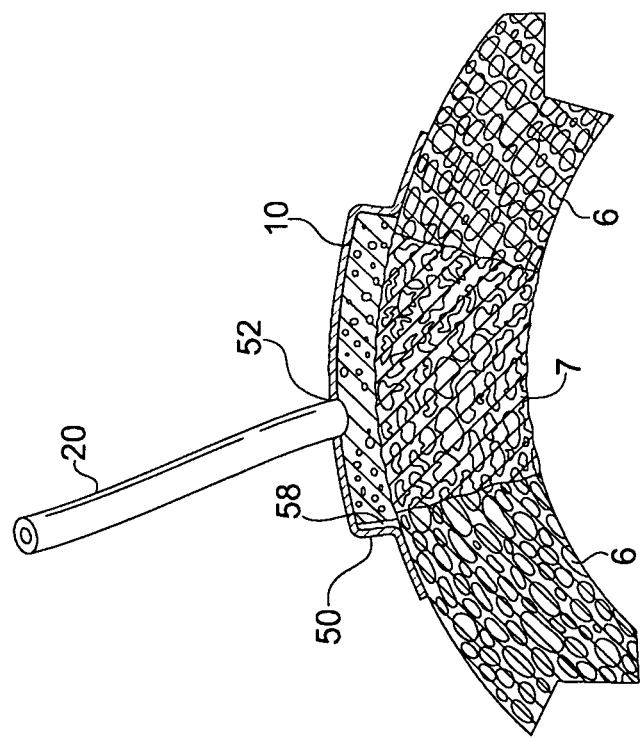
FIG. 9 schematically represents a cross-sectional view of an exemplary configuration of the present invention in which the overlay cover is self adhesive.

Turning to FIG. 10, sub-atmospheric pressure may be delivered under the cover 50 by cooperation between the cover 50 and the tube 20. Specifically, the flexible overlay cover 40 (or self-adhesive flexible overlay cover 50) may include a passthrough 52 through which the distal end 22 of the tube 20 passes to provide gaseous communication between the tube 20 and the space under the flexible overlay cover 40 over the damaged cardiac tissue.

In another of its aspects, the present invention also provides a method for treating damaged cardiac tissue using sub-atmospheric pressure with, by way of example, the devices illustrated in FIGS. 1-4. In particular, the method may comprise locating a porous material 10 proximate the damaged cardiac tissue 7 to provide gaseous communication between one or more pores of the porous material 10 and the damaged cardiac tissue 7. The porous material 10 may be sealed in situ proximate the damaged cardiac tissue 7 to provide a region about the damaged cardiac tissue 7 for maintaining sub-atmospheric pressure at the damaged cardiac tissue 7. In this regard, the muscles 3, and bone 4 may be loosely re-approximated over top of the porous material 10 with the tube 20 exiting through the skin 1 and subcutaneous tissue 2 and the skin 1 and subcutaneous tissue 2 sutured closed. A further airtight dressing may optionally be placed over the suture site to promote an airtight seal. The porous material 10 may be operably connected with a vacuum source 30 for producing sub-atmospheric pressure at the damaged cardiac tissue 7, and the vacuum source 30 activated to provide sub-atmospheric pressure at the damaged cardiac tissue 7. For example, the sub-atmospheric pressure may be maintained at about 25 to 125 mm Hg below atmospheric pressure. The sub-atmospheric pressure may be maintained at the damaged cardiac tissue 7 for a time sufficient to decrease edema at the damaged cardiac tissue 7. In addition, the sub-atmospheric pressure may be maintained at the damaged cardiac tissue 7 for a time sufficient to prepare the cardiac tissue 7 to achieve a stage of healing and diminution of edema and inflammatory mediators or amplifiers. The method may be used for at least 2 hours, or can be used for many days. At the end of the vacuum treatment, the sutures 8 may be removed and the skin 1, subcutaneous tissue 2, muscles 3 and bone 4 re-opened. The porous material 10 may then be removed and the skin 1, subcutaneous tissue 2, and/or muscles 3 re-sutured closed.

Figure 11:
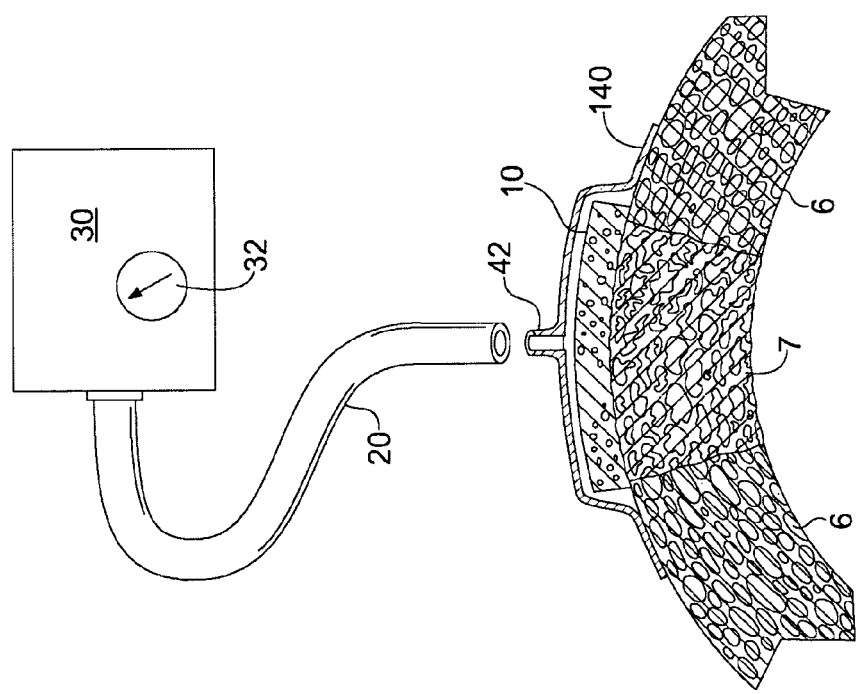
FIG. 11 schematically represents a partial cross-sectional view of the vacuum tube attaching to the overlay cover.

The method may also include locating an overlay cover 40, 50, such as a bio-incorporable cover 40, 50, over the damaged cardiac tissue 7 and sealing the overlay cover 40, 50 to tissue proximate the damaged cardiac tissue 7 for maintaining subatmospheric pressure at the damaged cardiac tissue 7. The step of sealing the overlay cover 40, 50 to tissue surrounding the damaged cardiac tissue 7 may comprise adhesively sealing and adhering the overlay cover 40, 50 to tissue surrounding the damaged cardiac tissue 7. The overlay cover 50 may be provided in the form of a self-adhesive sheet 50 which may be located over the damaged cardiac tissue 7. In such a case, the step of sealing the overlay cover 50 may include adhesively sealing and adhering the self-adhesive overlay cover 50 to non-damaged cardiac tissue 6 surrounding the damaged cardiac tissue 7 to form a seal between the overlay cover 50 and the non-damaged cardiac tissue 6 surrounding the damaged cardiac tissue 7. In addition, the step of operably connecting a vacuum source 30 in gaseous communication with the porous material 10 may comprise connecting the vacuum source 30 to the tube 20 which attaches to the vacuum port 42 of the cover 140 FIG. 11.

Figure 13:
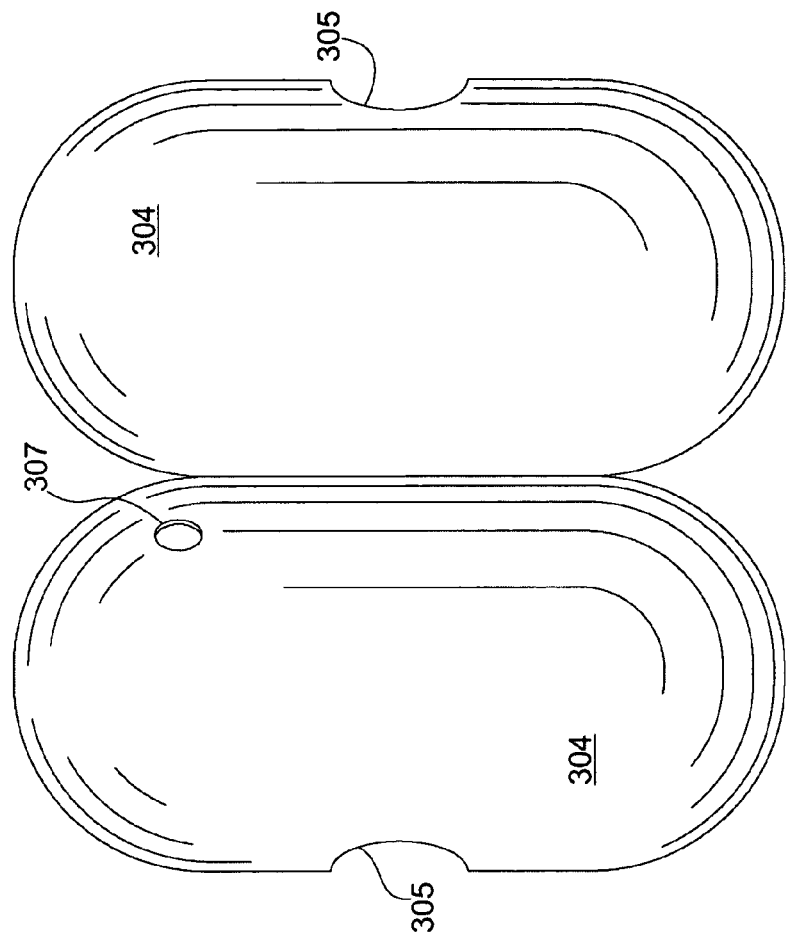
FIG. 13 schematically represents an open clamshell or bi-valve chamber for application of sub-atmospheric pressure.
Figure 12:
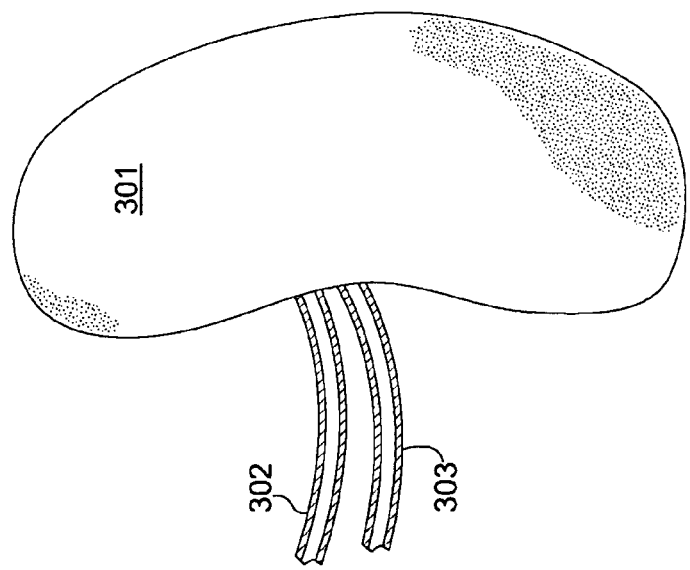
FIG. 12 schematically represents a kidney, with artery and vein.
Figure 14:
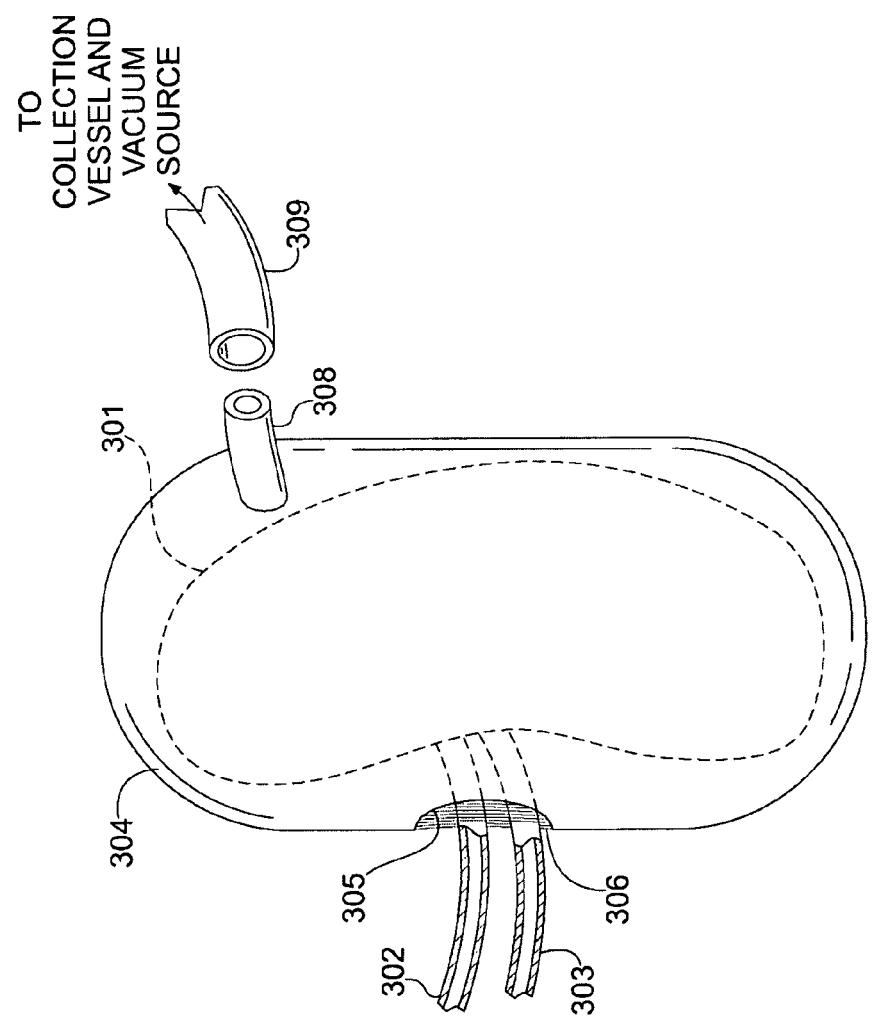
FIG. 14 schematically represents a kidney disposed within the chamber of FIG. 13.

In still another aspect of the present invention, in addition to injured tissues and organs, the devices and methods may also be used to increase the size and function of diseased or damaged organs. For example, the size of a partially functioning kidney may be increased to a size sufficient to return the total filtering capacity to normal levels, FIGS. 12-14, such as the increase in size of the remaining kidney 301 as is observed in patients who only have one functioning kidney 301. In such a situation, a rigid or semi-rigid bi-valved enclosure 304 with an opening 305 for the vascular pedicle may be placed around the kidney 301. When the bi-valved enclosure 304 is closed, the area where the two halves meet creates an air tight seal. The vascular pedicle enters (artery 302) and exits (vein 303) through the opening 305. Fibrin glue 306 or other biocompatible sealant may be placed around the artery 302 and vein 303 at the site of the opening 305 to create an airtight seal. The enclosure 304 may include a second opening 305 or a nipple 308. A tube 309 may be inserted through the second opening 305 or attached to the nipple 308. The tube 309 may exit through the skin, be connected to a collection vessel, and then connected to a vacuum source. A controlled vacuum of up to 125 mm Hg sub-atmospheric pressure may be applied either intermittently, with an 'on' time of up to five minutes and an 'off' time of up to 10 minutes. Alternatively, the vacuum may be applied in a periodic or cyclical manner, such as a sine wave, in which the absolute value of the lower (closest to atmospheric pressure) values of the applied vacuum are less than the diastolic blood pressure to allow blood to flow out of the treated organ. The time in which the applied vacuum is greater (in absolute value) than the diastolic blood pressure may be up to five minutes, with the time in which the applied vacuum is lower (in absolute value) than the diastolic blood pressure may be up to ten minutes. The technique is continued until the treated organ has either reached the desired level of function or fills the container. As an additional example, this device and technique may similarly be used on lobes of the liver or for increasing the size of the pancreas.

EXAMPLES

Example 1

The porcine heart has anatomy similar to that of humans with the main vasculature consisting of the right and left coronary arteries. The left main coronary artery splits into the circumflex coronary artery and the left anterior descending (LAD) coronary artery. The LAD runs down along the anterior septum and perfuses the anterior portion of the left ventricle with diagonal branches. For these studies, a porcine model of ischemia-reperfusion was used that included the temporary ligation of 2-3 diagonal branches of the LAD in order to create an ischemic area on the anterior portion of the heart. These coronary arteries were occluded for 75 minutes and then reperfused for 3 hours to allow for ischemia/reperfusion injury to develop. The negative pressure therapy was applied only during the reperfusion phase of the experiments to simulate a clinically relevant treatment window.

To begin the study, the animals were sedated and transported to the operating room. The first 13 animals had the heart exposed through a thoracotomy, all subsequent animals had the heart exposed through a sternotomy. The 2-3 diagonal branches of the LAD were ligated (occluded with suture) in order to create an ischemic area on the anterior portion of the heart. These coronary arteries were occluded for 75 minutes and then reperfused for 3 hours to allow for reperfusion injury to develop. The negative pressure therapy was applied only during the reperfusion phase of the experiments to simulate a clinically relevant treatment window. Five control animals were created from the first 13 animals of the study.

Following successful completion of control animals to validate the study design, the subsequent 5 successful (sternotomy) animals had negative pressure therapy treatment to the ischemic area of the heart for 3 hours during the reperfusion time. For the first 5 successfully treated animals, the vacuum dressing included use of a polyvinyl alcohol porous material (Versafoam, KCI, San Antonio Tex.), cut to approximately 1 mm thickness and trimmed to match the ischemic area. The evacuation tube was either embedded into a slit cut into the porous material (2 animals), or was sutured to the outer surface of the porous material (3 animals). This vacuum dressing was then covered with a biologically derived overlay cover. These biological coverings included: 1 animal treated with E•Z DERM™ (Non-perforated porcine biosynthetic wound dressing, Brennen Medical, St. Paul, Minn.); 1 animal treated with bovine pericardium; and 3 animals treated with AlloDerm® (human dermis) (LifeCell). The overlay covers were attached to the heart by three means: suturing, fibrin glue, and self sealing due to a relatively large 'apron' of the cover material around the periphery of the vacuum dressing. The evacuation tube exited from under the edge of the 'apron' of the overlay covers. The fibrin glue was used in conjunction with suturing and also with spot sealing for the self sealing application (at wrinkles, where the evacuation tube exited, etc.). Negative pressure of 125 mm Hg (i.e., 125 mm Hg below atmospheric) was then applied for 3 hours during the reperfusion period using The V.A.C., Model 30015B, Kinetic Concepts, Inc., San Antonio, Tex.

To determine the effects of ischemia/reperfusion, the sutures were re-tied at the end of the 3 hour reperfusion period. Blue dye (patent blue, Sigma-Aldrich Inc, St. Louis, Mo.) was injected into the right atrium. This stained the areas of the heart that were normally perfused. The left ventricle was dissected free from the rest of the heart and weighed (LV in Table). The area of ischemia (non-blue area) was further dissected from the left ventricle. The blue area of the left ventricle was then weighed (Blue in Table). The ischemic area (non-blue tissue) was then stained with a dye (2,3,5-triphenyltetrazolium chloride, Sigma-Aldrich Inc., St Louis Mo.) which stains live cells red. The red areas were dissected from the area of ischemia and were weighed (Red in Table), leaving areas of pale dead tissue (area of necrosis—AN in Table), and these pale tissue samples were weighed (Pale in Table). The combined Red and Pale areas constitute the area at risk (AAR in Table). The AN/AAR is the size of the infarct (percent of tissue that died during the ischemia/reperfusion time periods).

The results for the 5 control animals were:

TABLE 1

Control Animals

| | Blue | Red | Pale (AN) | LV | AAR | AAR/LV (%) | AN/AAR (%) |
|---|---|---|---|---|---|---|---|
| Animal 1 | 75.6 | 5.85 | 2.18 | 83.63 | 8.03 | 9.60 | 27.15 |
| Animal 2 | 90.5 | 10.63 | 2.44 | 103.57 | 13.07 | 12.62 | 18.67 |
| Animal 3 | 85.39 | 12.16 | 4.26 | 101.81 | 16.42 | 16.13 | 25.94 |
| Animal 4 | 92.45 | 8.17 | 3.47 | 104.09 | 11.64 | 11.18 | 29.81 |
| Animal 5 | 81.24 | 9.86 | 4.34 | 95.44 | 14.20 | 14.88 | 30.56 |
| | | | Mean | 97.71 | 12.67 | 12.88 | 26.43 |
| | | | Std Dev | 8.59 | 3.13 | 2.66 | 4.73 |
| | | | N | 5.00 | 5.00 | 5.00 | 5.00 |
| | | | Std Err | 3.84 | 1.40 | 1.19 | 2.12 |

The results for the 5 treated animals were:

TABLE 2

−125 mm Hg Treated Animals

| Group | Blue | Red | Pale | LV | AAR | AAR/LV (%) | AN/AAR (%) |
|---|---|---|---|---|---|---|---|
| Animal 1 | 73.06 | 10.31 | 1.23 | 84.60 | 11.54 | 13.64 | 10.66 |
| Animal 2 | 73.2 | 5.9 | 0.61 | 79.71 | 6.51 | 8.17 | 9.37 |
| Animal 3 | 75 | 11.15 | 2.05 | 88.20 | 13.20 | 14.97 | 15.53 |
| Animal 4 | 54.1 | 4.85 | 0.52 | 59.47 | 5.37 | 9.03 | 9.68 |
| Animal 5 | 62.12 | 8.63 | 1.42 | 72.17 | 10.05 | 13.93 | 14.13 |
| | | | Mean | 76.83 | 9.33 | 11.95 | 11.87 |
| | | | Std Dev | 11.41 | 3.32 | 3.11 | 2.78 |
| | | | N | 5.00 | 5.00 | 5.00 | 5.00 |
| | | | Std Err | 5.10 | 1.48 | 1.39 | 1.24 |

Thus, the mean sizes of the infarct (AN/AAR; percent of tissue that died during the ischemia/reperfusion time period) for the control and treated animals were:

Control 26.43+/−2.12% (mean+/−SEM) (n=5)

Treated 11.87+/−1.24% (mean+/−SEM) (n=5),
with T-test results of P<0.001 for infarct size and P<0.625 for area at risk.

Example 2

Another experiment was conducted using 50 mm Hg vacuum for treatment for comparison to original control animals from Example 1 above. The surgical technique in this experiment was similar to that used for those of Example 1. These animals were sedated and prepped for surgery. The heart was exposed through a midline sternotomy. Branches of the left anterior descending artery were ligated for 75 minutes. A polyvinyl alcohol vacuum dressing was placed over the ischemic area and an AlloDerm® cover was placed over the vacuum dressing and sealed into place with a combination of sutures and fibrin glue. Negative pressure of 50 mm Hg was applied for 3 hours. At the end of this time the heart was stained for area of risk, removed and then counter stained for area of necrosis. The infarct size results for these five, 50 mm Hg negative pressure therapy animals were significantly smaller (P<0.001) than for the control animals. The infarct size for the 50 mm Hg treated animals was smaller than the infarct size for the 125 mm Hg treated animals, but was not significantly smaller.

| Group | AAR/LV | (%) AN/AAR |
|---|---|---|
| Control | 12.9 ± 1.2 | 26.4 ± 2.1 |
| 50 mm Hg negative pressure | 11.8 ± 2.0 | 9.3 ± 1.8 ** |
| 125 mm Hg negative pressure | 11.9 ± 1.4 | 11.9 ± 1.2 ** |

** p < 0.001 compared to Control animals

The mean arterial pressure and heart rate of animals in all three groups (control, −125 mm Hg, −50 mm Hg) were comparable during the course of these experiments.

Fifteen micron neutron-activated microspheres (BioPAL, Inc, Worcester, Mass.) were injected into the left atrium at baseline, end of ischemia, 30 minutes into reperfusion and at 180 minutes of reperfusion (end of the experiment). A reference sample of arterial blood was simultaneously drawn from the femoral artery at a rate of 7 mL per minute for ninety seconds. Following infarct sizing procedures, tissue samples from the non-ischemic (blue tissue), ischemic non-necrotic (red tissue), and ischemic necrotic areas (pale tissue) were collected and sent to the manufacturer for blood flow analysis (BioPAL, Inc., Worcester, Mass.). Blood flow was calculated as [(FR×CPMT)/CPMR)/tissue weight in grams, where FR=reference sample flow rate (7 mL/min), CPMT=counts per minute in tissue samples and CPMR=counts per minute in the reference blood sample. Blood flow is reported as mL/min/gram tissue.

Analysis of blood flow reveals that both treated groups had similar baseline blood flows in all 3 regions. In the normally perfused non-ischemic zone, blood flow remained relatively constant throughout the experiment with no significant group or time related differences. (Table 3) In the ischemic, non-necrotic (red) and ischemic, necrotic zones (pale), ischemia was characterized by an equivalent and nearly complete loss of blood flow among all three groups. These zones also exhibited normal reactive hyperemia (30 minutes after reperfusion), and blood flow that returned approximated baseline flow levels by the end of the 3 hour reperfusion time. (Table 4).

TABLE 3

Blood flow (ml/minute/gram tissue) from microsphere analysis

Baseline

| | Control | | | −125 mm Hg | | | −50 mm Hg | | |
|---|---|---|---|---|---|---|---|---|---|
| Animal | blue | Red | Pale | blue | Red | Pale | blue | Red | Pale |
| 1 | — | — | — | 0.36 | 0.328 | 0.333 | 0.596 | 1.1 | 0.77 |
| 2 | 1.072 | 0.709 | 0.716 | 0.308 | 0.401 | 0.448 | 0.474 | 0.321 | 0.551 |
| 3 | 0.378 | 0.347 | 0.505 | 0.392 | 0.411 | 0.353 | 0.531 | 0.444 | 0.422 |
| 4 | 0.577 | 0.729 | 0.599 | 0.643 | 1.32 | 0.82 | 0.625 | 0.629 | 0.699 |

TABLE 3-continued

Blood flow (ml/minute/gram tissue) from microsphere analysis

| | | | | | | | | |
|---|---|---|---|---|---|---|---|---|
| 5 | 0.376 | 0.495 | 0.412 | 0.423 | 0.687 | 0.482 | 0.393 | 0.57 | 0.596 |
| Mean | 0.603 | 0.57 | 0.558 | 0.4252 | 0.629 | 0.487 | 0.524 | 0.613 | 0.608 |
| SD | 0.33 | 0.18 | 0.13 | 0.13 | 0.41 | 0.20 | 0.09 | 0.30 | 0.13 |
| N | 4 | 4 | 4 | 5 | 5 | 5 | 5 | 5 | 5 |
| SEM | 0.16 | 0.09 | 0.07 | 0.06 | 0.18 | 0.09 | 0.04 | 0.13 | 0.06 |

During Occlusion

| | Control | | | −125 mm Hg | | | −50 mm Hg | | |
|---|---|---|---|---|---|---|---|---|---|
| Animal | Blue | Red | pale | blue | Red | pale | blue | Red | pale |
| 1 | — | — | — | 0.345 | 0.065 | 0.012 | 0.387 | 0.056 | 0.025 |
| 2 | 1.031 | 0.073 | 0.0255 | 0.335 | 0.064 | 0.029 | 0.352 | 0.008 | 0.029 |
| 3 | 0.3 | 0.016 | 0.022 | 1.196 | 0.06 | 0.051 | 0.714 | 0.024 | 0.041 |
| 4 | 0.428 | 0.129 | 0.017 | 0.454 | 0.084 | 0.071 | 0.494 | 0.038 | 0.035 |
| 5 | 0.4 | 0.024 | 0.011 | 0.509 | 0.054 | 0.029 | 0.441 | 0.037 | 0.1 |
| Mean | 0.540 | 0.061 | 0.0189 | 0.568 | 0.065 | 0.038 | 0.478 | 0.033 | 0.046 |
| SD | 0.33 | 0.05 | 0.01 | 0.36 | 0.01 | 0.02 | 0.14 | 0.02 | 0.03 |
| N | 4 | 4 | 4 | 5 | 5 | 5 | 5 | 5 | 5 |
| SEM | 0.17 | 0.03 | 0.00 | 0.16 | 0.01 | 0.01 | 0.06 | 0.01 | 0.01 |

Reperfusion 30 minutes

| | Control | | | −125 mm Hg | | | −50 mm Hg | | |
|---|---|---|---|---|---|---|---|---|---|
| Animal | blue | red | pale | blue | Red | pale | blue | red | pale |
| 1 | — | — | — | 0.379 | 1.341 | 1.022 | 0.441 | 1.355 | 2.361 |
| 2 | 1.102 | 1.522 | 1.872 | 0.37 | 0.559 | 0.692 | 0.402 | 0.628 | 0.708 |
| 3 | 0.348 | 0.54 | 0.286 | 0.298 | 0.878 | 0.6 | 0.741 | 1.699 | 1.626 |
| 4 | 0.439 | 1.054 | 1.225 | 1.439 | 0.909 | 1.288 | 0.603 | 1.126 | 1.477 |
| 5 | 0.496 | 1.272 | 1.4 | — | — | — | 0.676 | 1.866 | 1.147 |
| Mean | 0.596 | 1.097 | 1.196 | 0.622 | 0.922 | 0.901 | 0.573 | 1.335 | 1.464 |
| SD | 0.34 | 0.42 | 0.67 | 0.55 | 0.32 | 0.32 | 0.15 | 0.49 | 0.61 |
| N | 4 | 4 | 4 | 4 | 4 | 4 | 5 | 5 | 5 |
| SEM | 0.17 | 0.21 | 0.33 | 0.27 | 0.16 | 0.16 | 0.07 | 0.22 | 0.27 |

Reperfusion 180 minutes

| | Control | | | −125 mm Hg | | | −50 mm Hg | | |
|---|---|---|---|---|---|---|---|---|---|
| Animal | blue | red | pale | blue | Red | Pale | blue | red | Pale |
| 1 | — | — | — | 0.404 | 0.367 | 0.795 | 0.467 | 0.385 | 0.837 |
| 2 | 1.102 | 1.522 | 1.872 | 0.291 | 0.365 | 0.6 | 0.593 | 0.186 | 0.649 |
| 3 | 0.348 | 0.54 | 0.286 | 0.38 | 0.303 | 0.515 | 0.804 | 0.649 | 0.699 |
| 4 | 0.439 | 1.054 | 1.225 | 0.513 | 0.449 | 0.845 | 0.912 | 0.803 | 0.946 |
| 5 | 0.496 | 1.272 | 1.4 | 0.53 | 0.477 | 0.76 | 0.483 | 0.471 | 0.495 |
| Mean | 0.596 | 1.097 | 1.196 | 0.424 | 0.392 | 0.703 | 0.652 | 0.499 | 0.725 |
| SD | 0.34 | 0.42 | 0.67 | 0.10 | 0.07 | 0.14 | 0.20 | 0.24 | 0.17 |
| N | 4 | 4 | 4 | 5 | 5 | 5 | 5 | 5 | 5 |
| SEM | 0.17 | 0.21 | 0.33 | 0.04 | 0.03 | 0.06 | 0.09 | 0.11 | 0.08 |

TABLE 4

Regional Myocardial blood flow (mL/min/100 g tissue)

| | Control | | | −50 mm Hg | | | −125 mm Hg | | |
|---|---|---|---|---|---|---|---|---|---|
| | Blue | Red | Pale | Blue | Red | Pale | Blue | Red | Pale |
| Baseline | 0.60 ± 0.16 | 0.57 ± 0.09 | 0.56 ± 0.07 | 0.52 ± 0.04 | 0.61 ± 0.13 | 0.61 ± 0.06 | 0.43 ± 0.06 | 0.63 ± 0.18 | 0.49 ± 0.09 |
| Occlusion | 0.54 ± 0.17 | 0.06 ± 0.03[†] | 0.02 ± 0.00[†] | 0.48 ± 0.06 | 0.03 ± 0.01[†] | 0.05 ± 0.01[†] | 0.57 ± 0.16 | 0.07 ± 0.01[†] | 0.04 ± 0.01 |
| R30 | 0.60 ± 0.17 | 1.10 ± 0.21 | 1.2 ± 0.33[†] | 0.57 ± 0.07 | 1.33 ± 0.22[†] | 1.46 ± 0.27[*†] | 0.62 ± 0.27 | 0.92 ± 0.16[†] | 0.90 ± 0.16 |
| R180 | 0.41 ± 0.04 | 1.39 ± 0.35[†] | 0.95 ± 0.16 | 0.65 ± 0.09 | 0.50 ± 0.11 | 0.73 ± 0.08 | 0.42 ± 0.04 | 0.39 ± 0.03 | 0.70 ± 0.06[*] |

Regional myocardial blood flow was determined in 3 regions of the heart: 1) non-ischemic left ventricle; 2) ischemic, non-necrotic left ventricle; 3) necrotic left ventricle.
[*]$p < 0.05$ vs Control within a time period and within tissue area;
[†]$p < 0.05$ vs. Baseline within group and tissue area.

Example 3

A subsequent study was performed to examine resorbable vacuum dressings and overlay covers. One animal was sedated, prepared for surgery as described, and the heart exposed through a mid-line sternotomy. Branches of the LAD were ligated for 90 minutes. The dressing was prepared by freeze drying. A solution of chitosan (1.33% weight/volume in 2% acetic acid, 20 ml total volume) was poured into an appropriately sized mold. The solution was frozen for 2 hours at −70° C., then transferred to the lyophylizer for 24 hours. The dressing was cross-linked by 2.5% glutaraldehyde vapor for 12 hours to provide a porous material. The overlay cover was an electrospun mixture of Type I collagen and poly 1,8-octanediol citrate (POC) (80%:20% weight/weight). The solution concentration was 15% dissolved in hexafluoro-20proponal (HFIP) with a total volume of 9.5 ml. The solution was ejected from a syringe through an 18 gauge needle at a flow rate of 3 ml/hour. The voltage was 25 KV with a working distance of 25 cm. The film was then heat polymerized at 80° C. for 48 hours and cross-linked in 2.5% glutaraldehyde vapor for 24 hours. The overlay cover was able to maintain the vacuum for the duration of the experiment. However, the vacuum dressing did not distribute the vacuum equally throughout the dressing due to collapse and flow of the material under vacuum.

Example 4

A further study was performed to test variations of the overlay cover. Three animals were sedated and the heart exposed through a midline sternotomy. No infarct was created in this study of materials. The overlay cover was created similar to Example 3, but with variations, including changes in voltage, flow rate, and concentration of glutaraldehyde vapor for cross-linking. For these animals, the porous material vacuum dressing was formed from a solution of 80% Type I collagen/20% POC, 12% total concentration in 8.5 ml HFIP was used. The flow rate was 2 ml/hour, with the fluid ejected through an 18 gauge needle at 35 KV with a working distance of 25 cm. The film was heat polymerized at 80° C. for 48 hours, then cross-linked with exposure to 5% glutaraldehyde vapor for 24 hours. The evacuation tube was sutured to a thin polyvinyl alcohol dressing. The dressing was placed over a portion of the left ventricle and tacked in place with 2-4 sutures. The overlay cover was placed over the dressing and fibrin glue was placed around the edges of the overlay cover to insure a vacuum seal. 50 mm Hg was applied continuously to the dressing. For two animals a small air leak developed after approximately 2.5 hours, the source of the leak was not identified despite a diligent search for the source. The source of the leak could have been at the site of a wrinkle in the overlay cover, a tail of the suture material could have punctured a hole in the overlay cover, fluid collecting in the pericardial sack could have 'floated' a small portion of the cover off the heart tissue, etc. For the third animal, the negative pressure was maintained for the duration of the study (4 hours application of negative pressure).

Example 5

Two animals were used to test the dressing. The surgical technique was similar to that used above. These animals were sedated, prepped for surgery and the heart exposed through an midline sternotomy. Branches of the left anterior descending artery were ligated for 75 minutes. A dressing was made by casting polycaprolactone (PCL). Polycaprolactone was mixed with sodium chloride (1 part caprolactone to 10 parts sodium chloride) and placed in a sufficient volume of chloroform to dissolve the components. 8 ml of the solution was poured into an appropriately sized and shaped container and allowed to dry for twelve hours. The sodium chloride was then leached out in water for 24 hours. The dressing was cut to the size of the ischemic area. The evacuation tube was sutured to the dressing and the dressing placed over the ischemic area and tacked into place. At the end of the 75 minutes of ischemia the tissue was reperfused. The dressing was covered with AlloDerm® and fibrin glue was placed around the edges of the AlloDerm®. 50 mm Hg vacuum was applied for 3 hours. At the end of this time the heart was stained for area of risk, removed and then counter stained for area of necrosis as described for Examples 1 and 2. For the first animal, the area at risk (ischemic area, AAR) was fairly small at 7.9% of the left ventricle (LV). The infarct size (area of necrosis divided by area at risk (AN/AAR×100%) was very small at 2.6% of the area at risk. For the second animal, the area at risk was larger at 14.3% (AAR/LV), with an infarct size (AN/AAR) of 11.52%.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

What is claimed is:

1. A method for treating damaged cardiac tissue using sub-atmospheric pressure, comprising:
   i. placing a porous material proximate the damaged cardiac tissue to provide gaseous communication between one or more pores of the porous material and the damaged cardiac tissue, the porous material comprising at least one of an electrospun material, a cast material, an open-cell foam, and a printed material;
   ii. sealing the porous material in situ over the damaged cardiac tissue to provide a region about the damaged cardiac tissue for maintaining sub-atmospheric pressure at the damaged cardiac tissue, and locating a bio-incorporable cover over the damaged cardiac tissue and sealing the bio-incorporable cover to cardiac tissue proximate the damaged cardiac tissue;
   iii. operably connecting a vacuum source in gaseous communication with the porous material for producing sub-atmospheric pressure at the damaged cardiac tissue; and
   iv. activating the vacuum source to provide sub-atmospheric pressure at the damaged cardiac tissue.

2. The method for treating damaged cardiac tissue according to claim 1, wherein the porous material comprises a bio-incorporable material.

3. The method for treating damaged cardiac tissue according to claim 2, wherein the rate of bio-incorporation of the dressing is higher at the periphery of the dressing than at the center of the dressing.

4. The method for treating damaged cardiac tissue according to claim 1, wherein the porous material comprises a polyethylene, polyurethane, polyester material, or combinations thereof.

5. The method for treating damaged cardiac tissue according to claim 1, wherein the step of placing a porous material proximate the damaged cardiac tissue comprises placing a polyvinyl alcohol foam in direct contact with the damaged cardiac tissue.

6. A method for treating damaged cardiac tissue using sub-atmospheric pressure, comprising:
  i. placing a porous bio-incorporable material proximate the damaged cardiac tissue to provide gaseous communication between one or more pores of the porous material and the damaged cardiac tissue;
  ii. sealing the porous material in situ over the damaged cardiac tissue to provide a region about the damaged cardiac tissue for maintaining sub-atmospheric pressure at the damaged cardiac tissue, and locating a bio-incorporable cover over the damaged cardiac tissue and sealing the bio-incorporable cover to cardiac tissue proximate the damaged cardiac tissue;
  iii. operably connecting a vacuum source in gaseous communication with the porous material for producing sub-atmospheric pressure at the damaged cardiac tissue; and
  iv. activating the vacuum source to provide sub-atmospheric pressure at the damaged cardiac tissue.

7. The method for treating damaged cardiac tissue according to claim 6, wherein the rate of bio-incorporation of the dressing is higher at the periphery of the dressing than at the center of the dressing.

8. The method for treating damaged cardiac tissue according to claim 1 or 6, wherein the porous material comprises myocardial, peripheral muscle cells, or combinations thereof.

9. The method for treating damaged cardiac tissue according to claim 1 or 6, wherein the step of operably connecting a vacuum source comprises connecting a tube between the vacuum source and the porous material, the tube having a distal end in contact with the porous material.

10. The method for treating damaged cardiac tissue according to claim 1 or 6, wherein the step of placing a porous material proximate the damaged cardiac tissue comprises placing the porous material in direct contact with the damaged cardiac tissue.

11. The method for treating damaged cardiac tissue according to claim 10, wherein the porous material comprises an open-cell foam.

12. The method for treating damaged cardiac tissue according to claim 1 or 6, wherein the step of placing a porous material proximate the damaged cardiac tissue comprises placing the porous material in indirect contact with the damaged cardiac tissue by locating a porous intermediate material between the porous material and the damaged heart tissue, with the porous intermediate material disposed in contact with both the porous material and the damaged heart tissue.

13. The method for treating damaged cardiac tissue according to claim 12, wherein the porous material comprises an open-cell foam.

14. The method for treating damaged cardiac tissue according to claim 1 or 6, wherein the cover comprises a vacuum port for receiving sub-atmospheric pressure from the vacuum source, and wherein the step of operably connecting a vacuum source in gaseous communication with the porous material comprises connecting the vacuum source with the vacuum port.

15. The method for treating damaged cardiac tissue according to claim 1 or 6, wherein the step of sealing the cover to tissue surrounding the damaged cardiac tissue comprises adhesively sealing and adhering the cover to cardiac tissue surrounding the damaged cardiac tissue.

16. The method for treating damaged cardiac tissue according to claim 1 or 6, wherein the step of locating a cover comprises locating a self-adhesive sheet over the damaged cardiac tissue, and wherein the step of sealing the cover comprises adhesively sealing and adhering the self-adhesive sheet to cardiac tissue surrounding the damaged cardiac tissue to form a seal between the sheet and surrounding cardiac tissue.

17. The method for treating damaged cardiac tissue according to claim 1 or 6, wherein the cover comprises an electrospun material.

18. The method for treating damaged cardiac tissue according to claim 1 or 6, wherein the cover comprises a cast material.

19. The method for treating damaged cardiac tissue according to claim 1 or 6, wherein the cover comprises collagen.

20. The method for treating damaged cardiac tissue according to claim 17, wherein the cover comprises collagen.

21. The method for treating damaged cardiac tissue according to claim 1 or 6, wherein the cover comprises a diol citrate.

22. The method for treating damaged cardiac tissue according to claim 17 wherein the cover comprises a diol citrate.

23. The method for treating damaged cardiac tissue according to claim 1 or 6, wherein the cover comprises poly 1,8-octanediol citrate.

24. The method for treating damaged cardiac tissue according to claim 17, wherein the cover comprises poly 1,8-octanediol citrate.

25. The method for treating damaged cardiac tissue according to claim 1 or 6, wherein the cover comprises chitosan.

26. The method for treating damaged cardiac tissue according to claim 19, wherein the cover comprises chitosan.

27. The method for treating damaged cardiac tissue according to claim 1 or 6, wherein the cover comprises polylactic acid.

28. The method for treating damaged cardiac tissue according to claim 17, wherein the cover comprises polylactic acid.

29. The method for treating damaged cardiac tissue according to claim 1 or 6, comprising maintaining the sub-atmospheric pressure at the damaged cardiac tissue for a time sufficient to decrease edema in the damaged cardiac tissue.

30. The method for treating damaged cardiac tissue according to claim 1 or 6, comprising maintaining the sub-atmospheric pressure at the damaged cardiac tissue for a time sufficient to decrease mediators, degradation products, toxins, or combinations thereof that enhance the inflammatory and pathophysiological response in the damaged cardiac tissue.

31. The method for treating damaged cardiac tissue according to claim 1 or 6, comprising maintaining a sub-atmospheric pressure of about 25 mm Hg below atmospheric pressure at the damaged cardiac tissue.

32. The method for treating damaged cardiac tissue according to claim 1 or 6, comprising maintaining sub-atmospheric pressure of between about 25 and 125 mm Hg below atmospheric pressure at the damaged cardiac tissue.

33. The method for treating damaged cardiac tissue according to claim 1 or 6, wherein the step of placing a porous material comprises placing a porous material having pores sufficiently small to prevent the ingrowth of tissue therein.

34. The method for treating damaged cardiac tissue according to claim 33, wherein the step of placing a porous material comprises placing a porous material having a pore size smaller than the size of fibroblasts.

35. The method for treating damaged cardiac tissue according to claim 1 or 6, wherein the porous material comprises collagen.

36. The method for treating damaged cardiac tissue according to claim 1 or 6, wherein the porous material comprises chitosan.

37. The method for treating damaged cardiac tissue according to claim 1 or 6, wherein the porous material comprises polycaprolactone.

38. The method for treating damaged cardiac tissue according to claim 1 or 6, wherein the porous material comprises a polyglycolic, polylactic acid, or combinations thereof.

39. The method for treating damaged cardiac tissue according to claim 1 or 6, wherein the porous material comprises a porous, open-cell collagen material.

40. The method for treating damaged cardiac tissue according to claim 1 or 6, wherein the porous material comprises a porous synthetic polymer material.

41. The method for treating damaged cardiac tissue according to claim 1 or 6, wherein the porous material comprises at least one of a porous sheet and a flexible, sheet-like mesh.

42. The method for treating damaged cardiac tissue according to claim 1 or 6, wherein the porous material comprises two or more layers, with the layer closest to the damaged cardiac tissue containing pores sufficiently small at the interface between the porous material and the damaged cardiac tissue to prevent the growth of tissue therein.

43. The method for treating damaged cardiac tissue according to claim 42, wherein the porous material comprises a pore size sufficiently large to promote the formation of granulation tissue at other tissues in the spaces surrounding the damaged cardiac tissue.

44. The method for treating damaged cardiac tissue according to claim 1 or 6, wherein the porous material comprises pores sufficiently small at the interface between the porous material and the damaged cardiac tissue to prevent the growth of tissue therein.

45. The method for treating damaged cardiac tissue according to claim 1 or 6, wherein the porous material comprises a pore size large enough to allow movement of proteins the size of albumin therethrough to permit undesirable compounds to be removed.

46. The method for treating damaged cardiac tissue according to claim 1 or 6, wherein the porous material is sealed to prevent the transmission of sub-atmospheric pressure on all surfaces but one.

47. The method for treating damaged cardiac tissue according to claim 1 or 6, comprising infusing peripheral muscle cells into the damaged cardiac tissue.

48. The method for treating damaged cardiac tissue according to claim 1 or 6, comprising infusing myocardial cells into the damaged cardiac tissue.

49. The method for treating damaged cardiac tissue according to claim 1 or 6, comprising infusing pleuripotent progenitor cells into the damaged cardiac tissue.

* * * * *